US009588582B2

(12) United States Patent
Connor et al.

(10) Patent No.: US 9,588,582 B2
(45) Date of Patent: Mar. 7, 2017

(54) MOTION RECOGNITION CLOTHING (TM) WITH TWO DIFFERENT SETS OF TUBES SPANNING A BODY JOINT

(71) Applicants: Robert A. Connor, Forest Lake, MN (US); Jedidiah Behymer, Woodbury, MN (US); Matthew Hardyman, Minneapolis, MN (US); Matt Hericks, Woodbury, MN (US); Garrison Hommer, Minneapolis, MN (US); Gus Lopez, Eagan, MN (US); Tyler Olson, Plymouth, MN (US); John Smida, Brooklyn Park, MN (US); Alex Stein, Minneapolis, MN (US); Daniel Valencia, Ontario (CA); Eric Wong, Roseville, MN (US)

(72) Inventors: Robert A. Connor, Forest Lake, MN (US); Jedidiah Behymer, Woodbury, MN (US); Matthew Hardyman, Minneapolis, MN (US); Matt Hericks, Woodbury, MN (US); Garrison Hommer, Minneapolis, MN (US); Gus Lopez, Eagan, MN (US); Tyler Olson, Plymouth, MN (US); John Smida, Brooklyn Park, MN (US); Alex Stein, Minneapolis, MN (US); Daniel Valencia, Ontario (CA); Eric Wong, Roseville, MN (US)

(73) Assignee: Medibotics LLC, St. Paul, MN (US)

( * ) Notice: Subject to any disclaimer, the term of this patent is extended or adjusted under 35 U.S.C. 154(b) by 342 days.

(21) Appl. No.: 14/463,741

(22) Filed: Aug. 20, 2014

(65) Prior Publication Data
US 2015/0075303 A1    Mar. 19, 2015

Related U.S. Application Data

(60) Provisional application No. 61/878,893, filed on Sep. 17, 2013.

(51) Int. Cl.
  *G06F 3/01* (2006.01)
  *A41D 13/12* (2006.01)
  (Continued)

(52) U.S. Cl.
  CPC .......... *G06F 3/011* (2013.01); *A41D 13/1281* (2013.01); *A61B 5/1126* (2013.01);
  (Continued)

(58) Field of Classification Search
  CPC .......... G01F 3/011; G01F 3/012; G01F 3/014; G01F 3/017; A61B 5/1126;
  (Continued)

(56) References Cited

U.S. PATENT DOCUMENTS 3,974,491 A    8/1976    Sipe
4,542,291 A    9/1985    Zimmerman
(Continued)

OTHER PUBLICATIONS

"Animazoo—3D Motion Capture Equipment: Gypsy Products from Animazoo", [online]. © 2004 Animazoo. [retrieved Jul. 16, 2007]. Retrieved from the Internet: <URL: http://www.animazoo.com/products/index.htm>, 1 pg.
(Continued)

*Primary Examiner* — Daniel S Larkin
*Assistant Examiner* — Nathaniel Kolb

(57) ABSTRACT

This invention can be embodied in smart clothing for recognizing full-body human motion based on the pressure levels of a flowable substance within two different sets of flexible tubes or channels which are integrated into clothing (or a wearable accessory) and which span the same body joint. This technology can be used to create a wearable, mobile, reasonably-priced, and relatively-unobtrusive full-body motion-capture system which can be used in diverse
(Continued)

environments. Compared to camera-based motion capture systems, this invention can be mobile and does not suffer from optical occlusion.

3 Claims, 14 Drawing Sheets

(51) Int. Cl.
    *A61B 5/00*              (2006.01)
    *A61B 5/107*           (2006.01)
    *A61B 5/11*             (2006.01)

(52) U.S. Cl.
    CPC .............. *G06F 3/017* (2013.01); *A61B 5/002* (2013.01); *A61B 5/0024* (2013.01); *A61B 5/1071* (2013.01); *A61B 5/1121* (2013.01); *A61B 5/4528* (2013.01); *A61B 5/4585* (2013.01); *A61B 5/6804* (2013.01); *A61B 5/6831* (2013.01); *A61B 2505/09* (2013.01); *A61B 2562/0247* (2013.01); *A61B 2562/046* (2013.01); *Y10T 29/49826* (2015.01)

(58) Field of Classification Search
    CPC   A61B 5/6811–5/6829; G06K 9/00342; G06K 9/00348
    USPC ........................................................ 73/865.4
    See application file for complete search history.

(56) References Cited

U.S. PATENT DOCUMENTS

| | | |
|---|---|---|
| 4,940,063 A | 7/1990 | Challis |
| 5,012,819 A | 5/1991 | Marras et al. |
| 5,086,785 A | 2/1992 | Gentile et al. |
| 5,125,412 A | 6/1992 | Thornton |
| 5,152,293 A | 10/1992 | Vonesh et al. |
| 5,184,009 A | 2/1993 | Wright et al. |
| 5,184,319 A | 2/1993 | Kramer |
| 5,203,340 A | 4/1993 | Gustafson et al. |
| 5,250,227 A | 10/1993 | Margolin |
| 5,280,265 A | 1/1994 | Kramer et al. |
| 5,337,758 A | 8/1994 | Moore et al. |
| 5,375,610 A | 12/1994 | LaCourse et al. |
| 5,442,729 A | 8/1995 | Kramer et al. |
| 5,474,083 A | 12/1995 | Church et al. |
| 5,533,531 A | 7/1996 | Edwards et al. |
| 5,592,401 A | 1/1997 | Kramer |
| 5,610,528 A | 3/1997 | Neely et al. |
| 5,676,157 A | 10/1997 | Kramer |
| 5,694,497 A | 12/1997 | Sansone |
| 5,791,231 A | 8/1998 | Cohn et al. |
| 5,891,060 A | 4/1999 | McGregor et al. |
| 5,912,658 A | 6/1999 | Bergamasco et al. |
| 5,930,741 A | 7/1999 | Kramer |
| 5,954,674 A | 9/1999 | Fuhr |
| 5,961,541 A | 10/1999 | Ferrati |
| 5,963,891 A | 10/1999 | Walker et al. |
| 5,980,472 A | 11/1999 | Seyl |
| 6,005,548 A | 12/1999 | Latypov et al. |
| 6,032,530 A | 3/2000 | Hock |
| 6,035,274 A | 3/2000 | Kramer et al. |
| 6,042,555 A | 3/2000 | Kramer et al. |
| 6,050,962 A | 4/2000 | Kramer et al. |
| 6,059,576 A | 5/2000 | Brann |
| 6,061,004 A | 5/2000 | Rosenberg |
| 6,067,077 A | 5/2000 | Martin et al. |
| 6,095,991 A | 8/2000 | Krausman et al. |
| 6,104,379 A | 8/2000 | Petrich et al. |
| 6,104,382 A | 8/2000 | Martin et al. |
| 6,110,130 A | 8/2000 | Kramer |
| 6,119,516 A | 9/2000 | Hock |
| 6,127,672 A | 10/2000 | Danisch |
| 6,142,982 A | 11/2000 | Hunt et al. |
| 6,148,280 A | 11/2000 | Kramer |
| 6,162,190 A | 12/2000 | Kramer |
| 6,162,191 A | 12/2000 | Foxlin |
| 6,165,143 A | 12/2000 | van Lummel |
| 6,201,533 B1 | 3/2001 | Rosenberg et al. |
| 6,210,301 B1 | 4/2001 | Abraham-Fuchs et al. |
| 6,246,390 B1 | 6/2001 | Rosenberg |
| 6,259,382 B1 | 7/2001 | Rosenberg |
| 6,271,828 B1 | 8/2001 | Rosenberg et al. |
| 6,307,481 B1 | 10/2001 | Lehrman et al. |
| 6,341,504 B1 | 1/2002 | Istook |
| 6,342,880 B2 | 1/2002 | Rosenberg et al. |
| 6,360,615 B1 | 3/2002 | Smela |
| 6,361,507 B1 | 3/2002 | Foxlin |
| 6,369,564 B1 | 4/2002 | Khalfin et al. |
| 6,389,187 B1 | 5/2002 | Greenaway et al. |
| 6,400,139 B1 | 6/2002 | Khalfin et al. |
| 6,400,352 B1 | 6/2002 | Bruneau et al. |
| 6,409,687 B1 | 6/2002 | Foxlin |
| 6,413,229 B1 | 7/2002 | Kramer et al. |
| 6,428,490 B1 | 8/2002 | Kramer et al. |
| 6,466,200 B1 | 10/2002 | Anton et al. |
| 6,486,872 B2 | 11/2002 | Rosenberg et al. |
| 6,487,906 B1 | 12/2002 | Hock |
| 6,497,672 B2 | 12/2002 | Kramer |
| 6,513,532 B2 | 2/2003 | Mault et al. |
| 6,519,862 B1 | 2/2003 | Owsley et al. |
| 6,527,711 B1 | 3/2003 | Stivoric et al. |
| 6,563,107 B2 | 5/2003 | Danisch et al. |
| 6,579,248 B1 | 6/2003 | Cascone et al. |
| 6,624,626 B2 | 9/2003 | Khalfin |
| 6,636,161 B2 | 10/2003 | Rosenberg |
| 6,640,202 B1 | 10/2003 | Dietz et al. |
| 6,651,352 B2 | 11/2003 | McGorry et al. |
| 6,673,027 B2 | 1/2004 | Fischer |
| 6,692,449 B1 | 2/2004 | Brown |
| 6,697,048 B2 | 2/2004 | Rosenberg et al. |
| 6,700,499 B2 | 3/2004 | Kubo et al. |
| 6,701,296 B1 | 3/2004 | Kramer et al. |
| 6,703,939 B2 | 3/2004 | Lehrman et al. |
| 6,704,001 B1 | 3/2004 | Schena et al. |
| 6,704,002 B1 | 3/2004 | Martin et al. |
| 6,705,871 B1 | 3/2004 | Bevirt et al. |
| 6,731,268 B2 | 5/2004 | Anton et al. |
| 6,733,464 B2 | 5/2004 | Olbrich et al. |
| 6,762,600 B2 | 7/2004 | Khalfin |
| 6,786,877 B2 | 9/2004 | Foxlin |
| 6,831,603 B2 | 12/2004 | Menache |
| 6,834,436 B2 | 12/2004 | Townsend et al. |
| 6,836,744 B1 | 12/2004 | Asphahani et al. |
| 6,864,796 B2 | 3/2005 | Lehrman et al. |
| 6,866,643 B2 | 3/2005 | Kramer |
| 6,871,413 B1 | 3/2005 | Arms et al. |
| 6,890,312 B1 | 5/2005 | Priester et al. |
| 6,903,721 B2 | 6/2005 | Braun et al. |
| 6,940,062 B2 | 9/2005 | Kwon et al. |
| 6,946,812 B1 | 9/2005 | Martin et al. |
| 6,957,164 B2 | 10/2005 | Dietz et al. |
| 6,984,208 B2 | 1/2006 | Zheng |
| 6,985,134 B2 | 1/2006 | Suprun et al. |
| 6,997,882 B1 | 2/2006 | Parker et al. |
| 7,009,561 B2 | 3/2006 | Menache et al. |
| 7,028,547 B2 | 4/2006 | Shiratori et al. |
| 7,070,571 B2 | 7/2006 | Kramer et al. |
| 7,087,075 B2 | 8/2006 | Briscoe et al. |
| 7,095,331 B2 | 8/2006 | Lehrman et al. |
| 7,102,541 B2 | 9/2006 | Rosenberg |
| 7,135,227 B2 | 11/2006 | Karayianni et al. |
| 7,141,026 B2 | 11/2006 | Aminian et al. |
| 7,145,461 B2 | 12/2006 | Lehrman et al. |
| 7,149,584 B1 | 12/2006 | Koh et al. |
| 7,153,262 B2 | 12/2006 | Stivoric et al. |
| 7,167,743 B2 | 1/2007 | Heruth et al. |
| 7,191,652 B2 | 3/2007 | Pristup et al. |
| 7,191,803 B2 | 3/2007 | Orr et al. |
| 7,209,028 B2 | 4/2007 | Boronkay et al. |
| 7,209,776 B2 | 4/2007 | Leitner |
| 7,210,240 B2 | 5/2007 | Townsend et al. |
| 7,212,943 B2 | 5/2007 | Aoshima et al. |

(56) References Cited

U.S. PATENT DOCUMENTS

| | | |
|---|---|---|
| 7,219,033 B2 | 5/2007 | Kolen |
| 7,236,157 B2 | 6/2007 | Schena et al. |
| 7,245,292 B1 | 7/2007 | Custy |
| 7,249,422 B2 | 7/2007 | Bergamasco et al. |
| 7,249,951 B2 | 7/2007 | Bevirt et al. |
| 7,264,554 B2 | 9/2007 | Bentley |
| 7,292,151 B2 | 11/2007 | Ferguson et al. |
| 7,292,223 B2 | 11/2007 | Suprun et al. |
| 7,295,184 B2 | 11/2007 | Suprun et al. |
| 7,296,469 B2 | 11/2007 | Simonenko et al. |
| 7,312,786 B2 | 12/2007 | Anderson et al. |
| 7,313,440 B2 | 12/2007 | Miesel |
| 7,324,714 B1 | 1/2008 | Cranch et al. |
| 7,328,070 B2 | 2/2008 | Gerber et al. |
| 7,330,760 B2 | 2/2008 | Heruth et al. |
| 7,383,728 B2 | 6/2008 | Noble et al. |
| 7,395,113 B2 | 7/2008 | Heruth et al. |
| 7,395,181 B2 | 7/2008 | Foxlin |
| 7,404,716 B2 | 7/2008 | Gregorio et al. |
| 7,413,802 B2 | 8/2008 | Karayianni et al. |
| 7,421,369 B2 | 9/2008 | Clarkson |
| 7,431,703 B2 | 10/2008 | Salvi et al. |
| 7,432,810 B2 | 10/2008 | Menache et al. |
| 7,447,545 B2 | 11/2008 | Heruth et al. |
| 7,447,604 B2 | 11/2008 | Braun et al. |
| 7,450,002 B2 | 11/2008 | Choi et al. |
| 7,451,056 B2 | 11/2008 | Flentov et al. |
| 7,471,290 B2 | 12/2008 | Wang et al. |
| 7,479,890 B2 | 1/2009 | Lehrman et al. |
| 7,492,268 B2 | 2/2009 | Ferguson et al. |
| 7,500,853 B2 | 3/2009 | Bevirt et al. |
| 7,512,515 B2 | 3/2009 | Vock et al. |
| 7,572,228 B2 | 8/2009 | Wolinsky et al. |
| 7,572,253 B2 | 8/2009 | Gotani |
| 7,602,301 B1 | 10/2009 | Stirling et al. |
| 7,602,310 B2 | 10/2009 | Mann et al. |
| 7,627,451 B2 | 12/2009 | Vock et al. |
| 7,628,074 B2 | 12/2009 | Vannucci et al. |
| 7,634,379 B2 | 12/2009 | Noble |
| 7,658,612 B2 | 2/2010 | Lee et al. |
| 7,661,200 B2 | 2/2010 | Bonnet et al. |
| 7,665,288 B2 | 2/2010 | Karayianni et al. |
| 7,672,781 B2 | 3/2010 | Churchill et al. |
| 7,689,378 B2 | 3/2010 | Kolen |
| 7,695,415 B2 | 4/2010 | Goel et al. |
| 7,698,101 B2 | 4/2010 | Alten et al. |
| 7,698,830 B2 | 4/2010 | Townsend et al. |
| 7,703,333 B2 | 4/2010 | Hayakawa et al. |
| 7,715,897 B2 | 5/2010 | Coulston |
| 7,725,279 B2 | 5/2010 | Luinge et al. |
| 7,728,839 B2 | 6/2010 | Yang et al. |
| 7,771,318 B2 | 8/2010 | Narayanaswami |
| 7,774,155 B2 | 8/2010 | Sato et al. |
| 7,780,677 B2 | 8/2010 | Leitner |
| 7,792,583 B2 | 9/2010 | Miesel et al. |
| 7,805,196 B2 | 9/2010 | Miesel et al. |
| 7,811,333 B2 | 10/2010 | Jonsson et al. |
| 7,821,407 B2 | 10/2010 | Shears et al. |
| 7,821,496 B2 | 10/2010 | Rosenberg et al. |
| 7,825,815 B2 | 11/2010 | Shears et al. |
| 7,845,228 B2 | 12/2010 | Bremer et al. |
| 7,850,574 B2 | 12/2010 | Narayanaswami |
| 7,872,638 B2 | 1/2011 | Sato |
| 7,878,030 B2 | 2/2011 | Burr |
| 7,901,756 B2 | 3/2011 | Burr et al. |
| 7,902,095 B2 | 3/2011 | Hassonjee et al. |
| 7,926,254 B2 | 4/2011 | Karayianni et al. |
| 7,931,604 B2 | 4/2011 | Even et al. |
| 7,944,433 B2 | 5/2011 | Schena et al. |
| 7,946,102 B2 | 5/2011 | Karayianni et al. |
| 7,952,483 B2 | 5/2011 | Ferguson et al. |
| 7,977,807 B1 | 7/2011 | Connor |
| 7,978,081 B2 | 7/2011 | Shears et al. |
| 7,980,141 B2 * | 7/2011 | Connor ............... A61B 5/1126 73/849 |
| 8,007,421 B2 | 8/2011 | Goel et al. |
| 8,010,308 B1 | 8/2011 | Churchill |
| 8,010,911 B2 | 8/2011 | Sohn et al. |
| 8,011,229 B2 | 9/2011 | Lieberman et al. |
| 8,013,852 B2 | 9/2011 | Ng-Thow-Hing et al. |
| 8,018,587 B2 | 9/2011 | Kuo et al. |
| 8,029,411 B2 | 10/2011 | Johnson |
| 8,036,851 B2 | 10/2011 | Vock et al. |
| 8,055,021 B2 | 11/2011 | Caritu et al. |
| 8,073,201 B2 | 12/2011 | Satoh et al. |
| 8,073,707 B2 | 12/2011 | Teller et al. |
| 8,082,762 B2 | 12/2011 | Burr |
| 8,083,693 B1 | 12/2011 | McKeon et al. |
| 8,099,258 B2 | 1/2012 | Alten et al. |
| 8,103,472 B2 | 1/2012 | Braun et al. |
| 8,108,190 B2 | 1/2012 | Riener et al. |
| 8,111,165 B2 | 2/2012 | Ortega et al. |
| 8,125,448 B2 | 2/2012 | Ranta et al. |
| 8,135,473 B2 | 3/2012 | Miesel et al. |
| 8,145,291 B2 | 3/2012 | Coulston |
| 8,150,531 B2 | 4/2012 | Skelton |
| 8,151,648 B2 | 4/2012 | Yu et al. |
| 8,157,752 B2 | 4/2012 | Fischer |
| 8,159,354 B2 | 4/2012 | Ferguson et al. |
| 8,161,826 B1 | 4/2012 | Taylor |
| 8,165,840 B2 | 4/2012 | Hatlestad et al. |
| 8,165,844 B2 | 4/2012 | Luinge et al. |
| 8,175,720 B2 | 5/2012 | Skelton et al. |
| 8,180,591 B2 | 5/2012 | Yuen et al. |
| 8,180,592 B2 | 5/2012 | Yuen et al. |
| 8,200,340 B2 | 6/2012 | Skelton et al. |
| 8,203,487 B2 | 6/2012 | Hol et al. |
| 8,207,963 B2 | 6/2012 | Cotter et al. |
| 8,209,028 B2 | 6/2012 | Skelton et al. |
| 8,219,206 B2 | 7/2012 | Skelton et al. |
| 8,226,494 B2 | 7/2012 | Miettinen et al. |
| 8,231,555 B2 | 7/2012 | Skelton et al. |
| 8,249,718 B2 | 8/2012 | Skelton et al. |
| 8,259,996 B2 | 9/2012 | Shamaie |
| 8,280,681 B2 | 10/2012 | Vock et al. |
| 8,284,847 B2 | 10/2012 | Adermann |
| 8,301,575 B2 | 10/2012 | Bonnet et al. |
| 8,308,489 B2 | 11/2012 | Lee et al. |
| 8,311,769 B2 | 11/2012 | Yuen et al. |
| 8,311,770 B2 | 11/2012 | Yuen et al. |
| 8,315,710 B2 | 11/2012 | Skelton et al. |
| 8,316,719 B2 | 11/2012 | Majidi et al. |
| 8,323,218 B2 | 12/2012 | Davis et al. |
| 8,332,041 B2 | 12/2012 | Skelton et al. |
| 8,342,045 B2 | 1/2013 | Maxwell et al. |
| 8,344,948 B2 | 1/2013 | Hol et al. |
| 8,352,211 B2 | 1/2013 | Vock et al. |
| 8,366,641 B2 | 2/2013 | Wang et al. |
| 8,386,008 B2 | 2/2013 | Yuen et al. |
| 8,388,555 B2 | 3/2013 | Panken et al. |
| 8,395,109 B2 | 3/2013 | Muravsky |
| 8,396,554 B2 | 3/2013 | Miesel et al. |
| 8,397,568 B2 | 3/2013 | Cardarelli |
| 8,401,666 B2 | 3/2013 | Skelton et al. |
| 8,403,845 B2 | 3/2013 | Stivoric et al. |
| 8,414,507 B2 | 4/2013 | Asada |
| 8,416,088 B2 | 4/2013 | Ortega et al. |
| 8,416,102 B2 | 4/2013 | Yin |
| 8,421,854 B2 | 4/2013 | Zerkin |
| 8,427,325 B2 | 4/2013 | Ferguson et al. |
| 8,428,686 B2 | 4/2013 | Kuo et al. |
| 8,435,177 B2 | 5/2013 | Lanfermann et al. |
| 8,437,861 B2 | 5/2013 | Skelton et al. |
| 8,437,980 B2 | 5/2013 | Yuen et al. |
| 8,447,401 B2 | 5/2013 | Miesel et al. |
| 8,447,411 B2 | 5/2013 | Skelton et al. |
| 8,454,528 B2 | 6/2013 | Yuen et al. |
| 8,457,719 B2 | 6/2013 | Moctezuma et al. |
| 8,463,576 B2 | 6/2013 | Yuen et al. |
| 8,463,577 B2 | 6/2013 | Yuen et al. |
| 8,475,370 B2 | 7/2013 | McCombie et al. |
| 8,488,888 B2 | 7/2013 | Balan et al. |
| 8,493,082 B2 | 7/2013 | Jeong |
| 8,504,150 B2 | 8/2013 | Skelton |

(56) References Cited

U.S. PATENT DOCUMENTS

| | | |
|---|---|---|
| 8,515,132 B2 | 8/2013 | Shamaie |
| 8,515,549 B2 | 8/2013 | Panken et al. |
| 8,515,550 B2 | 8/2013 | Skelton et al. |
| 8,527,217 B2 | 9/2013 | Moodie |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,552,982 B2 | 10/2013 | Martin et al. |
| 8,579,834 B2 | 11/2013 | Davis et al. |
| 8,583,252 B2 | 11/2013 | Skelton et al. |
| 8,583,402 B2 | 11/2013 | Yuen et al. |
| 8,661,915 B2 | 3/2014 | Taylor |
| 8,670,953 B2 | 3/2014 | Yuen et al. |
| 8,708,904 B2 | 4/2014 | Stivoric et al. |
| 8,761,437 B2 | 6/2014 | Kirovski et al. |
| 2001/0003712 A1 | 6/2001 | Roelofs |
| 2001/0020140 A1 | 9/2001 | Kramer |
| 2001/0020937 A1 | 9/2001 | Rosenberg et al. |
| 2001/0040553 A1 | 11/2001 | Rosenberg |
| 2001/0049470 A1 | 12/2001 | Mault et al. |
| 2002/0088931 A1 | 7/2002 | Danisch et al. |
| 2002/0140674 A1 | 10/2002 | Okuno et al. |
| 2002/0198472 A1 | 12/2002 | Kramer |
| 2003/0023192 A1 | 1/2003 | Foxlin |
| 2003/0036858 A1 | 2/2003 | Friedrichs et al. |
| 2003/0045816 A1 | 3/2003 | Foxlin |
| 2003/0083596 A1 | 5/2003 | Kramer et al. |
| 2004/0017313 A1 | 1/2004 | Menache |
| 2004/0046740 A1 | 3/2004 | Martin et al. |
| 2005/0106977 A1 | 5/2005 | Coulston |
| 2005/0118914 A1 | 6/2005 | Kuo et al. |
| 2006/0022833 A1 | 2/2006 | Ferguson et al. |
| 2006/0053108 A1 | 3/2006 | Raschke |
| 2006/0059976 A1 | 3/2006 | Simonenko et al. |
| 2006/0059988 A1 | 3/2006 | Pristup |
| 2006/0059990 A1 | 3/2006 | Simonenko et al. |
| 2006/0059991 A1 | 3/2006 | Pristup et al. |
| 2006/0064039 A1 | 3/2006 | Griego et al. |
| 2006/0070443 A1 | 4/2006 | Pristup |
| 2006/0144213 A1 | 7/2006 | Mann |
| 2006/0147678 A1 | 7/2006 | Marmaropoulos et al. |
| 2006/0166737 A1 | 7/2006 | Bentley |
| 2006/0184336 A1 | 8/2006 | Kolen |
| 2006/0189899 A1 | 8/2006 | Flaherty et al. |
| 2006/0210112 A1 | 9/2006 | Cohen et al. |
| 2006/0212097 A1 | 9/2006 | Varadan et al. |
| 2006/0217233 A1 | 9/2006 | Lee |
| 2006/0238490 A1 | 10/2006 | Stanley et al. |
| 2006/0241520 A1 | 10/2006 | Robertson |
| 2006/0241521 A1 | 10/2006 | Cohen |
| 2006/0282017 A1 | 12/2006 | Avni et al. |
| 2006/0284979 A1 | 12/2006 | Clarkson |
| 2007/0000324 A9 | 1/2007 | Pristup et al. |
| 2007/0124703 A1 | 5/2007 | Sohn et al. |
| 2007/0173705 A1 | 7/2007 | Teller et al. |
| 2007/0214889 A1 | 9/2007 | Pristup |
| 2007/0219744 A1 | 9/2007 | Kolen |
| 2007/0270214 A1 | 11/2007 | Bentley |
| 2008/0061949 A1 | 3/2008 | Ferguson et al. |
| 2008/0068376 A1 | 3/2008 | Anderson et al. |
| 2008/0120061 A1 | 5/2008 | Higgins et al. |
| 2008/0223131 A1 | 9/2008 | Vannucci et al. |
| 2008/0262772 A1 | 10/2008 | Luinge et al. |
| 2008/0285805 A1 | 11/2008 | Luinge et al. |
| 2009/0022369 A1 | 1/2009 | Satoh et al. |
| 2009/0025483 A1* | 1/2009 | Connor ............... A61B 5/1126 73/849 |
| 2009/0030646 A1 | 1/2009 | Jones et al. |
| 2009/0076419 A1 | 3/2009 | Namineni et al. |
| 2009/0076746 A1 | 3/2009 | Higgins |
| 2009/0149257 A1 | 6/2009 | Ferguson et al. |
| 2009/0171180 A1 | 7/2009 | Pering et al. |
| 2009/0174701 A1 | 7/2009 | Cotter et al. |
| 2009/0204031 A1 | 8/2009 | McNames et al. |
| 2009/0209343 A1 | 8/2009 | Foxlin et al. |
| 2009/0278791 A1 | 11/2009 | Slycke et al. |
| 2010/0049468 A1 | 2/2010 | Papadourakis |
| 2010/0076348 A1 | 3/2010 | McNames et al. |
| 2010/0130873 A1 | 5/2010 | Yuen et al. |
| 2010/0145236 A1 | 6/2010 | Greenberg et al. |
| 2010/0164862 A1 | 7/2010 | Sullivan et al. |
| 2010/0176952 A1 | 7/2010 | Bajcsy et al. |
| 2010/0216602 A1 | 8/2010 | Goel et al. |
| 2010/0240999 A1 | 9/2010 | Droitcour et al. |
| 2010/0277489 A1 | 11/2010 | Geisner et al. |
| 2010/0309209 A1 | 12/2010 | Hodgins et al. |
| 2010/0324456 A1 | 12/2010 | Jonsson et al. |
| 2011/0009194 A1 | 1/2011 | Gabai et al. |
| 2011/0025562 A1 | 2/2011 | Hol et al. |
| 2011/0028865 A1 | 2/2011 | Luinge et al. |
| 2011/0046915 A1 | 2/2011 | Hol et al. |
| 2011/0140723 A1 | 6/2011 | Jeong |
| 2011/0201428 A1 | 8/2011 | Ferguson et al. |
| 2011/0213278 A1 | 9/2011 | Horak et al. |
| 2011/0214030 A1 | 9/2011 | Greenberg et al. |
| 2011/0234452 A1 | 9/2011 | Hol et al. |
| 2011/0296925 A1 | 12/2011 | Miesel et al. |
| 2012/0025945 A1 | 2/2012 | Yazadi et al. |
| 2012/0046901 A1 | 2/2012 | Green et al. |
| 2012/0053890 A1 | 3/2012 | Van Acht et al. |
| 2012/0058860 A1 | 3/2012 | Goel et al. |
| 2012/0116258 A1 | 5/2012 | Lee |
| 2012/0117514 A1 | 5/2012 | Kim et al. |
| 2012/0118066 A1 | 5/2012 | Majidi et al. |
| 2012/0143358 A1 | 6/2012 | Adams et al. |
| 2012/0172126 A1 | 7/2012 | Padovani et al. |
| 2012/0178534 A1 | 7/2012 | Ferguson et al. |
| 2012/0214594 A1 | 8/2012 | Kirovski et al. |
| 2012/0220233 A1 | 8/2012 | Teague et al. |
| 2012/0223880 A1 | 9/2012 | Birnbaum et al. |
| 2012/0274554 A1 | 11/2012 | Kinoshita et al. |
| 2012/0275686 A1 | 11/2012 | Wilson et al. |
| 2012/0280902 A1 | 11/2012 | Persaud et al. |
| 2012/0289296 A1 | 11/2012 | Marty et al. |
| 2012/0289867 A1 | 11/2012 | Kasama |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0319940 A1 | 12/2012 | Bress et al. |
| 2012/0323501 A1 | 12/2012 | Sarrafzadeh et al. |
| 2013/0015976 A1 | 1/2013 | Chang et al. |
| 2013/0068017 A1 | 3/2013 | Perkins et al. |
| 2013/0073248 A1 | 3/2013 | Perkins et al. |
| 2013/0110011 A1 | 5/2013 | McGregor et al. |
| 2013/0172058 A1 | 7/2013 | Marty et al. |
| 2013/0173171 A1 | 7/2013 | Drysdale et al. |
| 2013/0207889 A1 | 8/2013 | Chang et al. |
| 2013/0222565 A1 | 8/2013 | Guerin et al. |
| 2013/0238270 A1 | 9/2013 | Khalfin et al. |
| 2013/0271602 A1 | 10/2013 | Bentley et al. |
| 2013/0289449 A1 | 10/2013 | Stone et al. |
| 2013/0297220 A1 | 11/2013 | Yuen et al. |
| 2014/0015687 A1 | 1/2014 | Narasimhan et al. |
| 2014/0081666 A1 | 3/2014 | Teller et al. |
| 2014/0171834 A1 | 6/2014 | Degoede et al. |
| 2014/0194781 A1 | 7/2014 | Einarsson |
| 2014/0197946 A1 | 7/2014 | Park |
| 2014/0197963 A1 | 7/2014 | Park et al. |
| 2014/0197965 A1 | 7/2014 | Park et al. |
| 2014/0206327 A1 | 7/2014 | Ziemianska et al. |
| 2014/0221769 A1 | 8/2014 | Teller et al. |
| 2014/0223407 A1 | 8/2014 | Teller et al. |
| 2014/0228712 A1 | 8/2014 | Elliott et al. |
| 2014/0228985 A1 | 8/2014 | Elliott et al. |

OTHER PUBLICATIONS

"Ascension Products—Flock of Birds®", [online]. [retrieved Jul. 16, 2007]. Retrieved from the Internet: <URL: http://www.ascension-tech.com/products/flockofbirds.php>, 2 pgs.

"Biometrics Ltd Research—Goniometers and Torsiometers", [online]. [retrieved Jul. 16, 2007]. Retrieved: http://www.biometricsltd.com/y%20gonio.htm>, 2 pgs.

(56) References Cited

OTHER PUBLICATIONS

"Biopac—TSD130A / Twin Axis Goniometer, 110mm", [online]. [retrieved Jul. 16, 2007]. Retrieved from the Internet: <URL: http://www.biopac.com/Research.asp?Pid=3695 &Main=Transducers>, 1 pg.

"Codamotion Products—Hardware and Software", [online]. [retrieved Jul. 16, 2007]. Retrieved from the Internet: <URL: http://www.charndyn.com/Products/Products_Intro.html>, 1 pg.

"Greenleaf Products", [online]. [retrieved Jul. 16, 2007]. Retrieved from the Internet: <URL: http://www.greanleafmed.com/products.htm>, 1 pg.

"High Performance Real-Time 3D Motion Capture Systems for Professionals", [online]. © 1997-2007 Phoenix Technologies Inc. [retrieved Jul. 16, 2007]. Retrieved from the Internet: <URL: http://www.ptiphoenix.com/Products.php>, 1 pg.

"Immersion Corporation—3D Interaction", [online]. © 2007 Immersion Corporation. [retrieved Jul. 16, 2007]. Retrieved from the Internet: <URL: http://www.immersion.com/3d/>, 1 pg.

"Liberty™ Latus™ Wireless Motion Tracking System from Polhemus", [online]. [retrieved Jul. 16, 2007]. Retrieved from the Internet: <URL:. http://www.polhemus.com/?page=Motion_Liberty_Latus>, 2 pgs.

"Measurand—Motion Capture for the Classroom", [online]. [retrieved Jul. 16, 2007]. Retrieved from the Internet: <URL: http://www.measurand.com>, 1 pg.

"Meta Motion—Motion Capture Hardware—Face Trackers", [online]. © 2006 Meta Motion. [retrieved Jul. 16, 2007]. Retrieved from the Internet: <URL: http://www.metamotion.com/hardware/motion-capture-hardware.htm>, 1 pg.

"MicroStrain® Inclinometers: Orientation Sensors", [online]. [retrieved Jul. 16, 2007]. Retrieved from the Internet: <URL: http://www.microstrain.com/inclinometers.aspx>, 1 pg.

"Mikromak Service Brinkmann—Human Motion", [online]. © Mikromak Service Brinkmann. [retrieved Jul. 16, 2007]. Retrieved from the Internet: http://www.mikromak.com/en/en_menschl_beweg.htm>, 1 pg.

"MiniSun—IDEEA Information", [online]. © MiniSun 2000-2007. [retrieved Jul. 16, 2007]. Retrieved from the Internet: <URL: http://www.minisun.com/ideea.asp>, 1 pg.

"Motek Medical", [online]. [archived Jul. 8, 2007]. Retrieved from the Internet: <URL: http://web.archive.org/web/20070708132130/ http://www.e-motek.com/medical/index.htm>, 2 pgs.

"Motion Lab Systems, Inc.", [online]. ©1995-2007 Motion Lab Systems, Inc. [retrieved Jul. 16, 2007]. Retrieved via the Internet: <URL: http://www.emgsrus.com>, 2 pgs.

"MotionAnalysis—Movement Analysis Products", [online]. © 2007 Motion Analysis Corporation. [retrieved Jul. 16, 2007]. Retrieved from the Internet: <URL: http://www.motionanalysis.com/applications/movement/movementproducts.html>, 1 pg.

"NCHS Study—Prevalence of Overweight and Obesity Among Adults: United States, 1999-2002", [online]. [retrieved Mar. 28, 2008]. Retrieved from the Internet: <URL: http://www.cdc.gov/nchs/products/pubs/pubd/hestats/obese/obse99.htm>, (2007), 3 pgs.

"NDI: The Aurora Electromagnetic Measurement System", [online]. © 2007 Northern Digital Inc. [retrieved Jul. 16, 2007]. Retrieved from the Internet: <URL: http://www.ndigital.com/medical/aurora.php>, 1 pg.

"noDNA—Sensoric Systems", [online]. [retrieved Jul. 16, 2007]. Retrieved from the Internet: <URL: http://www.nodna.com/index.php?id=7&L=1>, 1 pg.

"Noraxon—Manufacturers of Professional Surface Electromyography Products", [online]. [retrieved Jul. 16, 2007]. Retrieved from the Internet: <URL: http://www.noraxon.com/index.php3>, 1 pg.

"PA-06-055: Bioengineering Approaches to Energy Balance and Obesity", [online]. [retrieved Mar. 28, 2008]. Retrieved from the Internet: <URL: http://grants.nih.gov/grants/guide/pa-files/PA-06-055.html>, 22 pgs.

"PhaseSpace Inc. / Optical Motion Capture", [online]. [retrieved Jul. 16, 2007]. Retrieved from the Internet: <URL: http://www.phasespace.com/hardware.html>, 2 pgs.

"Qualisy Motion Capture", [online]. [retrieved Mar. 31, 2008]. Retrieved from the Internet: <URL: http://www.qualisys.com/templates/Q01.asp?sida=34>, 1 pg.

"Vicon / Products—Cameras", [online]. [retrieved Jul. 16, 2007]. Retrieved via the Internet: <URL: http://www.vicon.com/products/cameras.html>, 1 pg.

"Vista Medical—Store", [online]. [retrieved Jul. 16, 2007]. Retrieved from the Internet: <URL: http://www.pressuremapping.com/index.cfm?pageID=13&section=9>, 1 pg.

"VivoMetrics®—Sports & Fitness—Product Line", [online]. © 2007 VivoMetrics. [retrieved Jul. 16, 2007]. Retrieved from the Internet: <URL: http://www.vivometrics.com/sport/view_our_products/product_line.php>, 2 pgs.

"Xsen Motion Technologies—Moven-Inertial Motion Capturing", [online}. © 2007 Xsens Motion Technologies. [archived Jul. 17, 2007]. Retrieved from the Internet: <URL: http://web.archive.org/web/20070717123324/www.xsens.com/index.php?mainmenu=products&submenu=human_motion&subsubmenu=Moven>, 2 pgs.

Deyo, R. A., et al., "Back Pain Prevalence and Visit Rates: Estimates From U.S. National Surveys, 2002", [online]. [retrieved Mar. 28, 2008]. Retrieved from the Internet: <URL: http://ovidsp.tx.ovid.com.floyd.lib.umn.edu/spa/ovidweb.cgi>, 5 pgs.

Gibbs, P. T., et al., "Wearable Conductive Fiber Sensors for Multi-Axis Human Joint Angle Measurements", [online]. [retrieved Jul. 16, 2007]. Retrieved from the Internet: <URL: http://www.pubmedcentral.nih.gov/articlerender.fcgi?artid=555561>, 15 pgs.

Huddleston, J., et al., "Ambulatory Measurement of Knee Motion and Physical Activity: Preliminary Evaluation of a Smart Activity Monitor", [online]. [retrieved Mar. 28, 2008]. Retrieved from the Internet: <URL: http://www.jneuroengrehab.com/content/3/1/21>, 6 pgs.

Advanced Motion Measurement, 2014—Advanced Motion Measurement, 2014, Phoenix, Arizona. http://www.amm3d.com/.

Animazoo, 2004—Animazoo 3D Motion Capture Equipment: Gypsy Products from Animazoo, [online]. © 2004 Animazoo. [retrieved Jul. 16, 2007]. Retrieved from the Internet: <URL: http://www.animazoo.com/oroducts/index.htm>, 1 PQ.

Ascension, 2007—Ascension Products. Flock of Birds®, [online]. [retrieved Jul. 16, 2007]. Retrieved from the Internet: <URL: http://www.ascension-tech.com/products/flockofbirds.php>, 2 pgs.

Biometrics, 2007 Biometrics Ltd Research. Goniometers and Torsiometers, [online]. [retrieved Jul. 16, 2007]. Retrieved: htto:// www.biometricsltd.com/v%20oonio.htm>, 2 pgs.

Biopac, 2007—Biopac—TSD130A I Twin Axis Goniometer, 110mm, [online]. [retrieved Jul. 16, 2007]. Retrieved from the Internet: <URL: http://www.biopac.com/ Research.asp?Pid=3695 &Main=Transducers>, 1 pg.

Charndyn, 2007—Codamotion Products—Hardware and Software, [online]. [retrieved Jul. 16, 2007]. Retrieved from the Internet: <URL: http://www.charndyn.com/Products/ Products lntro.html>, 1 pg.

Deyo, R. A., et al., 2006, "Back Pain Prevalence and Visit Rates: Estimates From U.S. National Surveys, 2002", Spine, Nov. 2006, 31923), 2724-2727. [Mar. 28, 2008]. <URL: http://ovidsp.tx.ovid.com.floyd.lib.umn.edu/spa/>, 5 pgs.

Gibbs, P. T., and Asada, "Wearable Conductive Fiber Sensors for Multi-Axis Human Joint Angle Measurements", Journal of NeuroEngineering and Rehabilitation, Mar. 2, 2005, 2(7), 7-25. [Jul. 16, 2007]. <URL: http://www.pubmedcentral.nih.gov/ articlerender.fcgi?artid=555561>, 15 pgs.

Greenleaf, 2007—Greenleaf Products, [online]. [retrieved Jul. 16, 2007]. Retrieved from the Internet: <URL: http://www.oreanleafmed.com/products.htm>, 1 pg.

Huddleston et al., "Ambulatory Measurement of Knee Motion and Physical Activity: Preliminary Evaluation of a Smart Activity Monitor", Journal of NeuroEngineering and Rehab, 2006; 1(3), 21. [Mar. 28, 2008]. <URL: http://www.jneuroengrehab.com/content/3/1/21>, 6 pgs.

(56) References Cited

OTHER PUBLICATIONS

Immersion, 2007—Immersion Corporation. 3D Interaction, [online]. © 2007 Immersion Corporation. [retrieved Jul. 16, 2007]. Retrieved from the Internet: <URL: http://www.immersion.com/3d/>, 1 oo.

Lim et al., 2010—Lim et al., 2010, "A Low Cost Wearable Wireless Sensing System for Upper Limb Home Rehabilitation," Robotics Automation and Mechatronics (RAM), 2010 IEEE Conf, Jun. 28-30, 2010, 1-8, ISBN:978-1-4244-6503-3.

Measurand, 2007—Measurand. Motion Capture for the Classroom, [online]. [retrieved Jul. 16, 2007]. Retrieved from the Internet: <URL: http://www.measurand.com>, 1 pg.

Metamotion, 2007—Meta Motion. Motion Capture Hardware. Face Trackers, 2006 Meta Motion. [ret. Jul. 16, 2007]. <URL: http://www.metamotion.com/hardware/motion-capture-hardware.htm>, 1 pg.—http://www.metamotion.com/motion-capture/magnetic-motion-capture-1.htm.

Microstrain, 2007—MicroStrain® Inclinometers: Orientation Sensors, [online]. [retrieved Jul. 16, 2007]. Retrieved from the Internet: <URL: http://www.microstrain.com/ inclinometers.as_px1_pg.

Mikomak, 2007—Mikromak Service Brinkmann. Human Motion, [online]. © Mikromak Service Brinkmann. [retrieved Jul. 16, 2007]. Retrieved from the Internet: http://www.mikromak.com/en/en mensch! beweg.htm>, 1 pg.

Minisun, 2007—MiniSun. IDEEA Information, [online]. © MiniSun 2000-2007. [retrieved Jul. 16, 2007]. Retrieved from Internet: <URL: http://www.minisun.com/ ideea.asp>, 1 pg.

Motek, 2007—Motek Medical, [online]. [archived Jul. 8, 2007]. Retrieved from the Internet: <URL: http://web.archive.org/web/20070708132130/http:1/www.e- motek.com/medical/index.htm> 2 pgs.

Motion Analysis, 2007—MotionAnalysis—Movement Analysis Products, [online]. © 2007 Motion Analysis Corporation. [retrieved Jul. 16, 2007]. Retrieved from the Internet: <URL: http://www.motionanalysis.com/applications/movement1 movementproducts.html>, 1 pg.

Motion Lab, 2007—Motion Lab Systems, Inc., [online]. © 1995-2007 Motion Lab Systems, Inc. [retrieved Jul. 16, 2007]. Retrieved via the Internet: <URL: http://www.emgsrus.com>, 2 pgs.

Motionwerx, 2010—http://www.motionwerx.com, Motionwerx. Motionwerx produces the Gypsy 7.

noDNA, 2007—noDNA. Sensoric Systems, [online]. [retrieved Jul. 16, 2007]. Retrieved from the Internet: <URL: http://www.nodna.com/index.Q_hp?id=7&L=1>, 1 pg.

Noraxon, 2007—Noraxon. Manufacturers of Professional Surface Electromyography Products, [online]. [retrieved Jul. 16, 2007]. Retrieved from Internet: <URL: http://www.noraxon.com/index.php3>, 1 pg.

Northern Digital, 2007—NDI: The Aurora Electromagnetic Measurement System, [online]. © 2007 Northern Digital Inc. [retrieved Jul. 16, 2007]. Retrieved from the Internet: <URL: http://www.ndigital.com/medical/aurora.php>, 1 pg.

Phase Space, 2007—PhaseSpace Inc. / Optical Motion Capture, [online]. [retrieved Jul. 16, 2007]. Retrieved from the Internet: <URL: http://www.phasespace.com/ hardware.html>, 2 pgs.

Phoenix Technologies, 2007—High Performance Real-Time 3D Motion Capture Systems for Professionals, [online]. © 1997-2007 Phoenix Technologies Inc. [retrieved Jul. 16, 2007]. Retrieved from the Internet: <URL: http://www.ptiphoenix.com/Products.php>, 1 pg.

Polhemus, 2007—Liberty™ Latus™ Wireless Motion Tracking System from Polhemus, [online]. [retrieved Jul. 16, 2007]. Retrieved from the Internet: <URL:. http://www.polhemus.com/?page=Motion Liberty Latus>, 2 pgs.

Qualisys, 2008—Qualisys Motion Capture, [online]. [retrieved Mar. 31, 2008]. Retrieved from the Internet: <URL: http://www.qualisys.com/tem_Qiates/Q01.asQ_?sida=34>, 1 pg.

Vicon, 2007—Vicon I Products—Cameras, [online]. [retrieved Jul. 16, 2007]. Retrieved via the Internet: <URL: http://www.vicon.com/products/cameras.html>, 1 pg.

Vista Medical, 2007—Vista Medical—Store, [online]. [retrieved Jul. 16, 2007]. Retrieved from the Internet: <URL: http://www.pressuremapping.com/ index.cfm?pageiD=13&section=9>, 1 pg.

Vivometrics, 2007—VivoMetrics® Sports & Fitness Product Line, [online]. © 2007 VivoMetrics. [retrieved Jul. 16, 2007]. Retrieved from the Internet: <URL: http://www.vivometrics.com/s_Q_ort/view our products/product line.php>, 2 pgs.

Xsens, 2007—Xsens Motion Technologies—Maven-Inertial Motion Capturing, [online}. © 2007 Xsens Motion Technologies. [archived Jul. 17, 2007]. Retrieved from Internet: <URL: http:1/web.archive.org/web/20070717123324/ www.xsens.com/index.php?mainmenu=products&submenu=human_motion⊂ submenu=Moven>, 2 pgs.

* cited by examiner

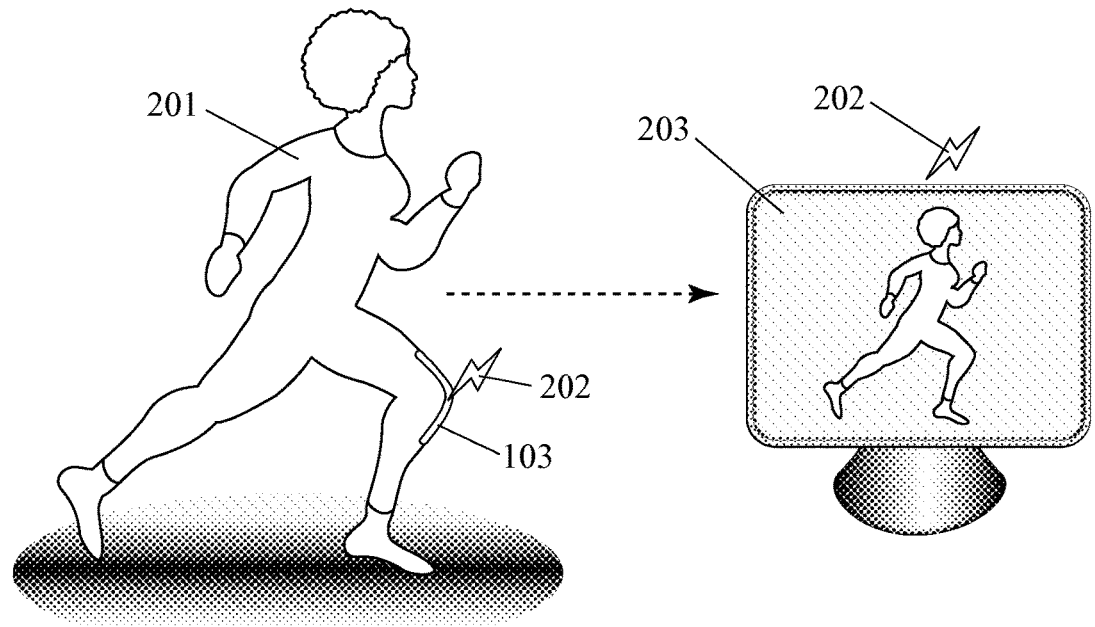
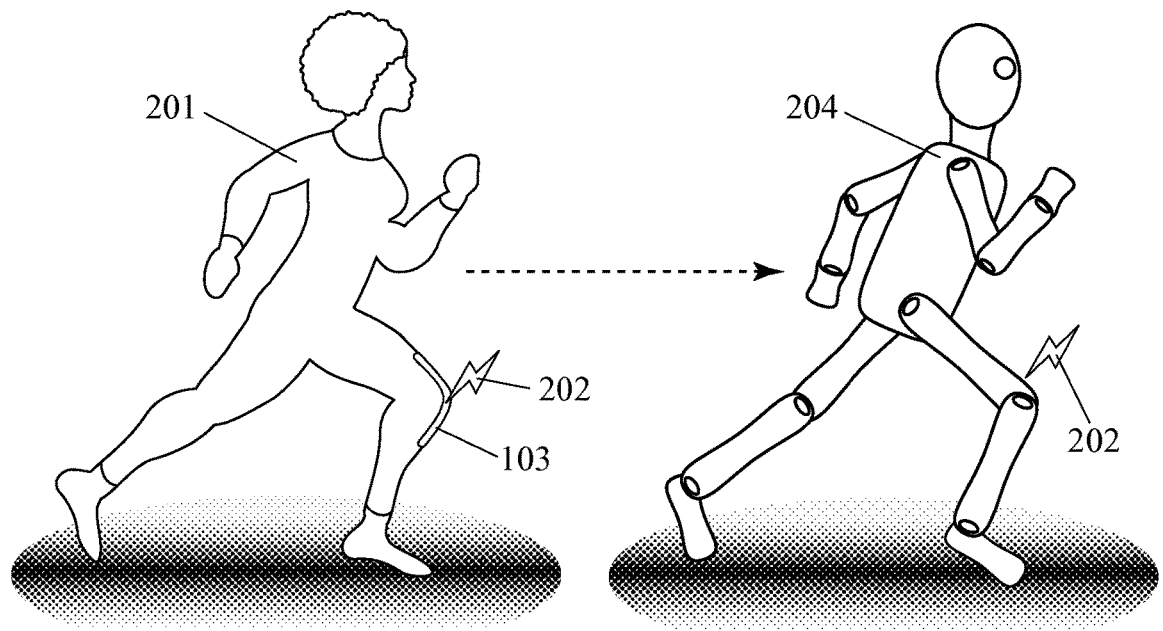
Fig. 2

Motion Recognition Clothing™
Design Parameters for Device Embodiment

A device for recognizing human motion comprising:

301 — an article of clothing or wearable accessory that spans at least one body joint; (type of article of clothing or accessory? type and construction of fabric or material? fit, tightness, and/or elasticity? spanning one joint or multiple joints?)

302 — at least one tube or channel attached to or integrated into the wearable article; (method of attaching and/or integrating the tube and wearable article? single tube spanning a joint or array of multiple tubes spanning a joint? tube material type, flexibility, durometer, and/or composite structure? tube cross-sectional inner area size, wall thickness, and shape? tube longitudinal length, shape, and/or non-uniform configuration? angle of tube spanning longitudinal joint axis? number of tubes and radial locations of tube in array? separate tubes or inter-connected tubes [lattice or mesh] in array? different tube types [see above factors] in array? removable to wash article or washable?)

303 — a flowable substance within the tube or channel; (liquid or gas substance? substance density and/or viscosity? baseline substance pressure? refillable to calibrate pressure?)

304 — at least one pressure sensor in communication with the flowable substance; (type of pressure sensor? pressure range? sensor location with respect to tube, article, and/or joint? one sensor per tube, multiple sensors per tube, or multiple tubes per sensor? removable to wash article or washable?)

305 — a data transmitter and/or data processor that receives signals from the pressure sensor, wherein these signals are used to estimate the angle of at least one body joint. (data transmission and/or data processing? location of data transmitter and/or data processor? removable to wash article or washable? analytic method to estimate joint angle(s) from tube pressure(s)? single angle for hinge joint and/or multiple angles for other joint types? multivariate analysis of pressure from multiple tubes? Fourier analysis of repeated pressure patterns? calibration method? other sensors like a thermometer and/or altimeter?)

Fig. 3

Motion Recognition Clothing™
Design Parameters for Method Embodiment

A method for recognizing human motion comprising:

401 — creating an article of clothing or wearable accessory spanning at least one body joint; (type of article of clothing or accessory? type and construction of fabric or material? fit, tightness, and/or elasticity? spanning one joint or multiple joints?)

402 — attaching or integrating at least one tube or channel and the wearable article; (method of attaching and/or integrating the tube and wearable article? single tube spanning a joint or array of multiple tubes spanning a joint? tube material type, flexibility, durometer, and/or composite structure? tube cross-sectional inner area size, wall thickness, and shape? tube longitudinal length, shape, and/or non-uniform configuration? angle of tube spanning longitudinal joint axis? number of tubes and radial locations of tube in array? separate tubes or inter-connected tubes [lattice or mesh] in array? different tube types [see above factors] in array? removable to wash article or washable?)

403 — filling the tube or channel with a flowable substance; (liquid or gas substance? substance density and/or viscosity? baseline substance pressure? refillable to calibrate pressure?)

404 — placing at least one pressure sensor in communication with the flowable substance; (type of pressure sensor? pressure range? sensor location with respect to tube, article, and/or joint? one sensor per tube, multiple sensors per tube, or multiple tubes per sensor? removable to wash article or washable?)

405 — receiving pressure signals from the pressure sensor in a data processing unit, wherein these signals are used to estimate the angle of at least one body joint. (data transmission and/or data processing? location of data transmitter and/or data processor? removable to wash article or washable? analytic method to estimate joint angle(s) from tube pressure(s)? single angle for hinge joint and/or multiple angles for other joint types? multivariate analysis of pressure from multiple tubes? Fourier analysis of repeated pressure patterns? calibration method? other sensors like a thermometer and/or altimeter?)

Fig. 4

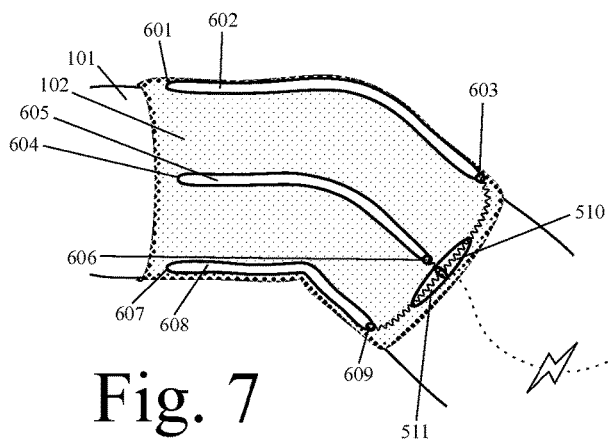
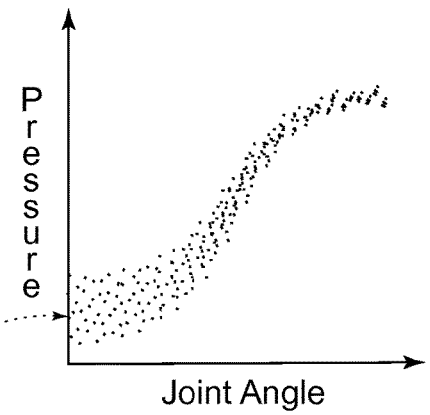
Fig. 7
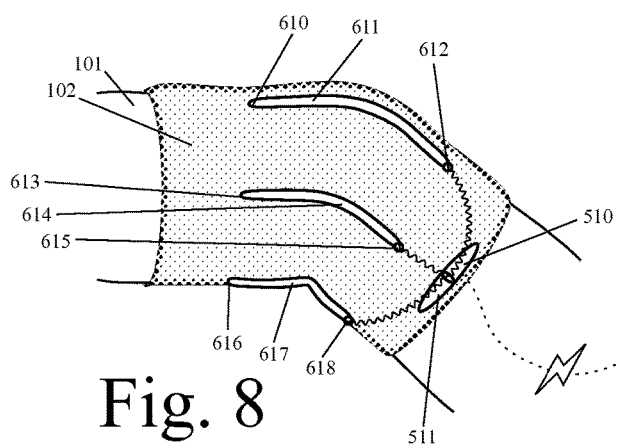
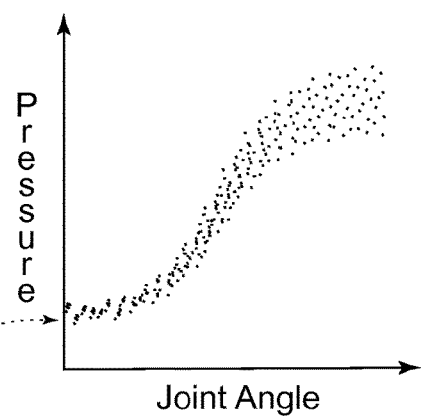
Fig. 8
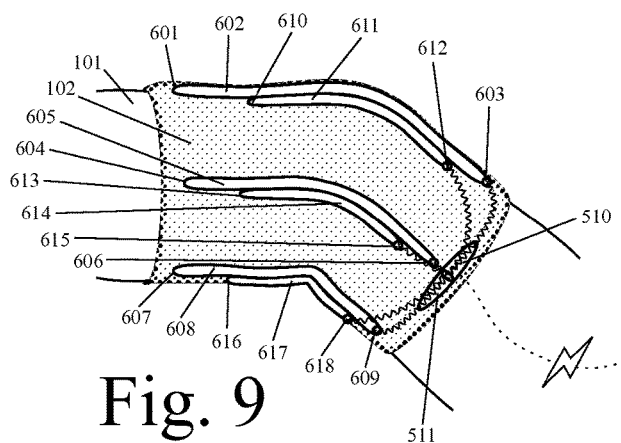
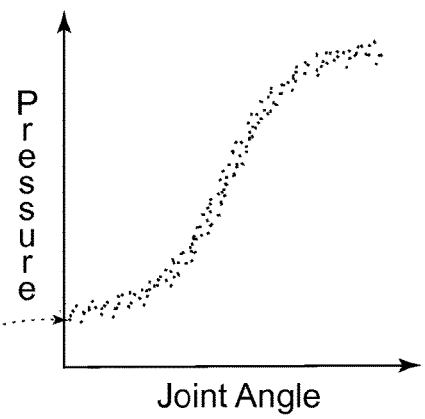
Fig. 9

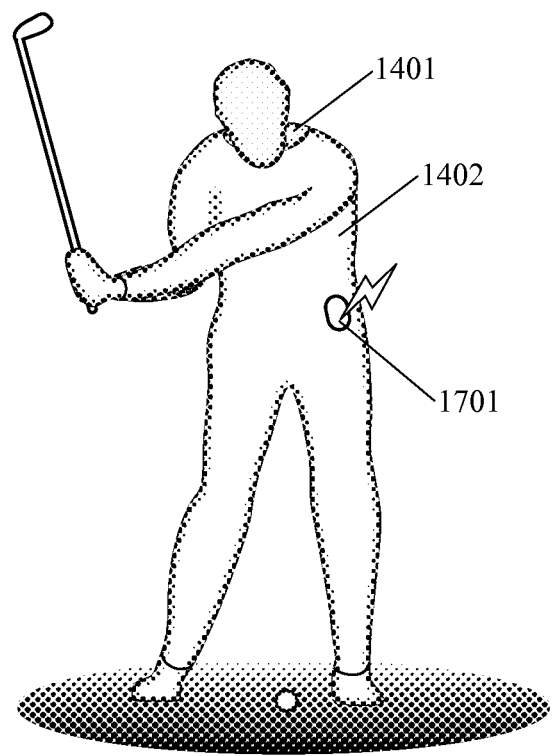
Fig. 17
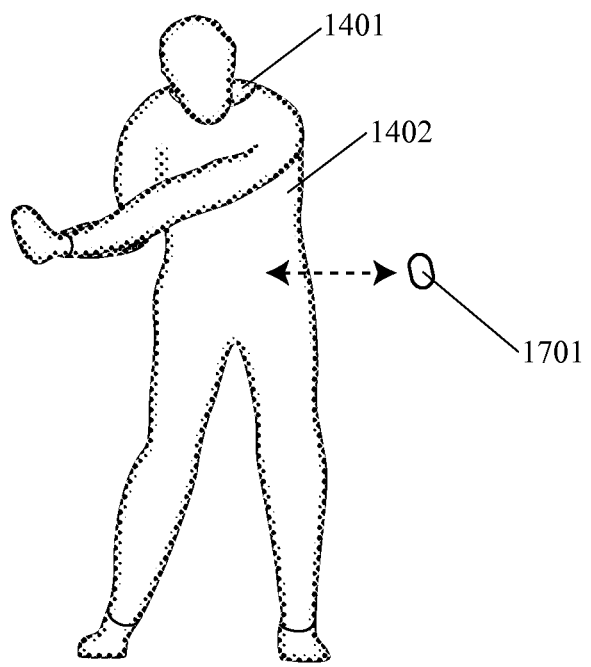

MOTION RECOGNITION CLOTHING (TM) WITH TWO DIFFERENT SETS OF TUBES SPANNING A BODY JOINT

CROSS-REFERENCE TO RELATED APPLICATIONS

This patent application claims the priority benefit of U.S. Provisional Patent Application No. 61/878,893 entitled "Motion Recognition Clothing™ with Two Different Sets of Tubes Spanning a Body Joint" filed on Sep. 17, 2013, the entire contents of which is incorporated herein by reference.

FEDERALLY SPONSORED RESEARCH

Not Applicable

SEQUENCE LISTING OR PROGRAM

Not Applicable

BACKGROUND

Field of Invention

This invention relates to wearable devices to measure and capture human motion.

Review and Limitations of the Prior Art

The goal of this invention is the creation of Motion Recognition Clothing™ which comprises a wearable, mobile, reasonably-priced, and relatively-unobtrusive full-body motion-capture system which can be used in diverse environments. There are motion capture technologies in the prior art, but they all have significant limitations compared to this invention.

As an example of prior art technology, there are camera-based motion capture systems. Some of these camera-based motion capture systems are very complex, comprising a circle of multiple cameras which each track a moving individual from a different perspective. These multi-camera systems can be accurate, but they also constrain a person to a space comprising the intersection of the fields of vision of these cameras. In addition to being relatively immobile, these multi-camera systems can also be relatively expensive.

There are simpler, single-camera motion capture systems which are designed for home use. Some relatively-simple and reasonably-priced single-camera systems are used for home computer gaming, exercise routines, and other applications. However, these single-camera motion capture systems also restrict a person to remain in the field of vision of the camera. They are not mobile for outdoor activities such as golf or running or swimming. Further, relying on one camera (or even two cameras which are close together) means that the system cannot track the locations of body members when the camera's direct line of sight to them is obscured by other body members or objects.

As another example of prior art technology, there are complex full-body portable motion capture suits comprising a relatively-large number of accelerometers, gyroscopes, and/or electrogoniometers. However, the more-accurate versions of such full-body motion capture suits tend to be relatively cumbersome and expensive. They can be great for motion capture for specialized purposes such as creating a video game or performance art, but are not well suited for contact sports or sports that involve extensive locational movement.

As another example of prior art technology, there is growing use of single-location accelerometer devices, such as wrist bands with accelerometers. These devices tend to be much less expensive and less intrusive than either the complex camera-based motion capture systems or the sophisticated full-body motion capture suits. They can perform adequately for measuring generalized "activity level", but they are not well-suited for capturing complex full-body motion such as that which occurs in sports like golf or gymnastics.

Due to the limitations of camera-based systems, cumbersome full-body motion capture suits, and single-location accelerometer devices in the prior art, there remains a need for a wearable, mobile, reasonably-priced, and relatively-unobtrusive full-body motion-capture system which can be used in diverse environments.

SUMMARY AND ADVANTAGES OF THIS INVENTION

This invention relates to clothing that can recognize full-body human motion. Motion Recognition Clothing™ as disclosed herein is a wearable device and method for recognizing human motion based on the pressure levels of a flowable substance within two different sets of flexible tubes or channels which are integrated into an article of clothing or wearable accessory and which span the same body joint. This technology can be used to create a wearable, mobile, reasonably-priced, and relatively-unobtrusive full-body motion-capture system which can be used in diverse environments.

Compared to camera-based motion capture systems, this invention can be mobile. It does not require a user to stay inside in front of a camera. It also does not suffer from optical occlusion. Compared to current full-body motion capture suits, this invention is less cumbersome, can be less fragile, and can be much less expensive. Compared to single-location wearable accelerometer devices, this invention can measure complex full-body motion, not just steps or a rough approximation of general "activity level."

There are numerous potential applications for Motion Recognition Clothing™ including: athletic performance measurement and improvement, athletic training, and virtual sports; computer gaming, virtual gaming, avatar animation, and virtual reality interaction; caloric expenditure monitoring, caloric intake monitoring, energy balance, exercise measurements, and virtual exercise; medical diagnosis, gait analysis, posture correction, injury avoidance, telemedicine, and telerobotics; teleconferencing and telepresence; and motion picture animation and performance arts.

Specifically, in an example Motion Recognition Clothing™ can be embodied in a device for recognizing human motion which comprises: an article of clothing or wearable accessory that is configured to span at least a portion of at least one body joint; at least one pressure sensor; at least one flowable substance; a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor; a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, and wherein one or more design characteristics are different for the second set than for the first set; and a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

In an example, these design characteristics can be selected from the group consisting of: the angle at which tubes or channels in a set cross or are parallel to the longitudinal axis of a joint when the joint is fully extended; the baseline flowable substance pressures in a set of tubes or channels when a joint is fully extended; the compressibility of tubes or channels in a set; the cross-sectional size of tubes or channels in a set; the cross-sectional curvature of tubes or channels in a set; the cross-sectional shape of tubes or channels in a set; the cross-sectional shape variation or uniformity of tubes or channels in a set; having separate or inter-connected tubes or channels such as a mesh or lattice in a set; the length of tubes or channels in a set; the locations of pressure sensors in tubes or channels in a set; the longitudinal curvature of tubes or channels in a set; segment of the longitudinal axis of a joint that is spanned by tubes or channels in a set; the type of flowable substance within tubes or channels in a set; the viscosity of a flowable substance in tubes or channels in a set; and the wall thickness of tubes or channels in a set.

Although considerable product development and empirical testing must still be done, Motion Recognition Clothing™ as disclosed herein has a number of potential advantages over different types of prior art for recognizing human motion. These potential advantages include:

Mobility—Motion Recognition Clothing™ does not confine a person to a particular room or location as is the case with popular fixed-location camera-based systems or more-expensive fixed-location multi-camera motion capture systems. Motion Recognition Clothing™ can be used virtually anywhere: golfing, jogging, playing team sports, hiking, skydiving, or even swimming. As prototypes are refined into commercial products, Motion Recognition Clothing™ may become sufficiently embedded into articles of clothing that it can be worn unobtrusively throughout the day. This can enable numerous beneficial applications including accurate estimation of total daily caloric expenditure.

No Occlusion—Motion Recognition Clothing™ does not require a direct line-of-sight to a camera and thus is not confounded if another person, an environmental object, or a moving body member occludes this line-of-sight. This makes Motion Recognition Clothing™ much better for applications, such as team sports or martial arts, in which two or more people interact. Motion Recognition Clothing™ can also be superior for applications involving complex motions (such as spinning or turning) in which some body members are obscured by other body members.

Full-Body Motion—Motion Recognition Clothing™ can measure virtually full-body human motion. Single-location devices that measure human motion using an accelerometer (such as pedometers, smart watches, and belt clip devices) can be useful for measure gross movement of a person's overall body, such as overall steps or gait when a person is walking or running. However, single-location devices based on an accelerometer can be blind to movement of one member of a person's body relative to another member than do not cause movement at the location where the device is worn. Motion Recognition Clothing™ can measure relative motion (and posture) of body members relative to each other in addition to gross movement of a person's overall body.

Freedom of Movement—Motion Recognition Clothing™ can enable more freedom of movement and be less cumbersome than exoskeleton devices with rigid or semi-rigid components. Unlike exoskeletons with rigid or semi-rigid components, Motion Recognition Clothing™ comprises flexible tubes or channels which are more organic and less-constraining than exoskeletal members. For example, although state-of-the-art exoskeleton systems can be very useful for measuring virtually full-body motion, most or all of them would likely interfere with the movements of an athlete during a game. Especially as Motion Recognition Clothing™ is refined into smaller tubes or channels, Motion Recognition Clothing™ can measure full-body human motion without interfering with the wearer's movements.

Less Visually-Intrusive—Motion Recognition Clothing™ can be less visually-intrusive than exoskeletal systems for measuring full-body human motion. Most exoskeletal systems comprise external rigid or semi-rigid members that stick out (inches) from the surface of a person's body. The result is an exoskeletal suit which is somewhat visually-intrusive and not the type of fashion statement that most people would want to make at work, during a soccer match, on a date, or during a trip to the grocery store. Although these early prototypes of Motion Recognition Clothing™ are somewhat peculiar looking as well, even early prototypes do not protrude out more than a fraction of an inch. With further refinement and smaller tubes or channels, a full-body suit for Motion Recognition Clothing™ can be much less visually intrusive than full-body devices in the prior art.

Durability—Motion Recognition Clothing™ can be more durable than motion recognition systems that use semi-rigid exoskeletons, fiber optics, electrically-conductive fibers, and/or gyroscopes. For example, while exoskeleton systems can work well for (non-interpersonal) dance applications and motion picture animation applications in which a wearer does not come into compressive contact with other people or external environmental objects, such systems would likely be damaged if a person were to wear one playing a contact sport such as football or engage in contact-based martial arts. The semi-rigid members and/or electrically conductive fibers could break. However, the flexible tubes or channels in Motion Recognition Clothing™ are designed to be compressed without breaking. Accordingly, Motion Recognition Clothing™ can be less fragile and more durable than other systems for full-body motion recognition, especially for applications involving contact with other people or environmental objects.

Small-Scale Motion—Camera-based systems for human motion recognition are getting better and better at recognizing large-scale skeletal movements (such as arms and legs moving during jumping jacks), but they still are not very good at recognizing small-scale body movements (such as fingers playing a guitar). In addition to accurately recognizing large-scale body motions, Motion Recognition Clothing™ can also be incorporated into articles of clothing or wearable accessories (such as gloves) that measure small-scale body motions. Also, as mentioned previously, Motion Recognition Clothing™ can be superior to camera-based systems for applications such as recognizing finger movements because Motion Recognition Clothing™ is not confounded by one finger visually obscuring another finger.

Waterproof—With self-contained tubes containing one or more pressure sensors, Motion Recognition Clothing™ can be waterproof and washable. Motion recognition systems that rely on electrically-conductive fibers and/or resistance-based hinges are likely to be more difficult, or even impossible, to make waterproof Camera-based systems are even less-likely to work for applications involving water (such as swimming) or wet/rainy conditions.

Independence from Ambient Light—Since it does not depend on light, Motion Recognition Clothing™ can operate regardless of ambient light conditions. Most camera-based systems do not work well in bright sunlight or in dim ambient light. Some camera-based systems can also be confounded if a person's skin color is similar to the color of clothing or if the color of clothing is similar to the color of environmental objects. With Motion Recognition Clothing™, the color of a person's skin, clothing, or surrounding environment does not make any difference.

Safety—Since the tubes or channels which span body joints in Motion Recognition Clothing™ are flexible and fluid, they are less likely to cause injury to the wearer upon contact with another person or environmental object than exoskeletons or other systems which have rigid or semi-rigid components spanning body joints. Also, with respect to full-body systems involving electrically conductive and/or resistive components, it is important to investigate the effects of long-term exposure to electromagnetic fields so close to the body. Although speculative at this time, it may be that pressure-based Motion Recognition Clothing (which is based on pressure levels in flexible tubes or channels) can be safer for long-term health than electricity-based motion recognition systems (in which electrical currents continually traverse the surface of a person's body).

There are numerous potential applications for Motion Recognition Clothing™ including: athletic performance measurement, athletic performance improvement, athletic training, and virtual sports; computer gaming, virtual gaming, avatar animation, and virtual reality interaction; caloric expenditure monitoring, caloric intake monitoring, energy balance, exercise measurements, and virtual exercise; medical diagnosis, gait analysis, posture correction, injury avoidance, telemedicine, and telerobotics; teleconferencing and telepresence; and motion picture animation and performance arts.

INTRODUCTION TO THE FIGURES

FIGS. 1 through 19 show examples of how this invention can be embodied in wearable devices and methods for recognizing human motion, but these examples do not limit the full generalizability of the claims.

FIG. 1 shows an example of three sequential views of a stretchable article that covers a person's knee and also the three associated graphs between body joint angle and the pressure of a flowable substance within a tube than spans the knee.

FIG. 2 shows examples of how a wearable device for recognizing human motion can be used to replicate human motion in a virtual object or in a physical object.

FIG. 3 outlines examples of wearable devices for recognizing human motion including variation in design parameters.

FIG. 4 outlines examples of methods for recognizing human motion including variation in design parameters.

Figure 5:
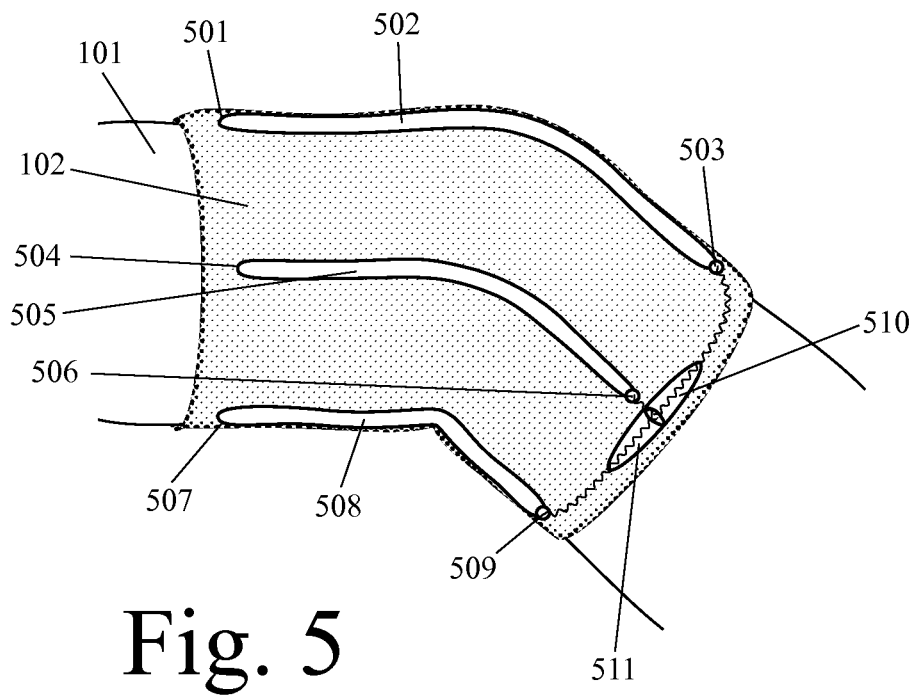

FIG. 5 shows an example of a wearable stretchable accessory that comprises parallel tubes which cross the circumference of a body joint at locations which are evenly distributed around the circumference of the body joint.

Figure 6:
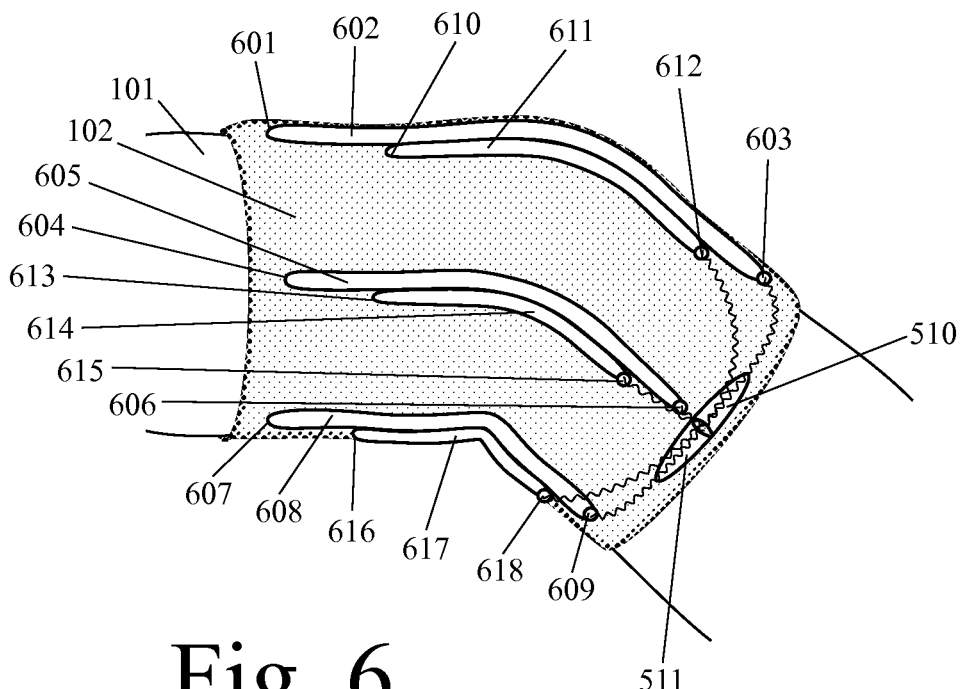

FIG. 6 shows an example of a wearable stretchable accessory with two sets of tubes or channels spanning the same joint, wherein these two sets differ in length.

FIGS. 7 through 9 show an example of how using pressure information from both a first set and a second set can enable more accurate estimation of body angle than using pressure information from either a first set alone or a second set alone.

Figure 10:
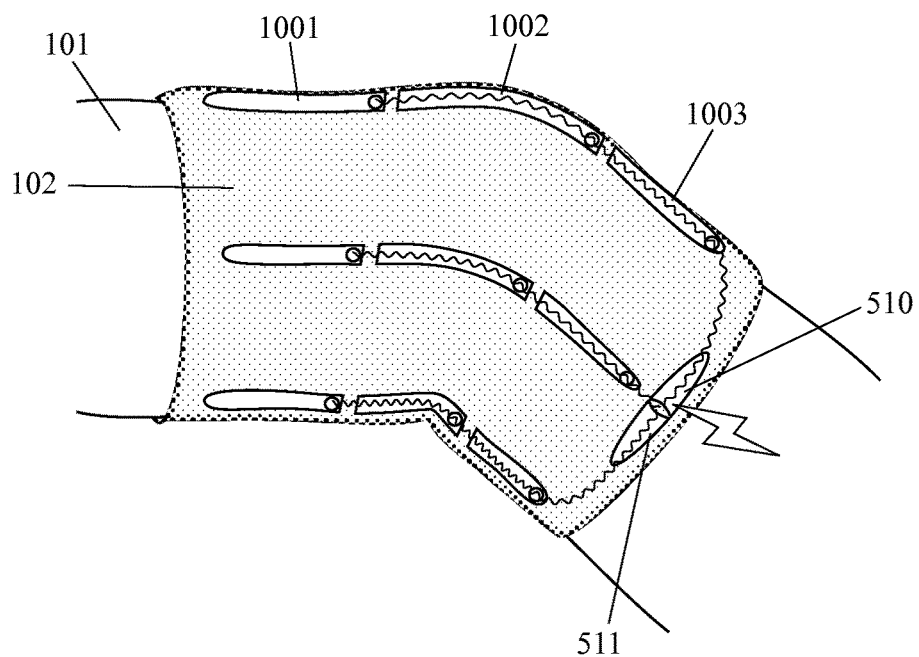

FIG. 10 shows an example in which different sets of tubes or channels span different segments of the longitudinal axis of a body joint.

Figure 11:
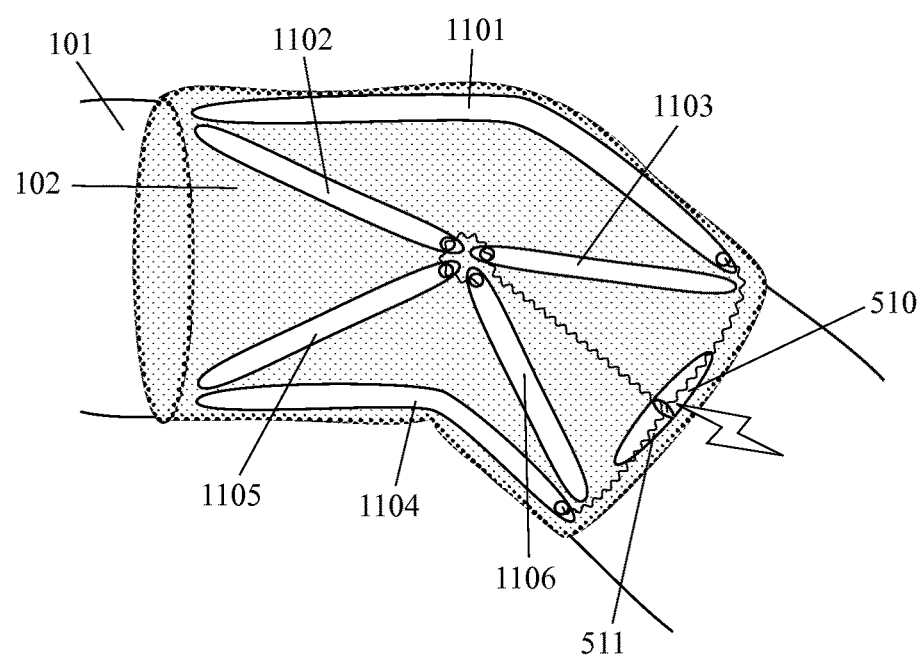

FIG. 11 shows an example in which different sets of tubes or channels span the same body joint at different angles with respect to the longitudinal axis of the joint.

Figure 12:
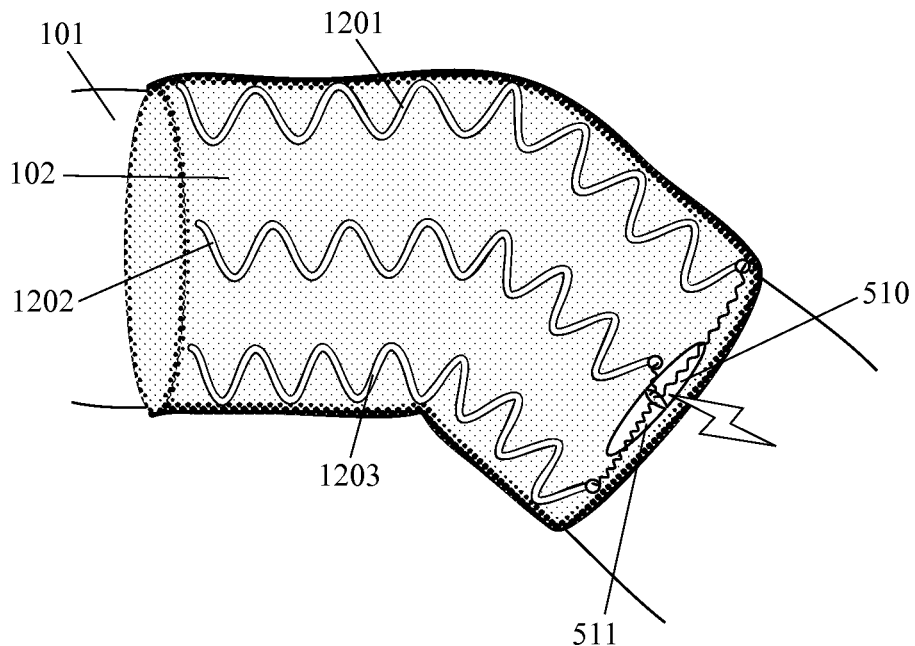

FIG. 12 shows an example in which tubes or channels span a body joint in a curvaceous, sinusoidal manner.

Figure 13:
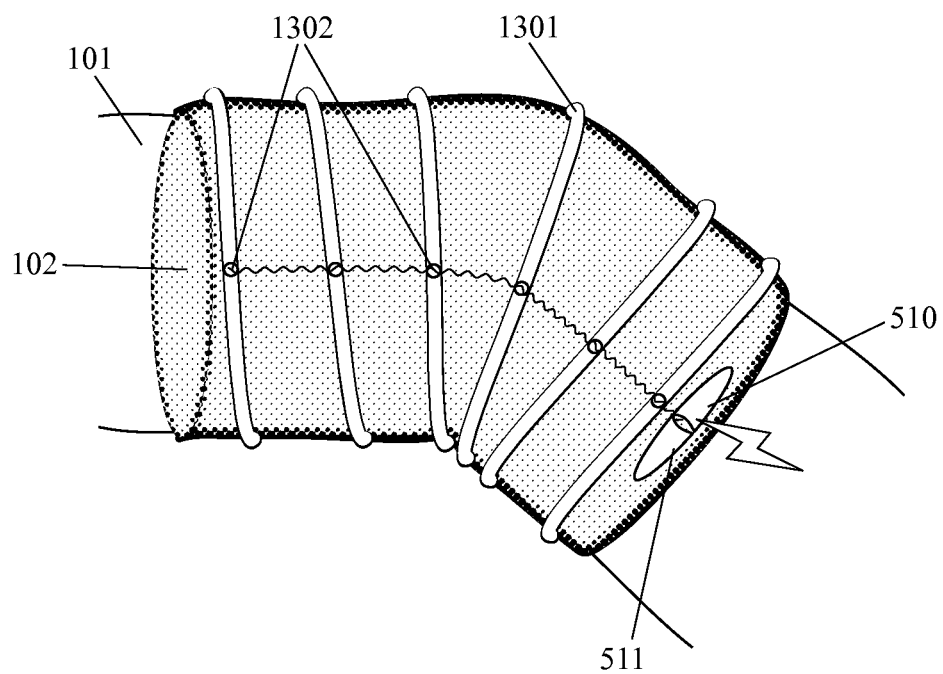

FIG. 13 shows an example in which a spiral tube or channel wraps around the circumference of a body joint.

Figure 14:
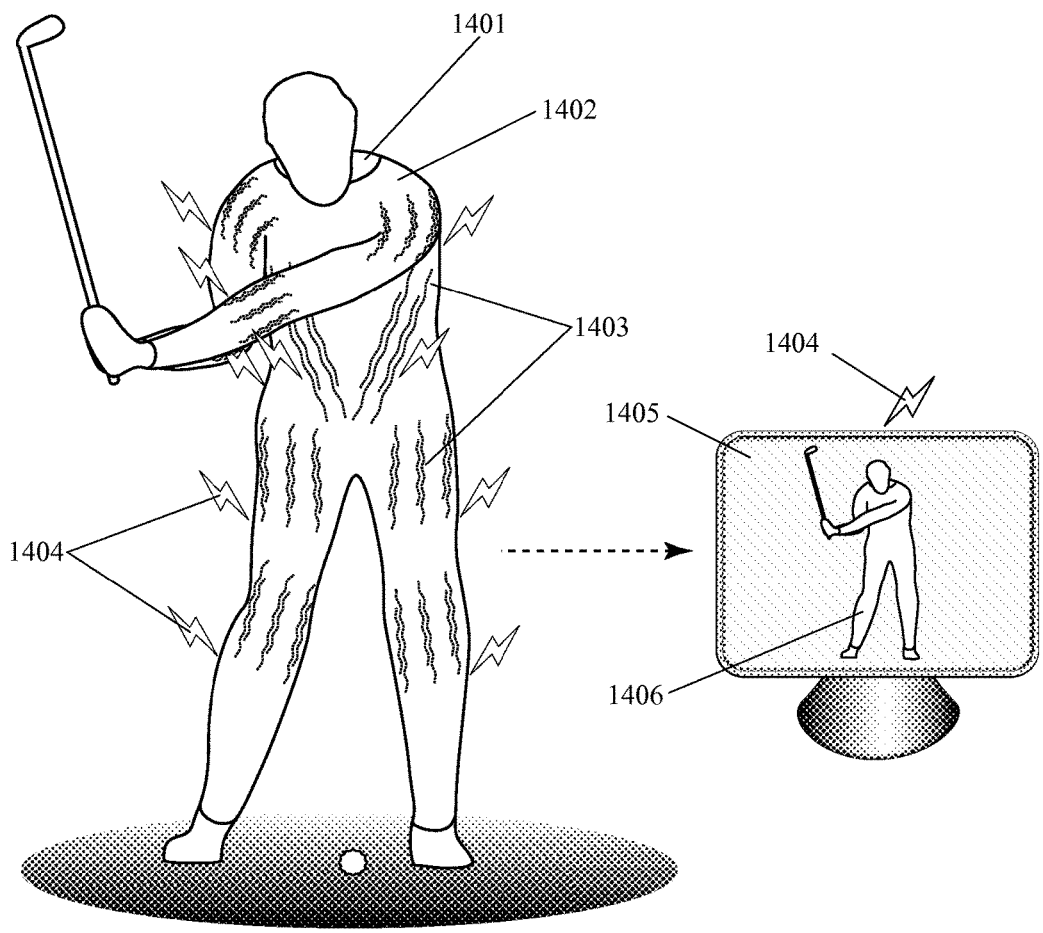

FIG. 14 shows an example of how a wearable device for measuring human motion can be used for sports training and/or virtually-interactive sports.

Figure 15:
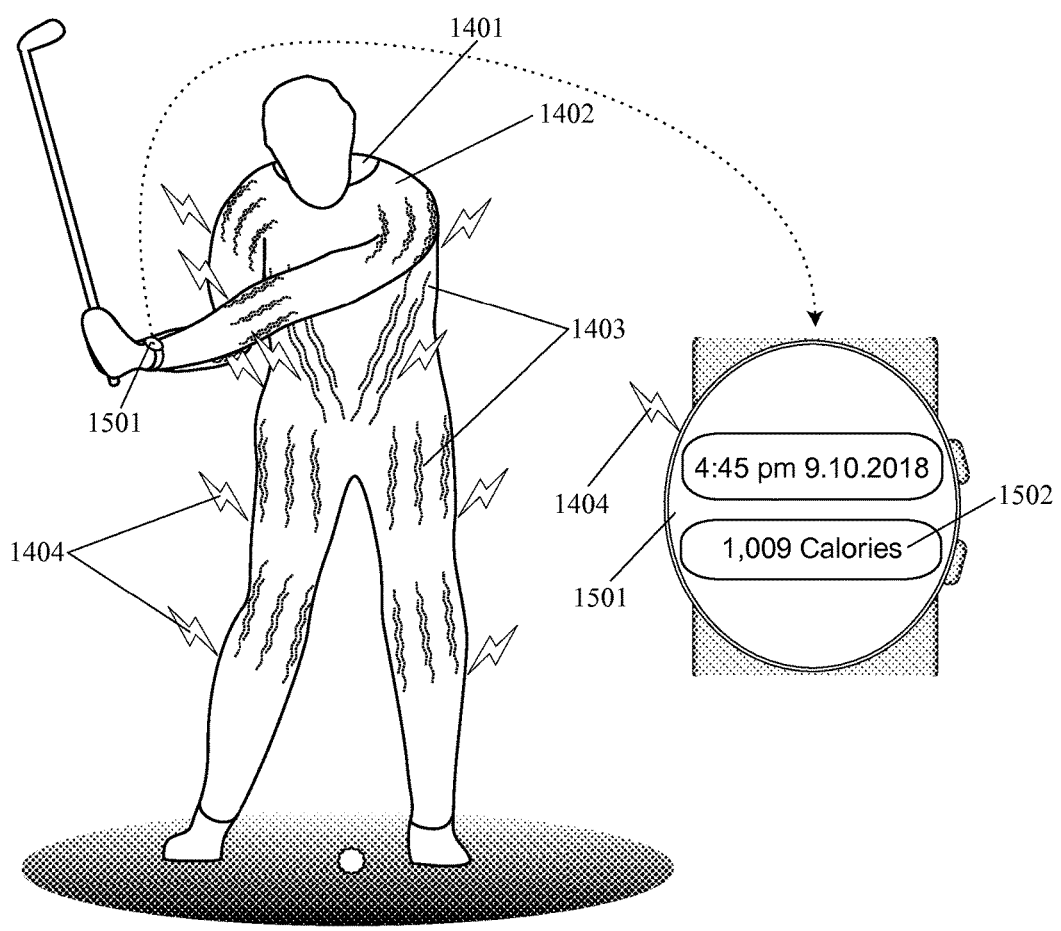

FIG. 15 shows an example of how a wearable device for recognizing full-body human motion can be used to track and display caloric expenditure.

Figure 16:
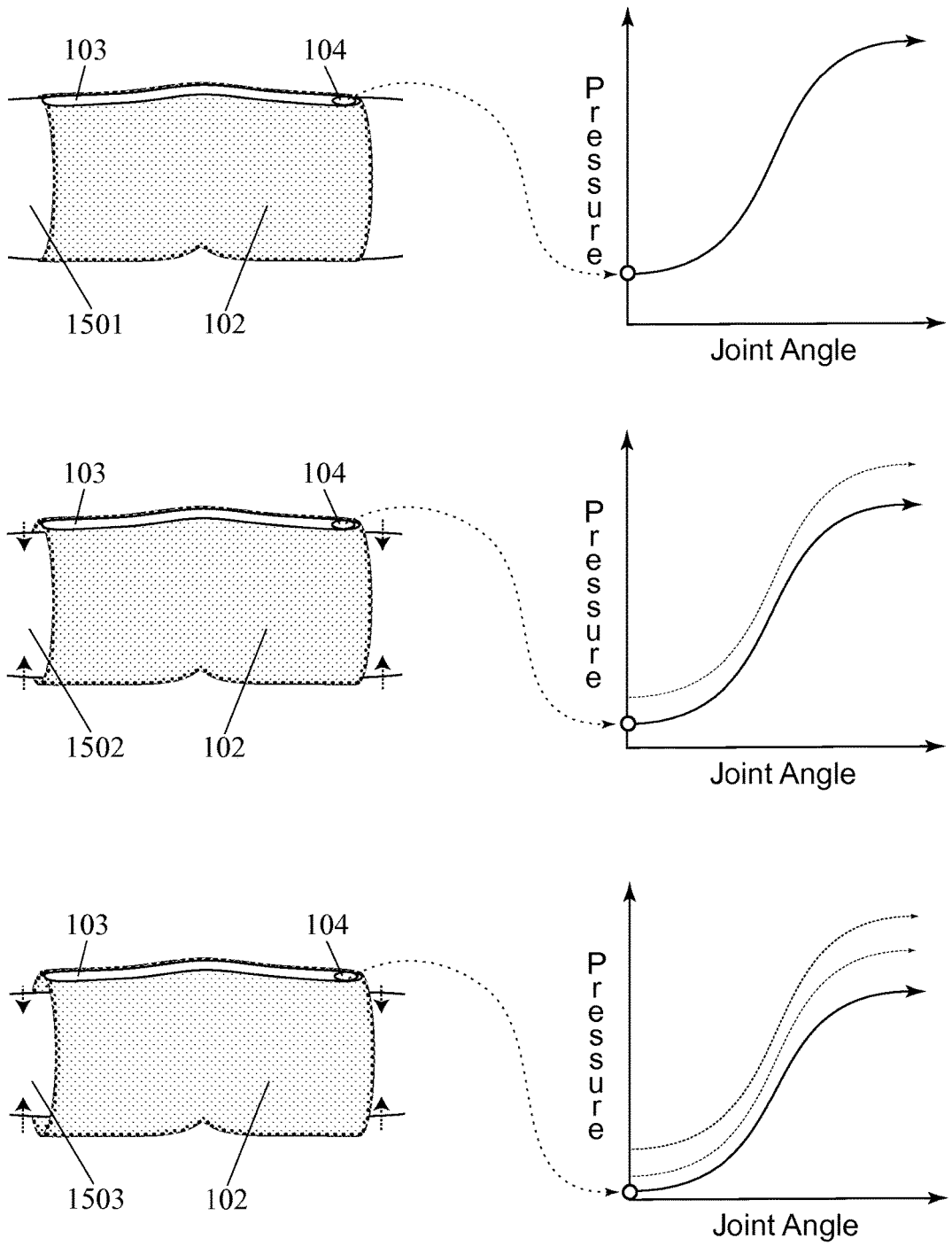

FIG. 16 shows examples of how the functional relationship between joint angle and substance pressure can change with changes in how tightly or loosely an article of clothing or wearable accessory fits over a body joint.

FIG. 17 shows an example wherein a central data transmitter can be removed so that an article of clothing or wearable accessory can be washed.

Figure 18:
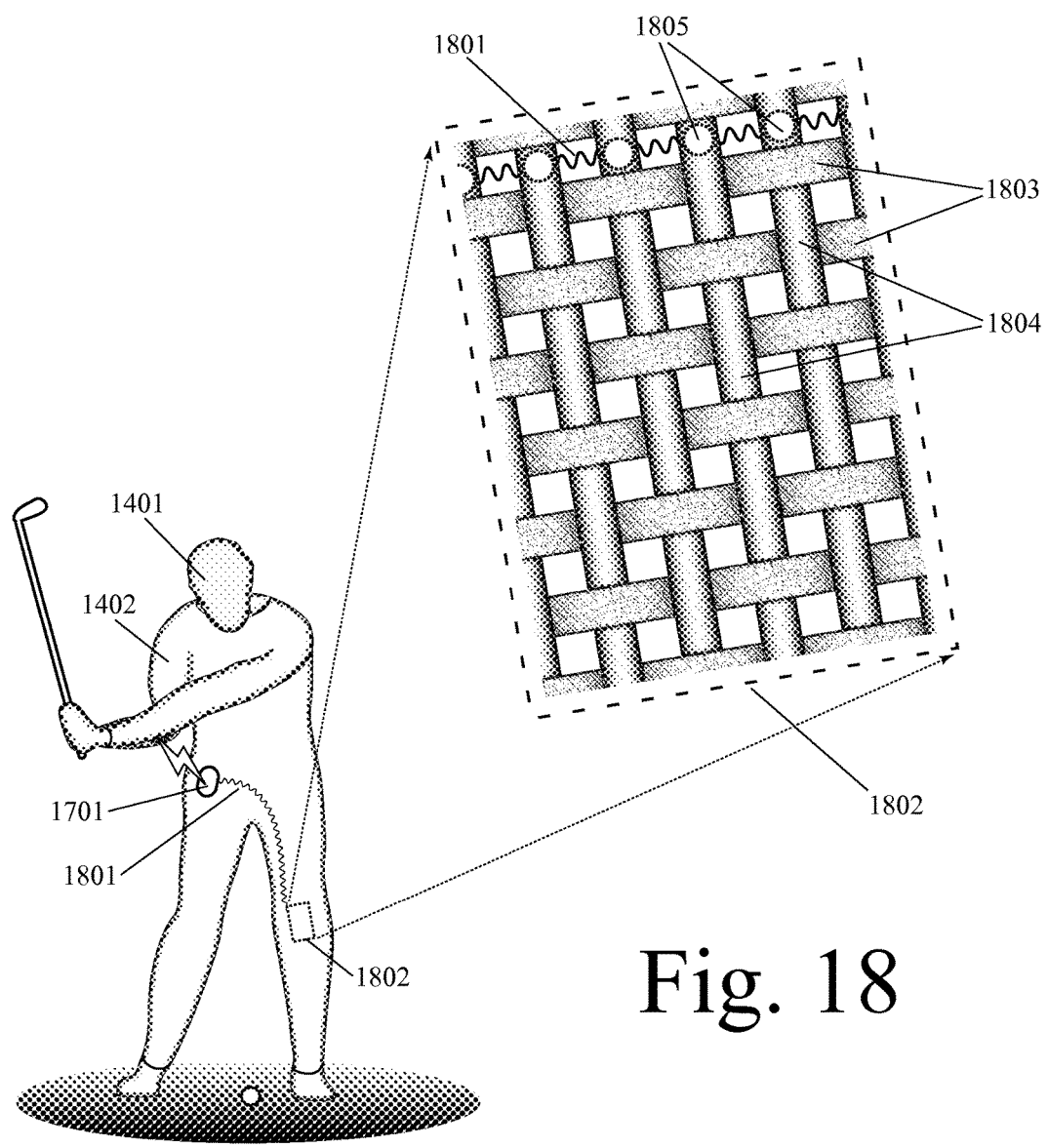

FIG. 18 shows an example of a wearable device for recognizing human motion in which multiple parallel tubes or channels containing a flowable substance are woven into the fabric of an article of clothing or wearable accessory.

Figure 19:
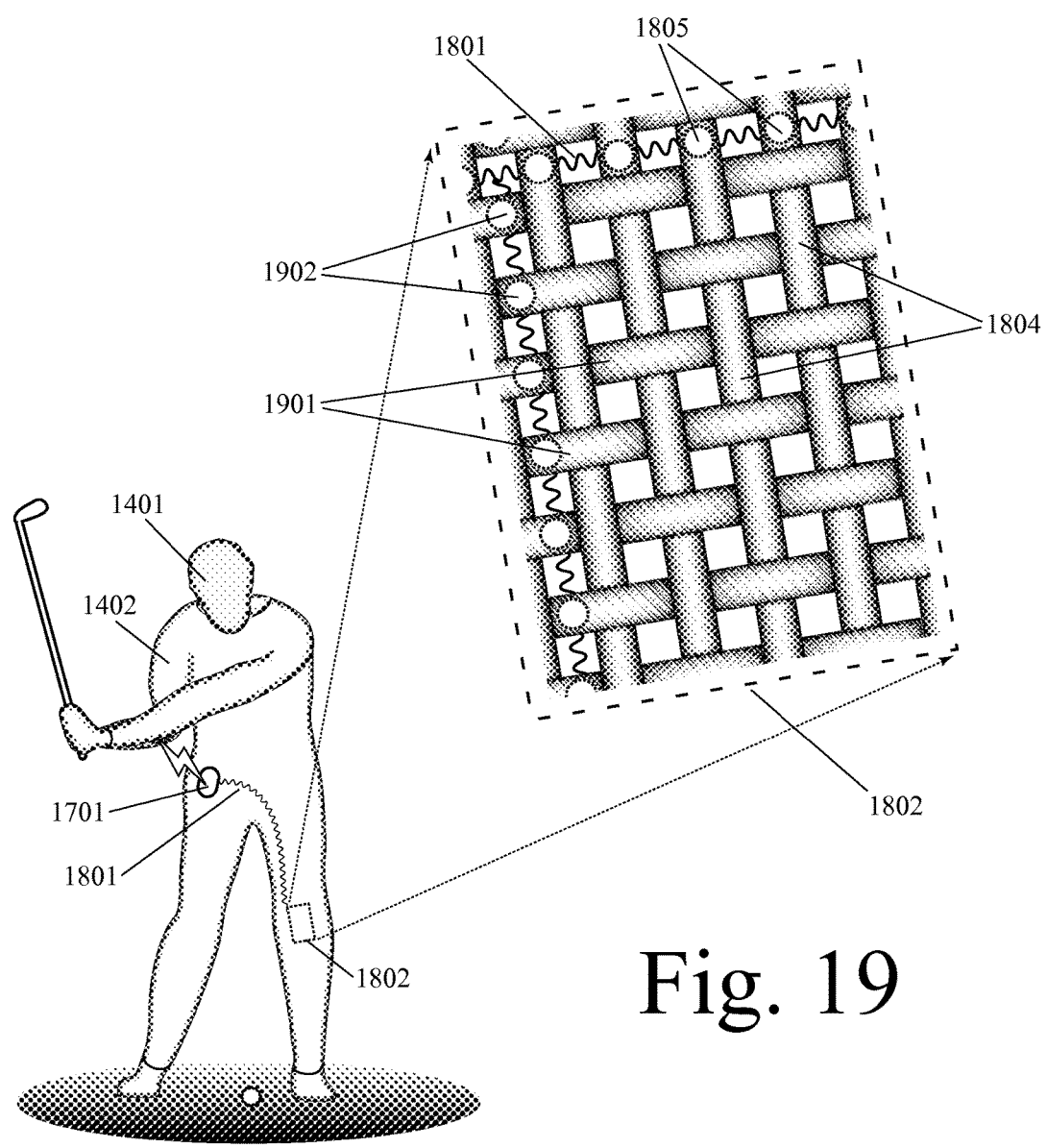

FIG. 19 shows an example of a wearable device for recognizing human motion in which tubes or channels span a body joint in both longitudinal and lateral directions.

DETAILED DESCRIPTION OF THE FIGURES

FIGS. 1 through 19 show examples of how this invention can be embodied in wearable devices and methods for recognizing human motion, but these examples do not limit the full generalizability of the claims.

Figure 1:
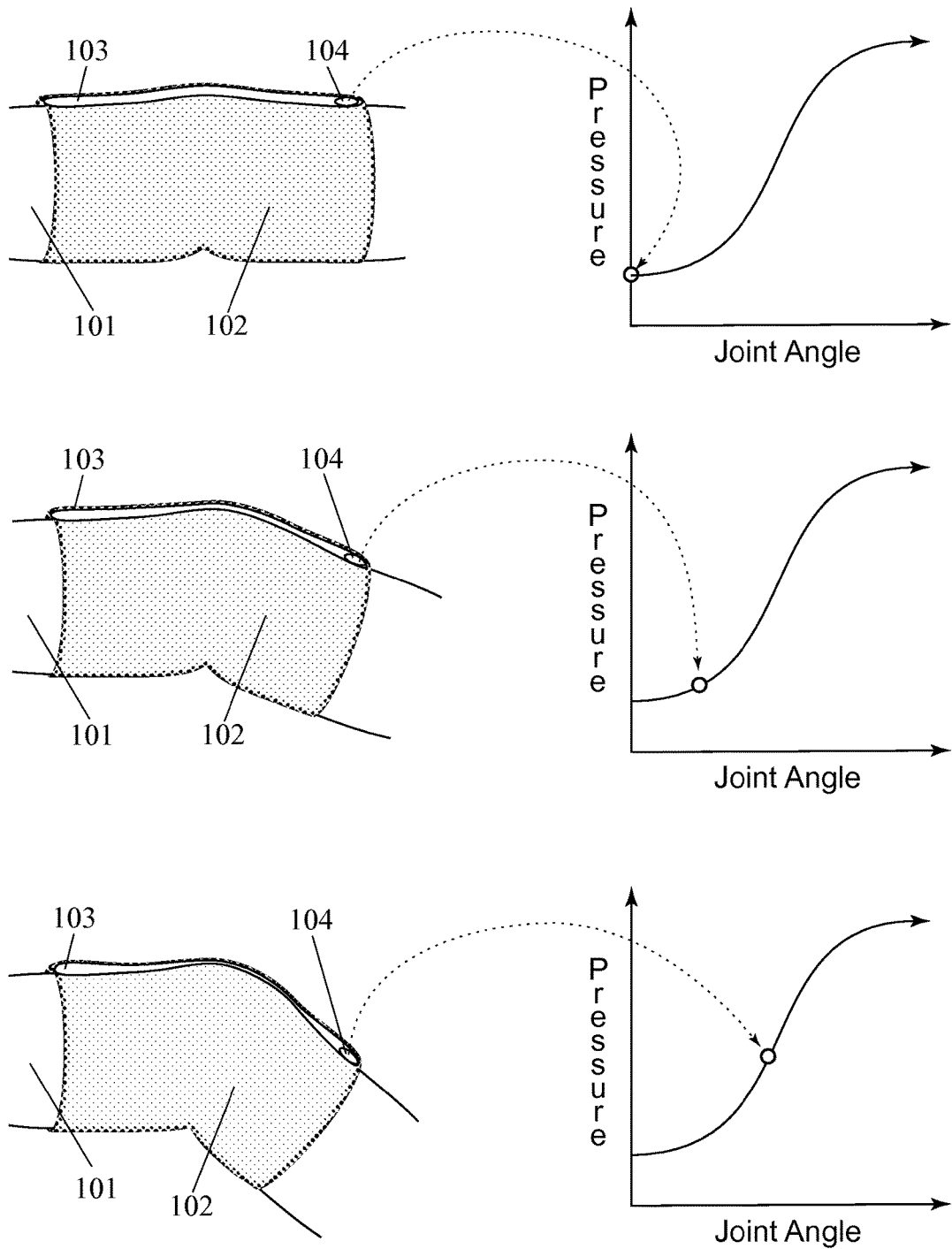

FIG. 1 shows an example of how this invention can be embodied in a wearable device for recognizing human motion. The upper, middle, and lower thirds of FIG. 1 show three sequential views of this example of a wearable device. In this example, the device is worn over a single body joint.

In this example, this joint is a knee. In an example, multiple such devices can be worn over different body joints.

The left sides of each of these sequential views (upper, middle, and lower) show an example of how the device can be physically embodied as a tubular and stretchable wearable article that covers a person's knee. The right sides of each of these three sequential views (upper, middle, and lower) show an example of a conceptual graph of the functional relationship between the angle of the body joint that is spanned by the device and the pressure of a flowable substance in a tube within this device.

In each of these three sequential views, there is a dotted line arrow that connects the physical device (on the left side) to the associated conceptual graph (on the right side). This dotted line arrow symbolically represents the transmission of data from the physical device to the associated functional relationship between variables. As the angle of the body joint changes in the physical embodiment of the device, the pressure level changes in the associated graph. There can be a measurable and predictable functional relationship between joint angle and pressure level in such a device. In an example, this functional relationship can be used in reverse to predict joint angle based on pressure level. In an example, pressure information from multiple devices of this sort which a person wears over multiple joints (perhaps supplemented by an accelerometer and/or GPS device) can be used to predict, model, and/or recognize the person's full-body configuration, posture, and/or motion.

In the example that is shown in FIG. 1, a wearable device for recognizing human motion comprises: an article of clothing or wearable accessory (102) that spans a body joint (101); a tube or channel (103) that is attached to or integrated into the article of clothing or wearable accessory, wherein this tube or channel contains a flowable substance; and a pressure sensor (104) that measures the pressure of the flowable substance inside the tube or channel.

In the example that is shown in FIG. 1, article of clothing or wearable accessory 102 is a relatively close-fitting, stretchable, and tubular wearable accessory whose circumference completely covers and spans a body joint. In an example, an article of clothing or wearable accessory can be less close-fitting. In an example, an article of clothing or wearable accessory can cover or span only a portion of a body joint. In this example, the flowable substance within the tube or channel is air. In an example, the flowable substance within a tube or channel can be a liquid, a gel, or a different type of gas. In an example, there can be multiple tubes spanning the same body joint.

In the example that is shown in FIG. 1, a single wearable device for recognizing human motion spans a single body joint. In an example, a single wearable device for recognizing human motion can span multiple body joints. In an example, a single article of clothing or wearable accessory that spans multiple joints can include different sets of tubes which span different joints. In an example, multiple wearable devices can span a single body joint. In an example, a system for recognizing human motion can comprise multiple devices that each span a different body joint, but which share electromagnetic, pneumatic, or hydraulic communication. In an example, multiple devices that comprise a system for measuring human motion can be in wireless communication with a common data transmitter and/or data processor. In various examples, one or more body joints spanned by such devices can be selected from the group consisting of: knee, elbow, hip, pelvis, shoulder, ankle, foot, toe, wrist, palm, finger, torso, rib cage, spine, neck, and jaw.

FIG. 1 shows three sequential views of how a wearable device for recognizing human motion can work as body joint 101 bends. The top third of FIG. 1 shows a first sequential view in which body joint 101 is fully extended. The middle third of FIG. 1 shows a second sequential view of the same device in which body joint 101 begins to bend. The bottom third of FIG. 1 shows a third sequential view of the same device in which body joint 101 bends further.

In this example, the conceptual graph of joint angle vs. pressure in the first sequential view (upper third of FIG. 1) shows the lowest value for pressure when body joint 101 is fully extended. In this example, joint angle is measured relative to the longitudinal axis of the upper member of the body joint, so the joint angle is 0 degrees when the joint is fully extended. The conceptual graph of joint angle vs. pressure in the second sequential view (middle third of FIG. 1) shows an increase in pressure when body joint 101 begins to bend. In this example, the joint angle of this initial bending is 20 degrees relative to the longitudinal axis of the upper member of the body joint. The conceptual graph of joint angle vs. pressure in the third sequential view (lower third of FIG. 1) shows a further increase in pressure when body joint 101 bends further. In this example, the joint angle of this further bending is 40 degrees relative to the longitudinal axis of the upper member of the body joint.

In this example, the body joint being modeled (a knee) is a hinge joint and movement of this joint is modeled by changes in a single angle. In this example, the functional relationship between joint angle and pressure is substantially a bivariate function. In another example, a body joint being modeled can be a ball-and-socket joint (or other type of non-hinge joint) and movement of the joint can be modeled by changes in multiple angles. In another example, the functional relationship between multiple angles of a body joint and the pressures of a flowable substance inside multiple tubes or channels can be a multivariate function. In this example, the functional relationship between joint angle and pressure is shown as being positive, monotonic, and non-linear. In an example, the functional relationship between joint angle and pressure can be estimated using a polynomial function.

In an example, during estimation of the functional relationship between joint angle and pressure level, joint angle acts as the independent variable and pressure level within a tube acts as the dependent variable. In an example, this functional relationship can be used in reverse to estimate joint angle based on pressure level. When used in reverse, pressure level can be viewed as the independent variable and (predicted) joint angle can be viewed as the dependent variable.

In this example, the pressure of a flowable substance within a tube changes relatively little as the body joint first starts to bend. Then the pressure changes more as the joint enters a mid-range of joint angles. Finally, the pressure changes relatively little as the joint approaches full contraction. In this example, the slope of the functional relationship between body joint angle and pressure level is relatively flat in the low-range of body joint angle, increases in the mid-range of body joint angle, and then becomes relatively flat again in the high-range of body joint angle. In an example, the functional relationship between joint angle and pressure can be most sensitive to changes in pressure in the mid-range of joint angle.

In various examples, different types and configurations of tubes can have different degrees of accuracy for estimating joint angle over different portions of the total range of motion for a body joint. In an example, a first tube type or configuration can be more accurate for estimating smaller joint angles, a second tube type or configuration can be more accurate for estimating mid-range joint angles, and a third tube type or configuration can be more accurate for estimating larger joint angles. In an example, a device which collects information from a plurality of sets of different types of tubes spanning the same joint can be more accurate for estimating the angle of that joint over the entire range of motion for the joint than a device collecting information from just one set.

In this example, the functional relationship which is analyzed and used to estimate joint angle is the relationship between joint angle and pressure. In an alternative example, the functional relationship which can be analyzed and used to estimate joint angle can be the relationship between the change in joint angle and the change in pressure. In an example, the functional relationship between joint angle and pressure (or change in joint angle and change in pressure) can be calibrated for a specific person wearing the device, calibrating each time the person wears such a device, calibrated each time the person changes their posture or location, calibrated each time the person performs a specific motion sequence, and/or calibrated at regular time intervals regardless of motion behavior.

In an example, a wearable device for recognizing human motion can comprise: an article of clothing or wearable accessory 102 that is configured to span a body joint 101; at least one tube or channel 103 that is attached to or integrated into the article of clothing or wearable accessory 102 and which is also configured to span body joint 101; a flowable substance which is contained within the tube or channel; and at least one pressure sensor 104 which measures the pressure of the flowable substance.

Three sequential views, as a body joint bends, of a wearable device are shown down the left half of FIG. 1. In the first sequential view (in the upper third of FIG. 1), body joint 101 is shown as fully extended. Relative to the longitudinal axis of the upper portion of the joint, the joint angle in this view is 0 degrees. In this view, article of clothing or wearable accessory 102 (and also the tube or channel 103 which is attached to it) is substantially straight. In the second sequential view (in the middle third of FIG. 1), body joint 101 begins to bend and the joint angle is approximately 20 degrees. In this view, article of clothing or wearable accessory 102 (and also tube or channel 103 which is attached to it) also begins to bend. In the third sequential view (in the lower third of FIG. 1), body joint 101 bends further. Article of clothing or wearable accessory 102 (and also tube or channel 103 which is attached to it) bends further as well.

In this example, article of clothing or wearable accessory 102 stretches as a person's skin stretches. Accordingly, in this example, the article of clothing or wearable accessory 102 does not shift or slide over the surface of the person's skin as the body joint bends and the skin over the joint stretches. In this example, tube or channel 103 is compressed, squeezed, bent, kinked, and/or stretched as body joint 101 bends. This compression, squeezing, bending, kinking, and/or stretching increases the pressure of the flowable substance within tube or channel 103. This increased pressure is reflected in the accompanying graphs down the right half of FIG. 1.

In FIG. 1, the upper or proximal portion of body joint 101 that is not covered by article of clothing or wearable accessory 102 is diagrammatically referenced by indicator line 101, but it is to be understood by the reader that body joint 101 extends down and through the interior of article or accessory 102 and further extends out from the lower end of article or accessory 102. In this example, article of clothing or wearable accessory 102 spans at least a portion of body joint 101. In this example, article of clothing or wearable accessory 102 spans at least a portion of an upper body member and at least a portion of a lower body member, wherein these two body members comprise body joint 101. In this example, tube or channel 103 spans at least a portion of body joint 101. In this example, tube or channel 103 spans at least a portion of an upper body member and at least a portion of a lower body member, wherein these two body members together comprise body joint 101.

In this example, tube or channel 103 is attached to (or integrated into) article of clothing or wearable accessory 102. In this example, tube or channel 103 is attached to (or integrated into) article or accessory 102 by having tube or channel 103 slide into a lumen created between two layers of fabric in article or accessory 102. In other examples, tube or channel 103 can be attached (or integrated) by weaving, sewing, knitting, adhering, gluing, stretching, clipping, buttoning, buckling, zipping, taping, hook-and-eye, magnetizing, and/or melting. In an example, tube or channel 103 can be detached from article of clothing or wearable accessory 102 so that the article or accessory can be washed. In an example, tube or channel 103 can be washable and need not be detached to wash article of clothing or wearable accessory 102.

In this example, tube or channel 103 spans a body joint along the outer and/or frontal side of a hinge joint. In an example, a tube or channel can span the inner and/or dorsal side of a hinge joint. In an example, a tube or channel can span one or both lateral sides of a hinge joint. In an example, a plurality of tubes or channels can span the outer, inner, and lateral sides of a hinge joint.

In an example, a plurality of tubes or channels can longitudinally span the same joint, passing through points on the circumference of the joint which are relatively evenly distributed around that circumference. In an example, the polar coordinates of the points through which a plurality of tubes or channels longitudinally span a joint, relative to the longitudinal axis of the joint, can be evenly distributed within a 0-360 degree range. For example, four tubes can longitudinally span a joint at polar coordinates of approximately 0, 90, 180, and 270 degrees. For example, six tubes can longitudinally span a joint at polar coordinates of approximately 0, 60, 120, 180, 240, and 300 degrees.

In this example, a tube or channel is substantially parallel to the longitudinal axis of the joint when the joint is extended. In an example, a tube or channel can span a body joint at an acute or obtuse angle with respect to the longitudinal axis of the joint when the joint is extended. In an example, a combination of different tubes can span a joint at different angles. In an example, having different tubes span a joint at different angles can be particularly useful for measuring the complex motion of joints which are not hinge joints.

In this example, there is a flowable substance inside tube or channel 103. In this example, this flowable substance is air. In various examples, this flowable substance can be selected from the group consisting of: a gas, a liquid, and a gel. In this example, the pressure of the flowable substance inside tube or channel 103 is measured by pressure sensor 104. Further, there is a positive, monotonic, and non-linear functional relationship between the angle of body joint 101 and the pressure of the flowable substance within tube or channel 103.

In this example, the pressure of a flowable substance within tube or channel 103 increases as body joint 101 bends because tube or channel 103 is compressed, squeezed, bent, kinked, and/or stretched as body joint 101 bends. Article of clothing or wearable accessory 102 is stretched over the skin that spans body joint as body joint 101 bends. In this example, tube or channel 103 is compressed, squeezed, bent, kinked, and/or stretched due to inward pressure from an outer layer of the article of clothing or wearable accessory 102 and outward pressure from the surface of the person's body (conveyed through an inner layer of article of clothing or wearable accessory 102).

In this example, there is only one tube or channel 103 that spans body joint 101. In an example, there can be multiple tubes or channels that span body joint 101. In an example, there can be two or more sets with one or more tubes or channels each that span 101. In an example, tubes or channels within the same set can share one or more common characteristics. In an example, tubes or channels in different sets can differ with respect to one or more characteristics. In an example, one or more such characteristics can be selected from the group consisting of: method of tube or channel attachment to (or integration into) an article of clothing or wearable accessory; type of tube or channel material; level of tube or channel flexibility, durometer, and/or compressibility; tube or channel internal cross-sectional area; tube or channel cross-sectional shape; tube or channel longitudinal shape; tube or channel wall thickness; tube or channel length; type of flowable substance inside a tube or channel; baseline pressure level of the flowable substance within a tube or channel when the joint is fully extended; angle at which a tube or channel spans the longitudinal axis of a joint; radial location with respect to the lateral cross-section of a joint; and segment of the longitudinal axis of a joint that is spanned by a tube or channel.

As will be shown in subsequent figures but is not yet shown in FIG. 1 for the sake of introductory diagrammatic simplicity, data concerning the pressure of a flowable substance in tube or channel 103 which is measured by pressure sensor 104 can be sent to a data processor. In an example, this data processor can be attached to the article of clothing or wearable accessory. In another example, this data can first be sent to a data transmitter and then transmitted to a data processor.

In an example, the functional relationship between the angle of body joint 101 and the pressure of a flowable substance can be analyzed and estimated by a data processor. Once this functional relationship is analyzed and estimated, then the pressure of the flowable substance can be used to estimate and/or predict the angle of the body joint. In an example, the functional relationship can be estimated during a calibration period and the functional relationship can be used to predict body joint angle during a use period. In an example, estimation of multiple body joint angles by a data processor can be used to model and recognize full-body configuration and motion. Information concerning full-body configuration and motion can be used for multiple applications.

In an example, the functional relationship between changes in body joint angle and changes in pressure can be used for estimation and motion recognition instead of using the functional relationship between body joint angle and pressure. In an example, this functional relationship can be analyzed by a data processor. In an example, a functional relationship between a change in the angle of body joint 101 and a change in the pressure of a flowable substance can be used in reverse by a data processor to estimate the change in the angle of body joint 101 based on a change in the pressure of the flowable substance.

As will be shown in subsequent figures but is not yet shown in FIG. 1 for the sake of introductory diagrammatic simplicity, data concerning the pressure of a flowable substance in tube or channel 103 can be sent to a wireless data transmitter which is attached to the article of clothing or wearable accessory. In an example, this data can then be transmitted to a remote data processor which analyzes the relationship between joint angle and substance pressure and/or uses this relationship in reverse to estimate joint angle based on substance pressure. In an example, a data processor and/or data transmitter can be removed from an article of clothing or wearable accessory so that the article or accessory can be washed. In an example, a data processor and/or data transmitter can be waterproof such that it does not have to be removed in order to wash the article or accessory.

In an example, a wearable device for recognizing human motion can comprise an article of clothing that is selected from the group consisting of: shirt, blouse, jacket, pants, dress, shorts, glove, sock, shoe, underwear, belt, and union suit. In an example, a wearable system for recognizing human motion can include a plurality of articles of clothing which include pressure sensors which share electronic communication with a common data processor. In an example, this system can comprise a combination of articles of clothing that are selected from the group consisting of: shirt, blouse, jacket, pants, dress, shorts, glove, sock, shoe, underwear, belt, and union suit.

In an example, an article of clothing or wearable accessory can be made from a close-fitting, elastic, and/or stretchable fabric. In an example, an article of clothing or wearable accessory can be made from one or more materials selected from the group consisting of: Acetate, Acrylic, Cotton, Denim, Latex, Linen, Lycra®, Neoprene, Nylon, Polyester, Rayon, Silk, Spandex, and Wool.

In an example, an article of clothing or wearable accessory can be made from fabric and/or constructed in such a manner that it does not shift with respect to the person's skin when a person moves a body joint. In an example, an article of clothing or wearable accessory can be close-fitting so that it does not shift with respect to a person's skin when the person moves a body joint. In an example, an article of clothing or wearable accessory can cling to a person's skin so that it does not shift with respect to the person's skin when the person moves a body joint. In another example, an article of clothing or wearable accessory can be made from fabric or constructed in such a manner that it fits loosely over a person's skin. In an example, an article of clothing or wearable accessory can shift with respect to a person's skin when the person moves a body joint.

In an example, a wearable device for recognizing human motion can comprise a wearable accessory that is selected from the group consisting of: an elastic tubular accessory that is worn over a knee; an elastic tubular accessory that is worn over an elbow; an elastic tubular accessory that is worn over a shoulder; an elastic tubular accessory that is worn over a hip; an elastic tubular accessory that is worn over an ankle; and an elastic tubular accessory that is worn over the torso and/or waist.

In an example, a wearable device for recognizing human motion can comprise a wearable accessory that is selected from the group consisting of: a flexible adhesive member that is attached to the skin spanning a knee; a flexible adhesive member that is attached to the skin spanning an elbow; a flexible adhesive member that is attached to the skin spanning a shoulder; a flexible adhesive member that is attached to the skin spanning a hip; a flexible adhesive member that is attached to the skin spanning an ankle; and a flexible adhesive member that is attached to the skin spanning the torso and/or waist.

In an example, a wearable device for recognizing human motion can comprise a wearable accessory that is selected from the group consisting of: a flexible bandage that is attached to the skin spanning a knee; an flexible bandage that is attached to the skin spanning an elbow; a flexible bandage that is attached to the skin spanning a shoulder; a flexible bandage that is attached to the skin spanning a hip; a flexible bandage that is attached to the skin spanning an ankle; and a flexible bandage that is attached to the skin spanning the torso and/or waist.

In an example, a wearable device for recognizing human motion can comprise a wearable accessory that is selected from the group consisting of: an electronic tattoo that is attached to the skin spanning a knee; an electronic tattoo that is attached to the skin spanning an elbow; an electronic tattoo that is attached to the skin spanning a shoulder; an electronic tattoo that is attached to the skin spanning a hip; an electronic tattoo that is attached to the skin spanning an ankle; and an electronic tattoo that is attached to the skin spanning the torso and/or waist.

In an example, a wearable system for recognizing human motion can comprise a combination of articles of clothing or wearable accessories which include pressure sensors which are in electronic communication with a common data transmitter and/or data processor. In an example, the components of a system for recognizing human motion can collectively measure full-body motion even though they are physically separate (apart from electromagnetic communication). In various examples, articles of clothing which comprise such a system can be selected from the group consisting of: shirt, blouse, jacket, pants, dress, shorts, glove, sock, shoe, underwear, belt, hat, and union suit. In various examples, wearable accessories which comprise such a system can be selected from the group consisting of: a wearable accessory that is worn over a knee; a wearable accessory that is worn over an elbow; a wearable accessory that is worn over a shoulder; an wearable accessory that is worn over a hip; a wearable accessory that is worn over an ankle; and a wearable accessory that is worn over the torso and/or waist.

In an example, a wearable device for recognizing human motion can comprise an article of clothing or a wearable accessory which longitudinally spans a body joint. In an example, this article of clothing or wearable accessory can longitudinally span the skin that covers the frontal surface, the dorsal surface, and/or the lateral surfaces of a body joint. In an example, an article of clothing or wearable accessory that is part of a wearable device to recognize human motion can span and cover the entire circumference of a body joint. In an example, an article of clothing or wearable accessory that is part of a wearable device to recognize human motion can longitudinally span one or more body joints and/or members selected from the group consisting of: knee, elbow, hip, pelvis, shoulder, ankle, foot, toe, wrist, palm, finger, torso, rib cage, spine, neck, and jaw.

In an example, a single contiguous article of clothing or wearable accessory (such as a union suit) can longitudinally span multiple body joints and/or members. In an example, a set of multiple separate articles of clothing or wearable accessories can comprise a system which collectively spans multiple body joints and/or members. In an example, multiple articles of clothing or wearable accessories can be in electronic communication with each other and/or with a common data processor. In an example, a wearable system for recognizing human motion can include elastic tubular accessories which are worn over elbows and knees. In an example, a wearable system for recognizing human motion can include elastic tubular accessories which are worn on all of a person's fingers on one or both hands. In an example, a wearable system for recognizing human motion can include a union suit which spans a person's elbows, shoulders, knees, hips, and torso.

In an example, an article of clothing or wearable accessory that is part of a wearable device to recognize human motion can span at least a portion of each of the two body segments which comprise the upper and/or proximal member of a body joint and the lower and/or distal member of a body joint. In an example, an article of clothing or wearable accessory can span at least a portion of each of two body segments which contain the upper and/or proximal bone of a body joint and the lower and/or distal bone of a body joint. In an example, this body joint can be selected from the group consisting of: knee, elbow, hip, pelvis, shoulder, ankle, foot, toe, wrist, palm, finger, torso, rib cage, spine, neck, and jaw. In an example, an article of clothing or wearable accessory that is part of a device for measuring human motion can encircle the entire circumference of skin on the exterior of a longitudinal segment of each of the two body members which contain the upper and/or proximal bone of a joint and the lower and/or distal bone of the joint.

In an example, a wearable device for recognizing human motion can include a first set of one or more tubes or channels which contain a flowable substance and which are attached to (or integrated into) an article of clothing or wearable accessory. In an example, a wearable device for recognizing human motion can also include a second set of one or more tubes or channels which contain a flowable substance and which are attached to (or integrated into) an article of clothing or wearable accessory and which span the same joint as that spanned by the first set, but which have one or more design parameters which are different than those of the first set.

In an example, changes in the pressures of a flowable substance in the first and second sets can be used to estimate changes in the angle of a joint which these sets span. In an example, changes in the pressures of a flowable substance in the first and second sets can be used to estimate changes in a single angle of a hinge joint. In an example, changes in the pressures of a flowable substance in the first and second sets can be used to estimate changes in multi-directional angles of a ball-and-socket joint. In an example, combining pressure information from the first and second sets can provide more accurate angle estimates than information from either the first set or the second set alone.

In an example, a set of tubes or channels can be integrated into an article of clothing or wearable accessory by being sewn and/or woven into the fabric of an article of clothing or wearable accessory. In an example, a set of tubes or channels can be integrated into an article of clothing or wearable accessory by sliding a tube or channel through a lumen in the clothing or article. In an example, a set of tubes or channels can be integrated into an article or accessory by fastening them with hook-and-eye material such as Velcro®. In an example, a set of tubes or channels can be integrated into an article of clothing or wearable accessory by placement of the tubes between two layers of material. In an example, a set of tubes or channels can be attached to an article or accessory using an adhesive such as glue. In an example, a set of tubes or channels can be attached to an article or accessory using loops, hooks, clips, buttons, zippers, buckles, tape, and/or snaps.

In an example, a wearable device for recognizing human motion can comprise at least two different sets of tubes or channels which longitudinally span the same body joint. In an example, a set of tubes or channels can longitudinally span the skin that covers the outer or frontal surface, the inner or dorsal surface, and/or the lateral surfaces of a body joint. In an example, a set of tubes or channels that is part of a wearable device to recognize human motion can span and cover the entire circumference of a body joint. In an example, a set of tubes or channels that is part of a wearable device to recognize human motion can longitudinally span one or more body joints and/or members selected from the group consisting of: knee, elbow, hip, pelvis, shoulder, ankle, foot, toe, wrist, palm, finger, torso, rib cage, spine, neck, and jaw.

In an example, a single contiguous set of tubes or channels can longitudinally span multiple body joints and/or members to measure full-body motion. In an example, multiple separate sets of tubes or channels can comprise a system which collectively spans multiple body joints and/or members to measure full-body motion. In an example, multiple sets of tubes or channels can be in electronic communication with each other and/or with a common data processor. In an example, a wearable system for recognizing human motion can include sets of tubes or channels which are worn over elbows and knees. In an example, a wearable system for recognizing human motion can include sets of tubes or channels which are worn over all of the fingers on one or both hands. In an example, a wearable system for recognizing human motion can include sets of tubes or channels which span elbows, shoulders, knees, hips, and torso.

In an example, a set of tubes or channels that is part of a wearable device to recognize human motion can span at least a portion of each of two body segments which together comprise the upper and/or proximal member of a body joint and the lower and/or distal member of a body joint. In an example, a set of tubes or channels can span at least a portion of each of two body segments which contain the upper and/or proximal bone of a body joint and the lower and/or distal bone of a body joint. In an example, this body joint can be selected from the group consisting of: knee, elbow, hip, pelvis, shoulder, ankle, foot, toe, wrist, palm, finger, torso, rib cage, spine, neck, and jaw. In an example, a set of tubes or channels that is part of a device for measuring human motion can encircle the entire circumference of skin on the exterior of a longitudinal segment of each of the two body members which contain the upper and/or proximal bone of a joint and the lower and/or distal bone of the joint.

In an example, a set of tubes or channels can contain a flowable substance which can be a gas, a liquid, or a gel. In an example, this flowable substance can be air. In an example, this flowable substance can be water. In an example, a wearable device for recognizing human motion can include one or more pressure sensors which are in flowable communication with the flowable substances in the tubes or channels. In an example, a flowable substance can be in flowable communication with one or more pressure sensors which measure the pressure of the flowable substance. In an example, changes in the pressure of the flowable substance can be used to estimate changes in the angle of a joint. In an example, the pressure of the flowable substance can be used to estimate the angle of a joint and/or the functional relationship between joint angle and substance pressure.

In an example, the flowable substance within a single tube or channel can be in flowable communication with a single pressure sensor. In an example, there can be one pressure sensor for each tube or channel. In an example, the flowable substance inside a single tube or channel can be in flowable communication with multiple pressure sensors. In an example, there can be two or more pressure sensors for each tube or channel. In an example, the flowable substance inside multiple tubes or channels can be in flowable communication with a single pressure sensor. In an example, there can be two or more tubes or channels for each pressure sensor.

In an example, tubes or channels in a set of tubes or channels can each be self-contained with respect to a flowable substance within them. In an example, there can be no fluid connections between tubes or channels within a set. In an example, tubes or channels in a set of tubes or channels can have connections through which a flowable substance can move from one tube or channel to another tube or channel. In an example, there can be fluid connections between tubes or channels within a set. In an example, tubes or channels within a set and the fluid connections between them can comprise a mesh or lattice which contains a flowable substance. In an example, a mesh or lattice containing a flowable substance can span at least a portion of the outer or frontal, inner or dorsal, and/or lateral surfaces of a body joint.

In an example, pressure information from a pressure sensor can be sent via a wire, circuit, or other electrically-conductive pathway to a data processor which is physically attached to (or integrated into) the article of clothing or wearable accessory which houses the pressure sensor. In an example, information from a pressure sensor can be sent via a wire, circuit, or other electrically-conductive pathway to a data transmitter which is physically attached to (or integrated into) the article of clothing or wearable accessory which houses the pressure sensor. In an example, pressure information sent to a data transmitter can then be transmitted wirelessly to a remote data processor. In an example, multiple pressure sensors can be connected to a single data processor and/or data transmitter.

In an example, a data processor can be disconnected from a pressure sensor and removed from an article or accessory in order to allow the article or accessory to be washed. In an example, a data transmitter can be disconnected from a pressure sensor and removed from an article or accessory in order to allow the article or accessory to be washed. In an example, a pressure sensor can be disconnect from a tube or channel and removed so that an article or accessory can be washed. In an example, tubes or channels can be detached and removed from an article or accessory in order to allow the article or accessory to be washed.

In an example, there can be a functional relationship between the angle of a body joint and the pressure levels of a flowable substance in a set of tubes or channels which span that body joint. In an example, this functional relationship can be positive, non-linear, and monotonic. In an example, this relationship can be estimated with a polynomial model. In an example, this functional relationship can be estimated with least squares estimation. In an example, estimation using this functional relationship can be more accurate over a first range of joint angle values and less accurate over a second range of joint angle values.

In an example, different sets of tubes or channels can have different levels of accuracy for different ranges of joint angle values. In an example, using combined information from different sets of tubes or channels can enable a greater level of accuracy over a wider range of joint angles than using information from a single set of tubes or channels alone. In an example, this functional relationship can be estimated using a spline function. In an example, pressure information from a first set of tubes can be used to estimate a first range in a functional relationship and pressure information from a second set of tubes can be used to estimate a second range in a functional relationship.

In an example, there can be a functional relationship between changes in the angle of a body joint and changes in the pressures of a flowable substance in a set of tubes or channels which span that body joint. In an example, data analysis that is part of this invention can include analysis of the slope of the functional relationship between changes in the angle of a body joint and changes in the pressures of a flowable substance in a set of tubes or channels which span that body joint. In an example, data analysis that is part of this invention can include analysis of the first derivative and second derivatives of the functional relationship between changes in the angle of a body joint and changes in the pressures of a flowable substance in a set of tubes or channels which span that body joint.

In an example, the functional relationship between changes in the angle of a body joint and changes in the pressure of a flowable substance in a set of tubes or channels which span that body joint can be positive, non-linear, and monotonic. In an example, this relationship can be estimated with a polynomial model. In an example, this functional change relationship can be estimated with least squares estimation.

In an example, estimation of a body joint angle using this functional relationship can be more accurate over a first range of changes in joint angle and less accurate over a second range of changes in joint angle. In an example, different sets of tubes or channels can have different levels of accuracy for different ranges of changes in joint angle. In an example, combining information from different sets of tubes or channels can enable a greater level of accuracy over a wider range of changes in joint angle than information from a single set of tubes or channels alone. In an example, this functional relationship can be estimated using a spline function. In an example, changes in pressure information from a first set of tubes can be used to estimate a first range of the functional relationship and changes in pressure information from a second set of tubes can be used to estimate a second range of functional relationship.

In an example, analysis of the relationship between joint angle and pressure can include Fourier analysis. In an example, repeated or cyclical patterns of changes in pressure over time can be identified using Fourier analysis in order to better estimate changes in body joint movement over time. In an example, the speed of repeated cycles can influence the functional relationship between joint angle and substance pressure. In an example, the speed of repeated cycles can particularly influence this functional relationship at the end-points of a cycle wherein joint movement reverses direction. In an example, controlling for motion cycle speed can improve the accuracy of predicting joint angle from substance pressure. Fourier analysis can be used to identify motion cycle speed and to control for motion cycle speed when predicting joint angle from substance pressure.

In an example, analysis of pressure to estimate body joint angle can incorporate information from other types of sensors. In an example, such analysis can incorporate temperature information from a temperature sensor, altitude information from an altimeter, and/or location information from a GPS system. In an example, a person's latitude as measured by an altimeter or (indirectly) by a GPS system can shift the intercept and/or slope of the functional relationship between body joint angle and substance pressure. In an example, the temperature of the flowable substance, as measured by a thermometer, can shift the intercept and/or slope of the functional relationship between body joint angle and substance pressure.

In an example, a wearable device for recognizing human motion can keep track of whether a person is extending or contracting one or more of their joints. In an example, there can be a different functional relationship between joint angle and substance pressure during joint extension than during joint contraction. In an example, the magnitude of this difference in functional relationships during joint extension and contraction can be affected by the speed with which joint extension and contract takes place. In an example, the magnitude of this difference in functional relationships during joint extension and contraction can be affected by the number of cycles of joint extension and contraction which take place in a given period of time. In an example, the magnitude of this difference in functional relationships during joint extension and contraction can be affected by the uniformity of angle range during multiple cycles of joint extension and contraction. In various examples, these factors can be incorporated into the estimation of one or more body joint angles for more accurate modeling of full-body human motion.

In an example, analysis of pressure information to determine the functional relationship between joint angle and pressure can be performed in a data processor. In an example, estimation of a body joint angle based on pressure information can be performed in a data processor. In an example, a data processor can be attached to (or integrated into) an article of clothing or wearable accessory. In an example, a data processor can be disconnected and removed from an article or accessory to allow a person to wash the article or accessory. In an example, a data processor can be in a remote location and receive pressure information that is transmitted wirelessly from a data transmitter. In an example, a data transmitter can be attached to (or integrated into) an article of clothing or wearable accessory. In an example, a data transmitter can be disconnected and removed from the article or accessory to allow a person to wash the article or accessory.

In an example, information from pressure sensors that are in flowable communication with flowable substances in one or more sets of tubes or channels can be transmitted to a mobile electronic device such as a smart phone. In an example, information from pressure sensors that are in flowable communication with flowable substances in one or more sets of tubes or channels can be analyzed as part of an application on a mobile electronic device such as a smart phone. In an example, a smart phone can comprise the user interface for a wearable device that recognizes human movement based on pressure changes in multiple sets of tube or channels that span one or more body joints in an article of clothing or wearable accessory.

In an example, information from pressure sensors that are in flowable communication with flowable substances in one or more sets of tubes or channels can be transmitted to a smart watch or electronically-functional eyewear. In an example, information from pressure sensors that are in flowable communication with flowable substances in one or more sets of tubes or channels can be analyzed as part of an application on a smart watch or electronically-functional eyewear. In an example, a smart watch or electronically-functional eyewear can comprise the user interface for a wearable device that recognizes human movement based on pressure changes in multiple sets of tube or channels that span one or more body joints in an article of clothing or wearable accessory.

In an example, pressure information from different sets of tubes or channels that longitudinally span a joint at different radial locations can have different functional relationships between joint angle and flowable substance pressure. In an example, pressure information from different tubes or channels that longitudinally span a joint at different radial locations can be combined using multivariate analysis to more accurately estimate one or more joint angles than is possible with information from a single tube or channel that longitudinally spans a joint at one radial location.

In an example, tubes or channels at different radial locations can differ in one or more design parameters selected from the group consisting of: the method by which tubes or channels in each set are attached to or integrated into an article of clothing or wearable accessory; the type of tube or channel material in a set; the construction of tubes or channels in a set; the flexibility, durometer, and/or elasticity of tubes or channels in a set; the cross-sectional shape and/or cross-sectional uniformity of tubes or channels in a set; the longitudinal shape and/or longitudinal uniformity of tubes or channels in a set; the inner area size of tubes or channels in a set; the wall thickness of tubes or channels in a set; the length of tubes or channels in a set; the angle of intersection between tubes or channels in a set and the longitudinal axis of the joint; and the independence or connections (e.g. mesh or lattice) between tubes or channels in a set.

FIG. 2 shows two general examples of how a wearable device for recognizing human motion can be used. The first example involves using the wearable device to model and/or replicate human motion in a virtual object. The second example involves using the wearable device to model and/or replicate human motion in a physical object.

The upper half of FIG. 2 shows an example of how this device can be used to animate a virtual avatar. The left side of the upper half of FIG. 2 shows a running woman 201. This woman 201 is wearing a union suit of stretchable material which spans multiple joints including her knees, hips, torso, shoulders, and elbows. In this example, it is assumed that there are multiple tubes or channels attached to (or integrated into) the union suit to span different body joints, but only one tube (103) is shown in a transparency view. Pressure information from the multiple tubes (including tube 103) is transmitted wirelessly via electromagnetic signal 202 to computer 203. Computer 203 uses this pressure information to model movement of the woman's body and the animated avatar on the screen of computer 203 imitates the movements of the running woman 201.

In this example, a wearable device for recognizing human motion works as follows. First, as the woman runs, she contracts and extends her joints. Next, as her joints contract and extend, they compress and release the tubes (integrated into the clothing) which span those joints. Then, as the tubes are compressed and released, the pressures of the flowable substances in the tube increase and decrease. Then, increases and decreases in the pressures of the flowable substance are used to estimate changes in joint angles. Finally, changes in joint angles are used to model and recreate the woman's movements in the movement of a virtual avatar Animation of a virtual avatar, such as shown in the upper portion of FIG. 2, can be used for various applications including: sports training, computer gaming, virtual exercising, video-conferencing, virtual reality interaction, making animated motion pictures, and medical diagnosis.

The bottom half of FIG. 2 shows an example of how this device can be used to animate a physical object. In an example, this can be a telerobotics application. Pressure information from multiple tubes (including tube 103) is transmitted wirelessly through wireless signal 202 to robot 204. This pressure information is then used to control actuators within robot 204 which cause robot 204 to imitate the movements of the running woman 201. In this example, the robot which is controlled by this device is anthropomorphic. In another example, a robot which is controlled by this device can have a non-anthropomorphic form.

FIG. 3 outlines examples of how this invention can be embodied in wearable devices for recognizing human motion. In an example, a wearable device can have five basic elements: (1) an article of clothing or wearable accessory that at least partially spans at least one body joint; (2) at least one tube or channel attached to or integrated into the article or accessory; (3) a flowable substance within at least one tube or channel; (4) at least one pressure sensor in communication with the flowable substance; and (5) a data transmitter and/or data processor that receives signals from the pressure sensor, wherein these signals are used to estimate the angle or configuration of at least one body joint. FIG. 3 also shows key design parameters for each of these five elements and outlines ways in which these key design parameters can be varied within the scope of this invention.

In an example, two or more sets of different types of tubes or channels can span the same body joint. In an example, one or more design parameters in a first set of tubes or channels can be different than those design parameters for a second set of tubes or channels. In an example, these different design parameters can be selected from the group consisting of: the method of attachment (or integration) of tubes or channels and the article or accessory; the type of tube or channel material; the level of tube or channel flexibility, durometer, and/or compressibility; the internal cross-sectional area of a tube or channel; the cross-sectional shape of a tube or channel; the longitudinal shape of a tube or channel; tube or channel wall thickness; tube or channel length; the type of flowable substance in a tube or channel; the pressure level within a tube or channel when the joint is fully extended; the angle at which a tube or channel spans the longitudinal axis of the joint; the radial location with respect to the lateral cross-section of the joint by which a tube or channel spans the joint; and the segment of the longitudinal axis of the joint that is spanned by a tube or channel.

According to FIG. 3, design parameters for an article of clothing or wearable accessory that spans at least one body joint can be selected from the group consisting of: type of article of clothing or wearable accessory; type and construction of fabric or material; fit, tightness, and/or elasticity; and spanning one joint or multiple joints. In an example, an article of clothing can be a pair of pants, a shirt, or a union suit. In an example, a wearable accessory can be a tube of stretchable fabric that covers one or more joints.

In an example, an article of clothing or wearable accessory can be made with woven, elastic fabric or material. In an example, an article of clothing or wearable accessory can fit relatively closely to a person's body and can stretch as the person's joint moves. In an example, an article of clothing or wearable accessory can fit loosely on a person and can use multiple data sources to control for shifts in location as a person's joint moves. In an example, a system for recognizing human motion can comprise multiple articles of clothing or multiple wearable accessories that collectively span virtually all of a person's joints for full-body motion recognition.

According to FIG. 3, design parameters for a tube or channel that is attached to (or integrated into) an article of clothing or wearable accessory can be selected from the group consisting of: the method of attaching and/or integrating the tube and wearable article; having a single tube spanning a joint or an array of multiple tubes spanning a joint; tube material type, flexibility, durometer, and/or composite structure; tube cross-sectional inner area size, wall thickness, and shape; tube longitudinal length, shape, and/or non-uniform configuration; angle of tube spanning longitudinal joint axis; number of tubes and radial locations of tube in array; separate tubes or inter-connected tubes [such as a lattice or mesh] in array; different tube types in an array; and having removable tubes that allow an article to be washed or having tubes that can be washed.

In an example, a tube or channel can be attached to (or integrated into) an article of clothing or wearable accessory by being woven into the fabric of the article or accessory. In an example, a tube can be attached by adhesive. In an example, a tube can fit within a channel or pocket within the clothing or accessory. In an example, a tube can be attached using Velcro®.

In an example, a single tube can span a given body joint. In an example, multiple tubes can span a given body joint. In an example, two or more sets of different types of tubes can span a given body joint. In an example, different types of tubes can vary in terms of material used, the durometer of material, and their overall flexibility. In an example, braided tubes or tubes with other types of composite structures can be used. In an example, balloon-like tubes can be used. In an example, different tubes can have different size or shaped interior cross-sections. In an example, different tubes can have different wall thicknesses. In an example, a tube can have different cross-sectional shapes at different locations along its longitudinal axis.

In an example, a tube spanning a joint can have different characteristics over the central portion of a joint than over the peripheral portions of the joint. In an example, a tube spanning a joint can be thicker at the center of a joint and thinner away from the center of the joint. In an example, a tube spanning a joint can be less flexible at the center of a joint and more flexible away from the center of the joint. In an example, a tube spanning a joint can have a larger cross-sectional area at the center of the joint and a smaller cross-sectional area away from the center of the joint.

In an example, different tubes can have different lengths. In an example, multiple parallel tubes of different lengths can span the same joint. In an example, one or more tubes can be curved. In an example, a tube can be sinusoidal in shape, varying around its longitudinal axis, as it spans a joint.

In an example, there can be multiple tubes spanning a given body joint. In an example, a tube array can span a given body joint. In an example, different tubes can span the same body joint across different radial locations. In an example, different tubes can longitudinally cross the same circumference around a body joint at different radial locations around that circumference. In an example, these radial locations can be substantially evenly spaced around the circumference. In an example, tubes can be completely separate as they span the same body joint. In an example, tubes can be connected into a lattice or mesh as they span the same body joint. In an example, tubes can be removable from an article or accessory in order to allow the article or accessory to be washed.

According to FIG. 3, design parameters for a flowable substance within a tube or channel can be selected from the group consisting of: the type of liquid or gas substance; substance density and/or viscosity; baseline substance pressure; and whether the substance is refillable to calibrate pressure. In an example, a flowable substance can be air. In an example, a flowable substance can be water. In an example, different tubes can have different baseline pressures (at full joint extension) for flowable substances within them. In an example, a flowable substance can be refilled or re-pressurized to restore a desired baseline pressure.

According to FIG. 3, design parameters for a pressure sensor that is in communication with a flowable substance can be selected from the group consisting of: type of pressure sensor; pressure range; sensor location with respect to a tube, article, and/or joint; whether there is one sensor per tube, are multiple sensors per tube, or are multiple tubes per sensor; and whether a sensor is removable to allow an article or accessory to be washed.

In an example, pressure sensors in different tubes can have different pressure ranges. In an example, a pressure sensor can be placed completely inside a tube. In an example, a pressure sensor can be connected to the end of a tube. In an example, there can be multiple pressure sensors in different locations in flowable communication with the flowable substance in the same tube. In an example, there can be multiple pressure sensors in different locations in a lattice or mesh of tubes or channels.

According to FIG. 3, design parameters for a data transmitter and/or data processor that receives signals from a pressure sensor (wherein these signals are used to estimate the angle or configuration of at least one body joint) can be selected from the group consisting of: whether the information is first sent to a data transmitter or to a data processor; the location of the data transmitter and/or data processor; whether the data transmitter or data processor is removable to wash an article or is itself washable; the analytic methods used to estimate joint angle(s) from tube pressure(s); single angle for hinge joint and/or multiple angles for other joint types; multivariate analysis of pressure from multiple tubes; Fourier analysis of repeated pressure patterns; calibration method; and use of data from supplementary sensors such as a thermometer, altimeter, or GPS.

In an example, data from one or more pressure sensors can be sent via wire or circuit to a data transmitter which in turn sends this data to a remote data processor. In an example, data from one or more pressure sensors can be sent directly to a data processor which is an integral part of an article of clothing or wearable accessory. In an example, a data transmitter or data processor can be disconnected from an article of clothing or wearable accessory so that the article or accessory can be washed.

In an example, multivariate statistical analysis can be used to estimate a functional relationship between joint angle and substance pressure. In an example, multivariate statistical estimation can be used to estimate the joint angle from tube pressure. In an example, a single joint angle for a hinge joint can be estimated from the pressure levels in one or more tubes or channels spanning that hinge joint. In an example, two or more joint angles can be estimated from the pressure levels in multiple tubes or channels spanning a ball-and-socket or other type of non-hinge joint.

In an example, Fourier analysis can be used to identify patterns of joint movement from cyclical variation in tube pressure(s) over time. In an example, data from supplemental sensors such as a thermometer, altimeter, and/or GPS can be used as additional input for a multivariate model to recognize and model body motion. For example, the functional relationship between joint angle and pressure can be adjusted for differences in temperature, altitude, and/or location.

In an example, a wearable device for recognizing human motion can comprise sets of different types of tubes or channels which longitudinally span one or more body joints. In an example, tubes or channels in these sets can contain a flowable substance and changes in the pressures of the flowable substance in these tubes or channels (as joints bend) can be used to estimate the bending angles of body joints. In an example, pressure information from sets of different types of tubes and channels spanning the same joint can provide more accurate estimates of the angle of that joint than pressure information from a single set of tubes or channels spanning that joint.

In an example, a wearable device for recognizing human motion can comprise: (a) an article of clothing that spans a body joint; (b) a first set of one or more tubes that are attached to or integrated into the article of clothing, wherein this first set contains a flowable substance whose pressure is measured by a pressure sensor, wherein there is a first functional relationship between an angle of the body joint and the pressure of the flowable substance in this first set; and (c) a second set of one or more tubes that are attached to or integrated into the article of clothing, wherein this second set contains a flowable substance whose pressure is measured by a pressure sensor, wherein there is a second functional relationship between an angle of the body joint and the pressure of the flowable substance in this second set, and wherein use of pressure information from both the first set and the second set enables more accurate estimation of at least one joint angle than pressure information from either the first set alone or the second set alone.

In an example, a wearable device for recognizing human motion can comprise: (a) a wearable accessory that spans a body joint; (b) a first set of one or more tubes that are attached to or integrated into the wearable accessory, wherein this first set contains a flowable substance whose pressure is measured by a pressure sensor, wherein there is a first functional relationship between an angle of the body joint and the pressure of the flowable substance in this first set; and (c) a second set of one or more tubes that are attached to or integrated into the article of clothing, wherein this second set contains a flowable substance whose pressure is measured by a pressure sensor, wherein there is a second functional relationship between an angle of the body joint and the pressure of the flowable substance in this second set, and wherein use of pressure information from both the first set and the second set enables more accurate estimation of at least one joint angle than pressure information from either the first set alone or the second set alone.

In an example, a wearable system for recognizing human motion can comprise: a wearable item that spans at least one body joint, wherein this item further comprises a first set of one or more tubes or channels which contain a flowable substance, wherein there is a first functional relationship between movement of the body joint and changes in the pressures of the flowable substance in this first set of tubes or channels, wherein this accessory further comprises a second set of one or more tubes or channels which contain a flowable substance, wherein there is a second functional relationship between movement of the body joint and changes in the pressures of the flowable substance in the second set of tubes or channels, and wherein using pressure information from both the first set and the second set enables more accurate modeling of body joint movement than using pressure information from either the first set alone or the second set alone.

In an example, a wearable system for recognizing human motion can comprise: a plurality of wearable items that are worn by a person, wherein each of the wearable items spans at least one body joint, wherein each of the wearable items comprises a first set of one or more tubes or channels which contain a flowable substance, wherein there is a first functional relationship between movement of the body joint and changes in the pressures of the flowable substance in this first set of tubes or channels, wherein each of the wearable items also comprises a second set of one or more tubes or channels which contain a flowable substance, wherein there is a second functional relationship between movement of the body joint and changes in the pressures of the flowable substance in the second set of tubes or channels, and wherein using pressure information from both the first set and the second set enables more accurate modeling of body joint movement than using pressure information from either the first set alone or the second set alone.

In an example, a wearable device for recognizing human motion can comprise: (a) an article of clothing or wearable accessory, wherein this article or accessory spans at least a portion of at least one body joint; (b) at least one pressure sensor; (c) a first set of one or more tubes or channels, wherein this first set is attached to or integrated into the article of clothing or wearable accessory, wherein this set spans at least a portion of a body joint, wherein this first set contains a flowable substance, wherein the pressures of the flowable substance in this first set is measured by at least one pressure sensor, wherein there is a first functional relationship between an angle of the body joint and the pressure of the flowable substance in this first set; (d) a second set of one or more tubes or channels, wherein this second set is attached to or integrated into the article of clothing or wearable accessory, wherein this second set spans at least a portion of the same body joint that is spanned by the first set, wherein this second set contains a flowable substance, wherein the pressures of the flowable substance in this second set is measured by at least one pressure sensor, wherein there is a second functional relationship between the angle of the body joint and the pressure of the flowable substance in this second set; and (e) a data processor and/or data transmitter that analyzes pressure information from both the first set and the second set to estimate at least one angle of the body joint and/or transmits pressure information from the first set and the second set to a remote data processor which analyzes pressure information from the first set and the second set to estimate at least one angle of the body joint; and wherein use of pressure information from both the first set and the second set enables more accurate estimation of the at least one joint angle than pressure information from either the first set or the second set alone.

In an example, a wearable device for recognizing human motion can comprise: (a) an article of clothing or wearable accessory, wherein this article or accessory spans at least a portion of at least one body joint; (b) at least one pressure sensor; (c) a first set of one or more tubes or channels, wherein this first set is attached to or integrated into the article of clothing or wearable accessory, wherein this set spans at least a portion of a body joint, wherein this first set contains a flowable substance, wherein the pressures of the flowable substance in this first set is measured by at least one pressure sensor, wherein there is a first functional relationship between an angle of the body joint and the pressure of the flowable substance in this first set; wherein this first set is attached to or integrated into the article or accessory using a first method; wherein this first set is made from a first type of material; where this first set has a first level of flexibility, durometer, and/or compressibility; wherein this first set has a first internal cross-sectional area; wherein this first set has a first cross-sectional shape; wherein this first set has a first longitudinal shape; wherein this first set has a first wall thickness; wherein this first set has a first length; wherein this first set contains a first type of flowable substance; wherein the flowable substance in this first set has a first pressure level when the joint is fully extended; wherein this first set intersects the longitudinal axis of the joint at a first angle; wherein this first set spans the longitudinal axis of the joint at a first radial location with respect to the lateral cross-section of the joint; and wherein this first set spans a first segment of the longitudinal axis of the joint; (d) a second set of one or more tubes or channels, wherein this second set is attached to or integrated into the article of clothing or wearable accessory, wherein this second set spans at least a portion of the same body joint that is spanned by the first set, wherein this second set contains a flowable substance, wherein the pressures of the flowable substance in this second set is measured by at least one pressure sensor, wherein there is a second functional relationship between the angle of the body joint and the pressure of the flowable substance in this second set; wherein this second set is attached to or integrated into the article or accessory using a second method; wherein this second set is made from a second type of material; where this second set has a second level of flexibility, durometer, and/or compressibility; wherein this second set has a second internal cross-sectional area; wherein this second set has a second cross-sectional shape; wherein this second set has a second longitudinal shape; wherein this second set has a second wall thickness; wherein this second set has a second length; wherein this second set contains a second type of flowable substance; wherein the flowable substance in this second set has a second pressure level when the joint is fully extended; wherein this second set spans the longitudinal axis of the joint at a second angle; wherein this second set spans the longitudinal axis of the joint at a second radial location with respect to the lateral cross-section of the joint; wherein this second set spans a second segment of the longitudinal axis of the joint; wherein the embodiment of at least one design parameter of the second set is different than that of the first set and wherein this at least one design parameter is selected from the group consisting of—method of attachment to or integration into the article or accessory; type of material; level of flexibility, durometer, and/or compressibility; internal cross-sectional area; cross-sectional shape; longitudinal shape; wall thickness; length; type of flowable substance; pressure level when the joint is fully extended; angle spanning the longitudinal axis of the joint; radial location with respect to the lateral cross-section of the joint; and segment of the longitudinal axis of the joint that is spanned; and (e) a data processor and/or data transmitter that analyzes pressure information from both the first set and the second set to estimate at least one angle of the body joint and/or transmits pressure information from the first set and the second set to a remote data processor which analyzes pressure information from the first set and the second set to estimate at least one angle of the body joint; and wherein use of pressure information from both the first set and the second set enables more accurate estimation of the at least one joint angle than pressure information from either the first set or the second set alone.

In an example, a wearable device for recognizing human motion can comprise: (a) an article of clothing or wearable accessory, wherein this article or accessory spans at least a portion of at least one body joint; (b) at least one pressure sensor; (c) a first set of one or more tubes or channels, wherein this first set is attached to or integrated into the article of clothing or wearable accessory, wherein this set spans at least a portion of a body joint, wherein this first set contains a flowable substance, wherein the pressures of the flowable substance in this first set is measured by at least one pressure sensor, wherein there is a first functional relationship between an angle of the body joint and the pressure of the flowable substance in this first set; wherein this first set is attached to or integrated into the article or accessory using a first method; wherein this first set is made from a first type of material; where this first set has a first level of flexibility, durometer, and/or compressibility; wherein this first set has a first internal cross-sectional area; wherein this first set has a first cross-sectional shape; wherein this first set has a first longitudinal shape; wherein this first set has a first wall thickness; wherein this first set has a first length; wherein this first set contains a first type of flowable substance; wherein the flowable substance in this first set has a first pressure level when the joint is fully extended; wherein this first set intersects the longitudinal axis of the joint at a first angle; wherein this first set spans the longitudinal axis of the joint at a first radial location with respect to the lateral cross-section of the joint; and wherein this first set spans a first segment of the longitudinal axis of the joint; (d) a second set of one or more tubes or channels, wherein this second set is attached to or integrated into the article of clothing or wearable accessory, wherein this second set spans at least a portion of the same body joint that is spanned by the first set, wherein this second set contains a flowable substance, wherein the pressures of the flowable substance in this second set is measured by at least one pressure sensor, wherein there is a second functional relationship between the angle of the body joint and the pressure of the flowable substance in this second set; wherein this second set is attached to or integrated into the article or accessory using a second method; wherein this second set is made from a second type of material; where this second set has a second level of flexibility, durometer, and/or compressibility; wherein this second set has a second internal cross-sectional area; wherein this second set has a second cross-sectional shape; wherein this second set has a second longitudinal shape; wherein this second set has a second wall thickness; wherein this second set has a second length; wherein this second set contains a second type of flowable substance; wherein the flowable substance in this second set has a second pressure level when the joint is fully extended; wherein this second set spans the longitudinal axis of the joint at a second angle; wherein this second set spans the longitudinal axis of the joint at a second radial location with respect to the lateral cross-section of the joint; wherein this second set spans a second segment of the longitudinal axis of the joint; wherein the embodiment of at least one design parameter of the second set is different than that of the first set and wherein this at least one design parameter is selected from the group consisting of—method of attachment to or integration into the article or accessory; type of material; level of flexibility, durometer, and/or compressibility; wall thickness; and radial location with respect to the lateral cross-section of the joint; and (e) a data processor and/or data transmitter that analyzes pressure information from both the first set and the second set to estimate at least one angle of the body joint and/or transmits pressure information from the first set and the second set to a remote data processor which analyzes pressure information from the first set and the second set to estimate at least one angle of the body joint; and wherein use of pressure information from both the first set and the second set enables more accurate estimation of the at least one joint angle than pressure information from either the first set or the second set alone.

FIG. 4 outlines examples of how this invention can be embodied in methods for recognizing human motion. In an example, a method for recognizing human motion can comprise five steps: (1) creating an article of clothing or wearable accessory that at least partially spans at least one body joint; (2) attaching or integrating at least one tube or channel and the article or accessory; (3) filling the tube or channel with a flowable substance; (4) placing at least one pressure sensor in communication with the flowable substance; and (5) receiving pressure signals from the pressure sensor in a data processor, wherein these signals are used to estimate the angle and/or configuration of at least one body joint.

In a variation on this example, this invention can be embodied in a method for recognizing human motion that uses two sets of different types of tubes, wherein both of these sets of tubes span the same body joint. In an example, such a method can comprise the following steps: (1) creating an article of clothing or wearable accessory that spans at least one body joint; (2) attaching or integrating a first set of tubes or channels and the article or accessory, wherein this first set of tubes is filled with a flowable substance; (3) attaching or integrating a second set of tubes or channels and the article or accessory, wherein this second set of tubes is filled with a flowable substance, wherein one or more design parameters of the second set differ from those of the first set, and wherein these design parameters are selected from the group consisting of: the method of attachment to or integration of tubes or channels into the article or accessory; the type of tube or channel material; the level of tube or channel flexibility, durometer, and/or compressibility; the internal cross-sectional area of the tube or channel; the cross-sectional shape of the tube or channel; the longitudinal shape of the tube or channel; tube or channel wall thickness; tube or channel length; the type of flowable substance in the tube or channel; the pressure level within the tube or channel when the joint is fully extended; the angle at which the tube or channel spans the longitudinal axis of the joint; the radial location with respect to the lateral cross-section of the joint by which the tube or channel spans the joint; and the segment of the longitudinal axis of the joint that is spanned by the tube or channel; flowable substance; and (4) using the pressure levels of the flowable substance in the first set and the second set to estimate the angle or configuration of at least one body joint.

In an example, this invention can be embodied in a method for recognizing human motion that uses two sets of different types of tubes, wherein both of these sets of tubes span the same body joint. In an example, such a method can comprise the following steps: (1) creating an article of clothing or wearable accessory that spans at least one body joint; (2) attaching or integrating at least two sets of tubes or channels and the wearable article, wherein these tubes or channels contain a flowable substance, wherein these two sets differ in one or more key design parameters, and wherein one or more design parameters of the second set differ from those of the first set, and wherein these design parameters are selected from the group consisting of: the method of attachment to or integration of tubes or channels into the article or accessory; the type of tube or channel material; the level of tube or channel flexibility, durometer, and/or compressibility; the internal cross-sectional area of the tube or channel; the cross-sectional shape of the tube or channel; the longitudinal shape of the tube or channel; tube or channel wall thickness; tube or channel length; the type of flowable substance in the tube or channel; the pressure level within the tube or channel when the joint is fully extended; the angle at which the tube or channel spans the longitudinal axis of the joint; the radial location with respect to the lateral cross-section of the joint by which the tube or channel spans the joint; and the segment of the longitudinal axis of the joint that is spanned by the tube or channel; flowable substance; and (3) using information on pressure levels in both sets of tubes or channels to estimate and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the method of attachment, connection, and/or integration of tubes or channels and the article or accessory; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the type of tube or channel material; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the level of tube or channel flexibility, durometer, and/or compressibility; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the internal cross-sectional area of a tube or channel; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the cross-sectional shape of a tube or channel; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the longitudinal shape of a tube or channel; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to tube or channel wall thickness; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to tube or channel length; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the type of flowable substance in a tube or channel; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the pressure level within a tube or channel when the joint is fully extended; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the angle at which a tube or channel spans the longitudinal axis of the joint; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the radial location with respect to the lateral cross-section of the joint by which the tube or channel spans the joint; and (4) using the pressures the flowable substance in both the first and second sets to estimate, predict, and/or model movement of at least one body joint.

In an example, a method for recognizing human motion can comprise: (1) creating an article of clothing or wearable accessory that spans at least one body joint when worn by a person; (2) attaching, connecting, and/or integrating a first set of tubes or channels to the article or accessory, wherein this first set spans at least a portion of a body joint, and wherein this first set contains a flowable substance; (3) attaching, connecting, and/or integrating a second set of tubes or channels to the article or accessory, wherein this second set spans at least a portion of the same body joint that is spanned by the first set, wherein the second set contains a flowable substance, and wherein the second set differs from the first set with respect to the segment of the longitudinal axis of the joint that is spanned by a tube or channel; and (4) using the pressures the flowable substance in both the first and second sets to estimate, predict, and/or model movement of at least one body joint.

In an example, a method for recognizing human motion can comprise: filling a flexible tube with a flowable substance; placing a pressure sensor in contact with the flowable substance; attaching the tube to an article of clothing or wearable accessory such that the tube spans at least a portion of a body joint when the article of clothing or wearable accessory is worn by a person; measuring the pressure of the flowable substance within the flexible tube as the body joint moves; and estimating at least one angle of the body joint based on the pressure of the flowable substance.

FIG. 5 shows an example of how this invention can be embodied in a wearable stretchable accessory 102 that is worn over a body joint 101, wherein this accessory comprises multiple, generally-parallel tubes (including tubes 501, 504, and 507) which cross the circumference of body joint 101 at locations which are relatively-evenly distributed around the circumference of body joint 101. The side-view of this example in FIG. 5 shows three tubes spanning the joint. One of these tubes shown (501) spans the outer or frontal side of the joint. The second of these tubes shown (504) spans one of the lateral sides of the joint. A third of these tubes that is shown (507) spans the inner or dorsal side of the joint. In this example, these three tubes are generally parallel and of equal length when the joint is fully extended, although they can bend, stretch, or compress to different lengths and shapes as the joint bends.

As shown in FIG. 5, tube 501 contains a flowable substance 502 which is in fluid communication with pressure sensor 503. Tube 504 contains a flowable substance 505 which is in fluid communication with pressure sensor 506. Tube 507 contains a flowable substance 508 which is in fluid communication with pressure sensor 509.

FIG. 5 also shows a power source 511 and a data transmitter 510 which are attached to the wearable stretchable accessory. The three pressure sensors (503, 506, and 509) are in electrical communication with data transmitter 510 via small sinusoidal wires. In this example, the pressures of the substances (502, 505, and 508) in the three tubes (501, 504, and 507) are measured by the three pressure sensors (503, 506, and 509). This pressure data is sent to data transmitter 510 via wires. Then, this data is transmitted to a remote data processor where it is used to estimate the angle of body joint 101. In an example, multiple such accessories spanning multiple body joints and measuring pressure changes in tubes spanning these multiple body joints can comprise a system that can recognize and model full-body motion.

In an example, having multiple (generally-parallel) tubes or channels which span the same body joint, as shown in FIG. 5, can enable a wearable device to differentiate between changes in tube or channel pressure which are due to normal movement of the body joint and changes in tube or channel pressure which are due to compressive contact with an environmental object. For example, when a person sits down on a chair or lies down on a bed, the surface of the chair or bed exerts compressive force on portions of the person's body. For wearable device configurations in which there are tubes or channels which span the portions of the person's body which contact the chair or bed, the force of the chair or bed can compress these tubes or channels and confound measurement of body joint angle based on pressure. If there is only one tube or channel which spans a given joint or body segment and this tube or channel is compressed by contact with a chair or bed, then this can confound measurement of body joint angle based on pressure.

However, contact between a person's body and an environmental object such as a chair or bed generally does not involve the entire circumference of a joint or body member. For example, when a person sits down on a chair, this may compress their buttocks, back, and dorsal surfaces of their upper legs, but not the sides or front of their torso or the frontal surfaces of their upper legs.

A wearable device for measuring human motion (such as the one shown in FIG. 5) which includes multiple tubes or channels which span the dorsal, lateral, and frontal surfaces of body joints and segments can detect higher-than-normal pressures on dorsal body surfaces relative to normal pressures on frontal body surfaces. In this manner, a wearable device with multiple tubes or channels which span the same body joint or segment can differentiate between pressure changes which are due to normal body joint movement and pressure changes which are due to compressive contact with an environmental object (such as a chair or bed).

Changes in altitude can uniformly affect the pressures within tubes or channels around the entire circumference of a body joint or segment. However, the integration of an altimeter and/or GPS unit into a wearable device can help the device to control for these circumferentially-uniform changes in pressure. Also, being immersed in water (as when a person is swimming) can affect the pressure within tubes or channels around the entire circumference of a body joint or segment. However, the integration of a water sensor into a wearable device can help the device to control for these circumferentially-uniform changes in pressure. Also, changes in environmental and/or body temperature can affect the pressure within tubes or channels around the entire circumference of a body joint or segment. However, the integration of a thermometer into a wearable device can help the device to control for these circumferentially-uniform changes in pressure.

FIG. 6 shows an example of how this invention can be embodied in a wearable stretchable accessory 102 that is worn over a body joint 101, wherein this accessory comprises two sets of tubes or channels and wherein these two sets differ in tube length. In this example, a first set of tubes or channels (including tubes or channels 601, 604, and 607) are longer and a second set of tubes or channels (including tubes or channels 610, 613, and 616) are shorter. In this example, both sets of tubes of channels are generally parallel when the joint is extended and both sets of tubes or channels share a common center that is generally around the central circumference of the joint.

Tubes or channels in the longer first set, including tubes or channels 601, 604, and 607, contain flowable substances 602, 605, and 608 (respectively) which are in flowable communication with pressure sensors 603, 606, and 609 (respectively). Tubes or channels in the shorter second set, including tubes or channels 610, 613, and 616, contain flowable substances 611, 614, and 617 (respectively) which are in flowable communication with pressure sensors 612, 615, and 618 (respectively). The six pressure sensors in this example are in electrical communication with data transmitter 510 via small sinusoidal wires. Data transmitter 510 is powered by power source 511.

In an example, the first set (of longer tubes or channels including 601, 604, and 607) can more-accurately measure the relationship between changes in joint angle and changes in substance pressure in the mid-range of body joint angles. In an example, the second set (of shorter tubes including 610, 613, and 616) can more-accurately measure the relationship between changes in joint angle and changes in substance pressure in low-range and high-range body joint angles. In an example, using pressure information from both the first set and the second set (in a multivariate manner) can enable more accurate estimation of body joint angle over a wider range of angles than using pressure information from either the first set alone or the second set alone.

In the example shown in FIG. 6, tubes or channels in a first set and tubes or channels in a second set both longitudinally span the same body joint. In this example, multiple tubes or channels in a first set that spans a body joint are substantially parallel to multiple tubes or channels in a second set that spans the same body joint. In this example, tubes or channels in a first set and tubes or channels in a second set have longitudinal centers which are located around a common circumference of the same lateral cross-section of a body joint.

In the example shown in FIG. 6, tubes or channels in a first set and tubes or channels in a second set are distributed in an alternating (first, second, first, second) manner as they cross the circumference of the joint. In this example, tubes or channels in the first and second sets have longitudinal centers which are located around the circumference of the same cross-section of the joint, but tubes or channels in the first set have a different length than tubes or channels in the second set. This can help to more accurately measure different ranges of joint angle movement.

In an example, a first set of tubes or channels spanning a body joint can be more accurate for estimating the body joint angle based on the pressures of a flowable substance within that first set over a lower range of body joint angles. In an example, a second set of tubes or channels spanning a body joint can be more accurate for estimating the body joint angle based on the pressures of a flowable substance within that second set over a higher range of body joint angles. In an example, using pressure information from both a first set and a second set can be more accurate for estimating body joint angle than using pressure information from either the first set or the second set alone.

In an example, a multivariate model for estimating a body joint angle based on flowable substance pressures can include an interaction term between flowable substance pressures in a first set and flowable substance pressures in a second set. In an example, a multivariate model for estimating changes in body joint angle based on changes in flowable substance pressures can include an interaction term between changes in flowable substance pressures in a first set and changes in flowable substance pressure in a second set.

In an example, tubes or channels in a first set and tubes or channels in a second set can have longitudinal centers which are located on the circumference of the same lateral cross-section of a body joint, but tubes or channels in the first set can have a different level of flexibility, durometer, and/or elasticity than tubes or channels in the second set. In an example, tubes or channels in a first set and tubes or channels in a second set can have longitudinal centers which are located on the circumference of the same lateral cross-section of a body joint, but tubes or channels in the first set can have a different cross-sectional shape than tubes or channels in the second set.

In an example, tubes or channels in a first set and tubes or channels in a second set can have longitudinal centers which are located on the circumference of the same lateral cross-section of a body joint, but tubes or channels in the first set can have a different longitudinal shape than tubes or channels in the second set. In an example, tubes or channels in a first set and tubes or channels in a second set can have longitudinal centers which are located on the circumference of the same lateral cross-section of a body joint, but tubes or channels in the first set can have a different inner area size than tubes or channels in the second set.

In the example shown in FIGS. 5 and 6, movement of a hinge joint can be modeled by one joint angle. In another example, movement of a ball joint can be modeled by multiple joint angles. In an example, a first set of tubes or channels which span a ball joint can be more accurate for estimating a first joint angle based on the pressure of the flowable substance. In an example, a second set of tubes or channels spanning a ball joint can be more accurate for estimating a second joint angle based on the pressure of the flowable substance within that second set. In an example, using pressure information from both the first set and the second set can be more accurate for estimating both joint angles than using pressure information from either the first set or the second set alone.

In an example, a multivariate model for estimating one or more ball joint angles based on flowable substance pressures on can include an interaction term between flowable substance pressures in a first set of tubes or channels and flowable substance pressures in a second set of tubes or channels. In an example, a multivariate model for estimating changes in one or more ball joint angles based on changes in flowable substance pressures on can include an interaction term between changes in flowable substance pressures in a first set and changes in flowable substance pressures in a second set.

In an example, tubes or channels in a first set and tubes or channels in a second sets can have longitudinal centers which are located on the circumference of the same lateral cross-section of a joint, but tubes or channels in the first set can have a different angle of intersection with the longitudinal axis of the joint than tubes or channels in the second set. In an example, tubes or channels in a first set and tubes or channels in a second set can have longitudinal centers which are located on the circumference of the same lateral cross-section of a joint, but tubes or channels in the first set can have a different radial location and/or distribution around the circumference of a joint than tubes or channels in the second set. In an example, tubes or channels in a first set and tubes or channels in a second set can have longitudinal centers which are located on the circumference of the same lateral cross-section of a joint, but tubes or channels in the first set can share a level of independence or connection (e.g. mesh or lattice) that is different than that of tubes or channels in the second set.

In an example, one or more tubes or channels in a first set can span the skin covering the outer or frontal of a joint and tubes or channels in a second set can span the skin covering the inner or dorsal surface the joint. In an example, one or more tubes or channels in a first set can span the skin covering the outer or frontal surface of a joint and the skin covering the inner or dorsal surface of the joint, while one or more tubes or channels in a second set can span the skin covering the lateral surfaces of the joint. In an example, one or more tubes or channels in a first set and one or more tubes or channels in a second set can both span a joint together at one or more shared radial locations across the circumference of the joint.

In various examples, a first set of one or more tubes or channels that spans a body joint and a second set of one or more tubes or channels that spans the same body joint can differ with respect to one or more design parameters selected from the group consisting of: the method by which tubes or channels in each set are attached to (or integrated into) an article of clothing or wearable accessory; the number of tubes or channels in a set (including having just one or multiple tubes or channels in a set); the type of tube or channel material in a set; the construction of tubes or channels in a set; the flexibility, durometer, and/or elasticity of tubes or channels in a set; the cross-sectional shape and/or cross-sectional uniformity of tubes or channels in a set; the longitudinal shape and/or longitudinal uniformity of tubes or channels in a set; the inner area size of tubes or channels in a set; the wall thickness of tubes or channels in a set; the length of tubes or channels in a set; the angle of intersection between tubes or channels in a set and the longitudinal axis of a joint; the radial locations and/or distribution of tubes or channels in a set as they cross the circumference of a joint; and the independence or connections (e.g. mesh or lattice) between tubes or channels in a set.

In an example, having pressure information from at least two different sets of tubes, wherein these sets span a joint at different radial locations around the circumference of the joint, can enable accurate estimation of joint angle regardless of circumferential shifting of the clothing or accessory around the joint. In an example, multiple sets of tubes can longitudinally span a joint at different radial locations around the circumference of the joint such that there is always one tube spanning one or more key radial location regardless of circumferential shifting of the clothing or accessory around the joint. In an example, multiple tubes can longitudinally span the joint at radial cross-sectional locations which are evenly distributed with respect to cross-sectional polar coordinates around the cross-section of the joint. In an example, these multiple tubes can be parallel but not co-axial.

In an example, having pressure information from at least two different sets of tubes, wherein these sets span different longitudinal segments of the same joint, can enable accurate estimation of joint angle regardless of longitudinal shifting of the clothing or accessory over the joint. In an example, multiple sets of tubes can span different longitudinal segments of a joint such that there is always one tube spanning one or more key longitudinal segments regardless of longitudinal shifting of the clothing or accessory over the joint. In an example, multiple tubes can longitudinally span different, equal-length longitudinal segments of the longitudinal axis of a joint. In an example, the axes of these multiple tubes extending out beyond the physical tubes can be coaxial.

FIGS. 7 through 9 further illustrate how the use of two sets of tubes or channels which have different design characteristics and which span the same body joint can enable more accurate measurement of the functional relationship between joint angle and substance pressure than use of a single set of tubes or channels. More accurate measurement of the functional relationship between joint angle and substance pressure also enables more accurate prediction of joint angle given substance pressure when this functional relationship is used in reverse. This, in turn, enables more accurate measurement, recognition, and modeling of human motion.

FIG. 7 shows the first set of (long) tubes (including tubes 601, 604, and 607) spanning a body joint that were introduced in FIG. 6. However, in the example shown in FIG. 7, this first set of (long) tubes is the only set of tubes spanning the joint. A related conceptual graph of the functional relationship between body joint angle and pressure within this first set of (long) tubes is shown on the right side of FIG. 7. As shown in the graph in FIG. 7, the wider scattering of data points in the lower-range of joint angles and the narrower scattering of data points in the higher-range of joint angles means that this first set of (long) tubes is less accurate for estimating the functional relationship in the lower-range of joint angles and more accurate for estimating the functional relationship in the higher-range of joint angles.

FIG. 8 shows the second set of (short) tubes (including tubes 610, 613, and 616) spanning a body joint that were introduced in FIG. 6. However, in the example shown in FIG. 8, this second set of (short) tubes is the only set of tubes spanning the joint. A related conceptual graph of the functional relationship between body joint angle and pressure within this second set of (short) tubes is shown on the right side of FIG. 8. As shown in the graph in FIG. 8, the narrower scattering of data points in the lower-range of joint angles and the wider scattering of data points in the higher-range of joint angles means that this second set of (short) tubes is more accurate for estimating the functional relationship in the lower-range of joint angles and less accurate for estimating the functional relationship in the higher-range of joint angles.

FIG. 9 shows a wearable device that combines both the first set of (long) tubes from FIG. 7 and the second set of (short) tubes from FIG. 8. The wearable device that is shown in FIG. 9 is also a repeat of the device introduced in FIG. 6. The related conceptual graph of a multivariate functional relationship between body joint angle and pressure in both sets in shown on the right side of FIG. 9. By using pressure information from both the first set and the second set in multivariate analysis, one can achieve higher accuracy in functional prediction across lower-range and higher-range body joint angles. When this multivariate functional relationship is used in reverse to predict joint angle given multiple pressure levels in both sets, higher accuracy of body joint angle prediction can be achieved.

In the example shown in FIGS. 7 through 9, two sets of tubes or channels spanning the same joint enable more accurate estimation of the functional relationship between body joint angle and pressure because these two sets differ with respect to their length. In other examples, two sets of tubes or channels spanning the same joint can enable more accurate estimation of this functional relationship because they differ with respect to other design characteristics.

In an example, two sets of different types of tubes or channels spanning the same body joint can differ with respect to whether they can be refilled or re-pressurized with a flowable substance. In an example, two sets of different types of tubes or channels spanning the same body joint can differ with respect to the angle at which tubes or channels in a set cross or are parallel to the longitudinal axis of a joint. In an example, two sets of different types of tubes or channels spanning the same body joint can differ with respect to the angle at which tubes or channels in a set span the longitudinal axis of a joint.

In an example, two sets of different types of tubes or channels spanning the same body joint can differ with respect to the baseline flowable substance pressures in a set of tubes or channels (when a joint is fully extended). In an example, two sets of different types of tubes or channels spanning the same body joint can differ with respect to characteristics of the portions of tubes or channels in a set that span the center portion of a joint being different than those of the portions of tubes or channels in a set that span the peripheral portions of a joint.

In an example, two sets of different types of tubes or channels spanning the same body joint can differ with respect to the compressibility of tubes or channels in a set. In an example, two sets of different types of tubes or channels spanning the same body joint can differ with respect to the construction of tubes or channels in a set. In an example, two sets of different types of tubes or channels spanning the same body joint can differ with respect to the cross sectional size of tubes or channels in a set.

In an example, two sets of different types of tubes or channels spanning the same body joint can differ with respect to the cross-sectional curvature of tubes or channels in a set. In an example, two sets of different types of tubes or channels spanning the same body joint can differ with respect to the cross-sectional shape of tubes or channels in a set. In an example, two sets of different types of tubes or channels spanning the same body joint can differ with respect to cross-sectional shape variation or uniformity of tubes or channels in a set.

In an example, two sets of different types of tubes or channels spanning the same body joint can differ with respect to the density of a flowable substance in tubes or channels in a set. In an example, two sets of different types of tubes or channels spanning the same body joint can differ with respect to the durometer of tubes or channels in a set. In an example, two sets of different types of tubes or channels spanning the same body joint can differ with respect to the elasticity of tubes or channels in a set.

In an example, two sets of different types of tubes or channels spanning the same body joint can differ with respect to the flexibility of tubes or channels in a set. In an example, two sets of different types of tubes or channels spanning the same body joint can differ with respect to the frequency of calibration of tubes or channels in a set. In an example, two sets of different types of tubes or channels spanning the same body joint can differ with respect to having separate or inter-connected tubes or channels (such as mesh or lattice) in a set.

In an example, two sets of different types of tubes or channels spanning the same body joint can differ with respect to the interior cross-sectional area of tubes or channels in a set. In an example, two sets of different types of tubes or channels spanning the same body joint can differ with respect to the (average) length of tubes or channels in a set. In an example, two sets of different types of tubes or channels spanning the same body joint can differ with respect to the locations of pressure sensors in tubes or channels in a set.

In an example, two sets of different types of tubes or channels spanning the same body joint can differ with respect to the longitudinal curvature of tubes or channels in a set. In an example, two sets of different types of tubes or channels spanning the same body joint can differ with respect to longitudinal shape variation or uniformity of tubes or channels in a set. In an example, two sets of different types of tubes or channels spanning the same body joint can differ with respect to the method by which tubes or channels in a set are attached to (or integrated with) an article of clothing or wearable article.

In an example, two sets of different types of tubes or channels spanning the same body joint can differ with respect to the method of calibration of tubes or channels in a set. In an example, two sets of different types of tubes or channels spanning the same body joint can differ with respect to the number of tubes or channels (including one or multiple tubes or channels) in a set. In an example, two sets of different types of tubes or channels spanning the same body joint can differ with respect to the radial locations (e.g. measured as polar coordinate) at which tubes or channels in a set cross a lateral cross-section of a body joint.

In an example, two sets of different types of tubes or channels spanning the same body joint can differ with respect to the segment of the longitudinal axis of a joint that is spanned by tubes or channels in a set. In an example, two sets of different types of tubes or channels spanning the same body joint can differ with respect to the type of article of clothing or wearable accessory to which tubes or channels in a set are attached. In an example, two sets of different types of tubes or channels spanning the same body joint can differ with respect to the type of flowable substance within tubes or channels in a set.

In an example, two sets of different types of tubes or channels spanning the same body joint can differ with respect to the type of material used for tubes or channels in a set. In an example, two sets of different types of tubes or channels spanning the same body joint can differ with respect to the type of pressure sensor in a set. In an example, two sets of different types of tubes or channels spanning the same body joint can differ with respect to the use of data from supplemental sensors such as a thermometer, altimeter, and/or GPS when estimating the relationship between body joint angle and pressure, or vice versa.

In an example, two sets of different types of tubes or channels spanning the same body joint can differ with respect to the use of Fourier analysis of repeated pressure variation in a set. In an example, two sets of different types of tubes or channels spanning the same body joint can differ with respect to the viscosity of a flowable substance in tubes or channels in a set. In an example, two sets of different types of tubes or channels spanning the same body joint can differ with respect to the wall thickness of tubes or channels in a set.

In an example, two sets of different types of tubes or channels spanning the same body joint can differ with respect to whether a given set or tubes or channels spans one joint or multiple joints. In an example, two sets of different types of tubes or channels spanning the same body joint can differ with respect to whether a set comprises balloon-like tubes or channels. In an example, two sets of different types of tubes or channels spanning the same body joint can differ with respect to whether a set comprises primarily tubes, primarily channels, or both tubes and channels.

In an example, two sets of different types of tubes or channels spanning the same body joint can differ with respect to whether a set is comprised of braided tubes or tubes with other composite structures. In an example, two sets of different types of tubes or channels spanning the same body joint can differ with respect to and whether an article of clothing or wearable accessory to which a set is attached fits tightly or loosely.

In various examples, two sets of tubes or channels spanning the same joint angle can enable more accurate estimation of the functional relationship between body joint angle and substance pressure because the sets differ in one or more design characteristics. In various examples, these one or more design characteristics can be selected from the group consisting of: ability to refill or re-pressurize a flowable substance in tubes or channels in a set; angle at which tubes or channels in a set cross or are parallel to the longitudinal axis of a joint; angle at which tubes or channels in a set span the longitudinal axis of a joint; baseline flowable substance pressures in a set of tubes or channels (when a joint is fully extended); characteristics of the portions of tubes or channels in a set that span the center portion of a joint vs. the peripheral portions of a joint; compressibility of tubes or channels in a set; construction of tubes or channels in a set; cross-sectional size of tubes or channels in a set; cross-sectional curvature of tubes or channels in a set; cross-sectional shape of tubes or channels in a set; cross-sectional shape variation or uniformity of tubes or channels in a set; density of a flowable substance in tubes or channels in a set; durometer of tubes or channels in a set; elasticity of tubes or channels in a set; flexibility of tubes or channels in a set; frequency of calibration of tubes or channels in a set; having separate or inter-connected tubes or channels (such as a mesh or lattice) in a set; interior cross-sectional area of tubes or channels in a set; length of tubes or channels in a set; locations of pressure sensors in tubes or channels in a set; longitudinal curvature of tubes or channels in a set; longitudinal shape variation or uniformity of tubes or channels in a set; method by which tubes or channels in a set are attached to (or integrated with) an article of clothing or wearable article; method of calibration of tubes or channels in a set; number of tubes or channels (including having one or multiple tubes or channels) in a set; radial locations (e.g. measured using polar coordinates) at which tubes or channels in a set cross a lateral cross-section of a body joint; segment of the longitudinal axis of a joint that is spanned by tubes or channels in a set; type of article of clothing or wearable accessory to which tubes or channels in a set are attached; type of flowable substance within tubes or channels in a set; type of material used for tubes or channels in a set; type of pressure sensor in a set; use of data from supplemental sensors such as a thermometer, altimeter, and/or GPS; use of Fourier analysis of repeated pressure variation; viscosity of a flowable substance in tubes or channels in a set; wall thickness of tubes or channels in a set; whether a given set or tubes or channels spans one joint or multiple joints; whether a set comprises balloon-like tubes or channels; whether a set comprises primarily tubes, primarily channels, or both tubes and channels; whether a set is comprised of braided tubes or tubes with other composite structures; and whether an article of clothing or wearable accessory to which a set is attached fits tightly or loosely.

FIG. 10 shows an example of a wearable device for recognizing human motion in which different sets of tubes or channels span different longitudinal segments of the longitudinal axis of a body joint. In this example, a first set of parallel tubes (including tube 1001) spans a portion of the body segment that comprises the upper and/or proximal member of the body joint. In this example, a second set of parallel tubes (including tube 1002) spans the central portion of the body joint where the upper and/or proximal member and the lower and/or distal member of the body joint connect with each other. In this example, a third set of parallel tubes (including tube 1003) spans a portion of the body segment that comprises the lower and/or distal member of the body joint.

In an example, these three different sets of parallel tubes or channels can measure different ranges of body joint angles with greatest accuracy. In an example, one set can most-accurately measure low-range body joint angles, another set can most accurately measure mid-range body joint angles, and another set can most-accurately measure high-range body joint angles. In an example, incorporating pressure information from all three sets in multivariate analysis can provide greater measurement and estimation accuracy than using information from one set alone. In an example, having different sets of tubes or channels that span different longitudinal segments of a body joint can enable more accurate estimation of body joint angle over the full range of body joint angles. This, in turn, can enable more accurate recognition and modeling of human motion.

As shown in FIG. 10, this invention can be embodied in a wearable device for recognizing human motion in which a first set of tubes or channels have longitudinal centers which are located around a circumference which is different than the circumference around which the longitudinal centers of a second set of tubes or channels are located. In an example, tubes or channels in a first set can span a different longitudinal segment of the longitudinal axis of a joint than the longitudinal segment that is spanned by tubes or channels in a second set.

FIG. 11 shows an example of a wearable device for recognizing human motion in which different sets of tubes or channels span the same body joint at different angles with respect to the longitudinal axis of the joint. In this example, a first set of tubes (including tubes 1101 and 1104) span the longitudinal axis of a joint in a manner which is substantially parallel to the longitudinal axis of the joint (especially when the joint is fully extended). In this example, a second set of tubes (including tubes 1102 and 1106) spans the longitudinal axis of the joint at an acute angle with respect to the longitudinal axis of the joint. In this example, a third set of tubes (including tubes 1103 and 1105) spans the longitudinal axis of the joint at a different angle with respect to the longitudinal axis of the joint.

In an example, these three different sets of tubes or channels can have greater measurement accuracy over different body joint ranges. In an example, incorporating pressure information from all three sets can enable more accurate estimation of body joint angle in this hinge joint than using information from only one set. In an example, different sets of tubes or channels that span a joint at different angles can be used to estimate a single angle of a hinge joint (e.g. a knee in this example).

In another example, different sets of tubes or channels that span a joint at different angles can be especially useful for measuring the multi-angle movements of a ball-and-socket joint (e.g. such as a shoulder or hip). In an example, sets of tubes or channels which span a joint at acute angles (such as the second and third sets in FIG. 11) can be particularly useful for measuring rotation or twisting of a ball-and-socket joint. Using different sets of tubes or channels that span a complex body segment or joint (such as a person's wrist, foot, torso, and/or back) at different angles can also be useful for measuring bending or twisting of such a complex body segment or joint.

FIG. 12 shows an example of a wearable device for recognizing human motion in which tubes or channels (including tubes or channels 1201, 1202, and 1203) span a body joint in a curvaceous manner. In this example, the curvaceous manner in which tubes or channels span a body joint is sinusoidal. In an example, having tubes or channels span a body joint in a curvaceous manner can increase the surface area of an article of clothing or wearable accessory over which pressure changes can be measured with a limited number of pressure sensors. In an example, having tubes or channels span a body joint in a curvaceous manner can decrease the potential for constriction (by the tubes or channels) of the person's movements.

In an example, having tubes or channels span a body joint in a curvaceous manner can better control for slipping or sliding of the article or accessory with respect to the person's skin when the joint bends. In an example, pressure values in a sinusoidal tube can be less affected by circumferential slipping or sliding of an article or accessory than pressure values in a straight tube. In an example, having sinusoidal tubes or channels span a body joint can be advantageous for estimating body joint angle with a looser-fitting article of clothing or wearable accessory.

FIG. 13 shows an example of a wearable device for recognizing human motion that comprises one or more spiral tubes or channels (including spiral tube or channel 1301) which wrap around the circumference of a body joint. In this example, there are multiple pressure sensors (1302) at different locations within spiral tube or channel (1301) which wraps around the circumference of a body joint. Pressure measurements at different locations within spiral tube or channel 1301 can provide more accurate measurement of joint movement than a single measure of pressure at one location within the tube or channel. In this example, different pressure sensors are aligned along a common (lateral) side of the body joint. In another example, different pressure sensors can be located on different sides of a body joint.

In an example, having one or more tubes or channels span a body joint in a spiral manner can increase the surface area of an article of clothing or wearable accessory over which pressure changes can be measured. In an example, having tubes or channels span a body joint in a spiral manner can lower the potential for constriction of the person's movement by the tubes or joints.

In an example, having tubes or channels span a body joint in a spiral manner can better control for slipping or sliding of the article or accessory with respect to the person's skin as the joint bends. In an example, pressure values in a spiral tube can be less affected by circumferential slipping or sliding of an article or accessory than pressure values in a straight tube that spans a joint longitudinally. In an example, having one or more tubes that span a body joint in a spiral manner can be advantageous for estimating body joint angle with a looser-fitting article of clothing or wearable accessory. In an example, having one or more tubes that span a body joint in a spiral manner can be advantageous for modeling the movements of a ball-and-socket joint.

FIG. 14 shows an example of how a wearable device for measuring human motion can be used for sports training and/or virtually-interactive sports. FIG. 14 shows a golfer (1401) who is wearing a stretchable union suit (1402) which contains multiple sets of tubes or channels (including 1403) which span multiple joints including the golfer's knees, hips, torso, shoulders, and elbows. In an example, such a suit could include gloves which span the golfer's wrists and fingers. In an example, an accelerometer can also be incorporated into the golf club as part of a system for measuring both human motion and motion of the golf club. In an example, an accelerometer can be incorporated into the golf ball to further comprise a system for sports training and/or virtually-interactive golf.

In the example that is shown in FIG. 14, information concerning pressure levels in the multiple sets of tubes or channels (1403) spanning multiple joints is transmitted via wireless signals (such as 1404) to a computer (1405) which uses this pressure information to recognize and model full-body motion of the golfer. In this example, the computer (1405) uses this pressure information to animate a virtual avatar (1406) of the golfer.

In an example, pressure information can be analyzed by computer 1405 to provide recommendations to the golfer concerning how the golfer can improve their game by changing body posture and/or motions. In an example, analysis of pressure information and provision of recommendations by computer 1405 can be retrospective in nature, provided after a game has been played. In an example, analysis of pressure information and provision of recommendations by computer 1405 can occur in real time, while a game is being played.

In an example, recommendations for body posture and/or motion improvement can be conveyed from computer 1405 to golfer 1401 by a synthesized voice output. In an example, a computer can say—"You're your left arm up around 10 degrees", "Straighten up, you duffer", "Stop that, you hacker", or "Got get 'em, tiger!" In an example, recommendations for body posture and/or motion improvement can be conveyed by non-verbal sounds or music. In an example, a computer can play negatively-reinforcing music when a golfer has bad body posture and/or inefficient movements and can play positively-reinforcing music when a golfer has good body posture and/or efficient movements.

In an example, recommendations for posture and/or motion improvement can be conveyed from computer 1405 to golfer 1401 by tactile sensations conveyed through a wearable device. In an example, a first pattern of vibration can prompt body joint movement in a first direction and a second pattern of vibration can prompt body joint movement in a second direction. In an example, a shorter duration of vibration can prompt body joint movement by a smaller angle and a longer duration of vibration can prompt body joint movement by a larger angle.

In an example, recommendations for body posture and/or motion improvement can be conveyed from the computer to the golfer via electronically-functional eyewear or via a smart watch that is worn by the golfer. In an example, recommendations for body posture and/or motion improvement can be conveyed from the computer to the golfer in a visual manner via augmented reality. In an example, recommended positions for body joints and/or body segments can appear superimposed over actual positions of body joints and/or body segments in a player's field of vision using electronically-functional eyewear.

In an example, a device for recognizing human motion related to a sports game, such as that shown in FIG. 14, can be incorporated into a system for virtually-interactive sports. In an example, such a system can enable a person to interact virtually with a remote golf course. In an example, such a system can enable people who are in physically-different locations to interact virtually in a common sports game. In an example, such a system can enable multiple people to participate and interact in a sports game in a virtual reality environment. In an example, such a system can enable remote sports instruction or training between a trainer and trainee who are in physically-different locations.

In an example, a device for recognizing full-body human motion such as the one shown in FIG. 14 can be used for computer gaming. In an example such a device can be used to control the movements of a virtual avatar in a multiplayer online game and/or in a virtual reality world. In an example, the movements of a person wearing a full-body device for recognizing human motion can animate a virtual knight, orc, dragon . . . or even an virtual actuary!

In an example, a device for recognizing full-body motion such as the one shown in FIG. 14 can be used for medical diagnosis of motion disorders or for diagnosis of an underlying medical condition based on motion-related symptoms. In an example, a device for recognizing full-body motion such as the one shown in FIG. 14 can be used for virtual exercise. In an example, such a device can be used for motivating group exercise by people who are in physically-different locations.

FIG. 15 shows an example of how a wearable device for recognizing full-body human motion can be used to track and display caloric expenditure. There are pedometers, smart watches, and other wearable single-location devices in the prior art which include accelerometers. Such devices can be used to estimate a person's caloric expenditure based on movement of a device at a single location on a person's body. However, such devices can be blind to the relative motion of body segments which is not captured at their location. For example, a device that is fastened to a person's belt may not capture calories burned by arm motions which do not move the person's torso. Also, a device fastened to a person's wrist may be unable to distinguish between walking and hammering. These problems with single-location (accelerometer-based) devices can lead to inaccuracy in measurement of total caloric expenditure. The wearable device that is shown in FIG. 15 can solves these problems by capturing substantially full-body human motion comprising movement of multiple body joints, including the movements of body segments relative to each other.

In the example shown in FIG. 15, the angle ranges and speeds of movements of multiple body joints are estimated by changes in the pressures in sets of tubes or channels that span those multiple body joints. The angle ranges and speeds of movements of multiple body joints can then be used to estimate total caloric expenditure. In an example, joint movements with large angle ranges can be associated with burning more calories. In an example, faster joint movements can be associated with burning more calories. In an example, movements of joints associated with larger muscles can be associated with burning more calories. In an example, information concerning pressure changes from multiple sets of tubes or channels can be supplemented by information from one or more accelerometers and/or a GPS for multivariate prediction of total caloric expenditure.

In the example shown in FIG. 15, total caloric expenditure (1502) that is estimated based on movements of multiple joints is displayed on a smart watch (1501) that is worn by a person. In an example, total caloric expenditure that is estimated based on movements of multiple joints can be conveyed to a person via electronically-functional eyewear. In an example, estimated caloric expenditure can be incorporated into a system for total energy balance and weight management.

In an example, specifically-identifiable patterns of joint movements can be associated with probable food consumption. In an example, a person can be prompted to record food consumption information when a wearable device for recognizing human motion recognizes a pattern of joint movements that indicates probable food consumption. In an example, a device for recognizing human motion can be in electronic communication with a mobile device application for entering food consumption information. In an example, a wearable device for recognizing human motion can be part of an overall system for measuring a person's caloric intake, measuring the person's caloric expenditure, and helping the person to manage their overall energy balance and body weight.

FIG. 16 shows examples of how the functional relationship between joint angle and substance pressure can change with changes in how tightly or loosely an article of clothing or wearable accessory fits over a body joint. In this example, the body joint is a knee. The top third of FIG. 16 shows an example of a wearable device (including wearable article 102, tube 103, and pressure sensor 104) for recognizing human motion in which wearable accessory 102 fits relatively-tightly over body joint 1501. The related conceptual graph of the functional relationship between body joint angle and pressure is shown on the right side of this example, connected to the physical device by a dotted line arrow which represents data transmission.

The middle third of FIG. 16 shows an example of this same wearable device being worn over a smaller-diameter body joint. In an example, this smaller-diameter body joint can be the knee of a smaller person. The smaller size of this middle body joint is represented symbolically by four dotted-line arrows pointing inwards on either side of the joint. The conceptual graph that is associated with this middle example shows that the functional relationship between joint angle and substance pressure has shifted downwards for this smaller joint wherein the wearable article does not fit as tightly.

A loose-fitting wearable device for recognizing human motion can still use the functional relationship between joint angle and substance pressure in reverse in order to predict joint angle based on substance pressure, but the lower functional curve should be used. In an example, a wearable device can be less sensitive to changes in low-range joint angles when it does not fit as tightly over a joint. However, having two or more sets of tubes or channels with different design parameters can help to achieve high measurement accuracy, even when a wearable device does not fit as tightly over a joint.

The bottom third of FIG. 16 shows an example of this same wearable device being worn over an even smaller-diameter body joint. In this example, tubular wearable accessory 102 fits quite loosely over a person's knee. The conceptual graph associated with this third example shows an even greater downward shift in the functional relationship between body joint angle and substance pressure. Nonetheless, having two or more sets of tubes or channels with different design parameters can help to achieve high measurement accuracy, even when a wearable device fits loosely over a joint. In an example, at least one set of tubes or channels can be very flexible and thin-walled for maximum sensitivity to small angle bending of the joint.

FIG. 17 shows an example of a wearable device for recognizing human motion which has a central data transmitter (1701) which can be detached and removed from an article of clothing or wearable accessory so that the article or accessory can be washed. In an example, although not shown in the opaque article view in FIG. 17, multiple sets of tubes or channels which span multiple joints can all be connected to the central data transmitter by small sinusoidal wires. In an example, pressure information from those multiple sets can be conveyed to a central data transmitter, from which this information can be transmitted to a remote data processor for analysis.

FIG. 18 shows an example of a wearable device for recognizing human motion in which multiple parallel tubes or channels containing a flowable substance are woven into the fabric of an article of clothing or wearable accessory. The lower left portion of FIG. 18 shows golfer 1401 wearing suit 1402 which includes a central data transmitter 1701 which receives pressure information from multiple sets of tubes or channels through wires (such as wire 1801). The lower left portion of FIG. 18 also shows a small dotted-line rectangle (1802) which spans the frontal surface a golfer's right knee. The upper right portion of FIG. 18 shows a larger dotted-line rectangle (1802) which is an enlarged view of the small dotted-line rectangle (1802) which spans the frontal surface of the golfer's right knee.

The larger dotted-line rectangle 1802 which is shown in the upper right portion of FIG. 18 shows an enlarged view of the fabric of this wearable suit into which multiple parallel tubes or channels have been woven. In this example, the weave of this fabric includes multiple tubes or channels (1804) and stretchable threads or fibers (1803). In this example, there are miniature pressure sensors (1805) within tubes or channels (1804) which measure the pressure levels of a flowable substance within each of those tubes or channels.

In this example, the weave of the fabric of the suit is oriented so that the tubes or channels (1804) span the person's knee in a longitudinal manner. In another example, the weave of the fabric of the suit could be oriented so that the tubes or channels span the person's knee in a lateral manner. In an example, tubes or channels could be incorporated into fabric in both directions so that some tubes or channels span the knee in a longitudinal manner and other tubes or channels span the knee in a lateral manner.

In the example that is shown in FIG. 18, the same fabric is used across all portions of suit 1402 in order to span multiple joints with sets of tubes or channels that are woven into suit 1402. In this manner, suit 1402 can provide virtually full-body motion recognition. In this example, the pressure sensors are contained within the tubes or channels. In this example, data from the pressure sensors is conveyed to a central data transmitter 1701 via small sinusoidal wires (such as 1801). In this example, data transmitter 1701 can be detached from the suit and the suit can be washed without harming pressure sensors 1805.

FIG. 19 shows another example of a wearable device for recognizing human motion in which multiple tubes or channels containing a flowable substance are woven into the fabric of an article of clothing or wearable accessory. This example is similar to the one that was shown in FIG. 18 except that now the tubes or channels span the body joint in both longitudinal and lateral directions. In this example, perpendicular sets of tubes or channels form a mesh or lattice in the fabric of the wearable article or accessory. Having perpendicular sets of tubes or channels woven into fabric can add to the complexity of the wearable device, but can also improve the accuracy of the wearable device in measuring and modeling complex human motion.

The lower left portion of FIG. 19 shows golfer 1401 wearing suit 1402 which includes a central data transmitter 1701 which receives pressure information from multiple sets of tubes or channels through wires (such as wire 1801). The lower left portion of FIG. 19 also shows a small dotted-line rectangle (1802) which spans the frontal surface a golfer's right knee. The upper right portion of FIG. 19 shows a larger dotted-line rectangle (1820) is an enlarged view of the small dotted-line rectangle (1802) which spans the frontal surface of the golfer's right knee.

The larger dotted-line rectangle 1802 which is shown in the upper right portion of FIG. 19 shows an enlarged view of the fabric of this wearable suit into which perpendicular sets of tubes or channels have been woven. In this example, this fabric includes a first set (1804) of tubes or channels which span the body joint in a longitudinal manner and a second set (1901) of tubes or channels which span the same body joint in a lateral manner. In this example, there is a first set (1805) of miniature pressure sensors in the first set (1804) of tubes or channels and a second set (1902) of miniature pressure sensors in the second set (1901) of tubes or channels. This example of a wearable device to measure and recognize human motion can comprise a tube or channel matrix, mesh, or lattice that is constructed using microfluidics. In an example, this wearable device can be a microfluidic device.

In the example that is shown in FIG. 19, the same fabric can be used across all portions of suit 1402 in order to span multiple joints with sets of tubes or channels that are woven into suit 1402. In this manner, suit 1402 can provide virtually full-body motion recognition. In this example, pressure sensors are contained within tubes or channels in the first set and in the second set. In this example, data from the pressure sensors in the first set and pressure sensors in the second set can be separately conveyed via different wires to central data transmitter 1701.

FIGS. 1 through 19 show examples of how a wearable device for recognizing human motion can comprise: an article of clothing or wearable accessory that is configured to span at least a portion of at least one body joint; at least one pressure sensor; at least one flowable substance; a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor; a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, and wherein one or more design characteristics are different for the second set than for the first set; and a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

In various examples, the one or more design characteristics which differ between the first set and the second set can be selected from the group consisting of: ability to refill or re-pressurize a flowable substance in tubes or channels in a set; angle at which tubes or channels in a set cross or are parallel to the longitudinal axis of a joint; angle at which tubes or channels in a set span the longitudinal axis of a joint; baseline flowable substance pressures in a set of tubes or channels when a joint is fully extended; characteristics of the portions of tubes or channels in a set that span the center portion of a joint vs. the peripheral portions of a joint; compressibility of tubes or channels in a set; construction of tubes or channels in a set; cross-sectional size of tubes or channels in a set; cross-sectional curvature of tubes or channels in a set; cross-sectional shape of tubes or channels in a set; cross-sectional shape variation or uniformity of tubes or channels in a set; density of a flowable substance in tubes or channels in a set; durometer of tubes or channels in a set; elasticity of tubes or channels in a set; flexibility of tubes or channels in a set; frequency of calibration of tubes or channels in a set; having separate or inter-connected tubes or channels in a set; interior cross-sectional area of tubes or channels in a set; length of tubes or channels in a set; locations of pressure sensors in tubes or channels in a set; longitudinal curvature of tubes or channels in a set; longitudinal shape variation or uniformity of tubes or channels in a set; method by which tubes or channels in a set are attached to or integrated with an article of clothing or wearable article; method of calibration of tubes or channels in a set; number of tubes or channels in a set; radial locations at which tubes or channels in a set cross a lateral cross-section of a body joint; segment of the longitudinal axis of a joint that is spanned by tubes or channels in a set; type of article of clothing or wearable accessory to which tubes or channels in a set are attached; type of flowable substance within tubes or channels in a set; type of material used for tubes or channels in a set; type of pressure sensor in a set; use of data from supplemental sensors such as a thermometer, altimeter, and/or GPS; use of Fourier analysis of repeated pressure variation; viscosity of a flowable substance in tubes or channels in a set; wall thickness of tubes or channels in a set; whether a given set or tubes or channels spans one joint or multiple joints; whether a set comprises balloon-like tubes or channels; whether a set comprises primarily tubes, primarily channels, or both tubes and channels; whether a set is comprised of braided tubes or tubes with other composite structures; and whether an article of clothing or wearable accessory to which a set is attached fits tightly or loosely.

In an example, there can be a first functional relationship between body joint angles and pressures in a first set, there can be a second functional relationship between body joint angles and pressures in a second set, the first functional relationship can be different than the second functional relationship, and using pressure information from both a first set and a second set can enable more accurate estimation of body joint angles than using pressure information from either a first set alone or a second set alone.

In an example, the relationship between body joint angles and pressures in a first set can be more accurate or predictable over a first range of body joint angles, the relationship between body joint angles and pressures in a second set can be more accurate or predictable over a second range of body joint angles, and using pressure information from both a first set and a second set can enable more accurate or predictable estimation of body joint angles over a wider range of body joint angles than using pressure information from either a first set alone or a second set alone.

In an example, a first set and a second set can differ with respect to the radial locations at which tubes or channels in a set cross a lateral cross-section of a body joint. In an example, a first set and a second set can differ with respect to the length of tubes or channels in a set. In an example, a first set and a second set can differ with respect to the angle at which tubes or channels in a set cross or are parallel to the longitudinal axis of a joint when the joint is fully extended. In an example, a first set and a second set can differ with respect to the cross-sectional shape of tubes or channels in a set. In an example, a first set and a second set can differ with respect to the cross sectional size of tubes or channels in a set. In an example, a first set and a second set can differ with respect to the interior cross-sectional area of tubes or channels in a set.

In an example, a first set and a second set can differ with respect to the segment of the longitudinal axis of a joint that is spanned by tubes or channels in a set. In an example, a first set and a second set can differ with respect to the compressibility of tubes or channels in a set. In an example, a first set and a second set can differ with respect to the longitudinal curvature of tubes or channels in a set. In an example, a first set and a second set can differ with respect to the type of material used for tubes or channels in a set. In an example, a first set and a second set can differ with respect to the wall thickness of tubes or channels in a set.

In an example, a functional relationship between joint angle and pressure can be identified during a calibration period and this functional relationship can be used in reverse to predict joint angle based on pressure during a use period. In an example, a device can also use information from one or more other sensors selected from the group consisting of: accelerometer, altimeter, thermometer, and GPS. In an example, differences in pressure information from a first set and a second set can enable a device to distinguish between changes in pressure that are caused by joint movement and changes in pressure that are caused by compressive contact between a person and an external object in the environment.

FIGS. 1 through 19 show examples of a wearable device for recognizing human motion comprising: (a) an article of clothing or wearable accessory that is configured to span at least a portion of at least one body joint; (b) at least one pressure sensor; (c) at least one flowable substance; (d) a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor; (e) a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, wherein one or more design characteristics are different for the second set than for the first set, and wherein these one or more design characteristics are selected from the group consisting of: the angle at which tubes or channels in a set cross or are parallel to the longitudinal axis of a joint when the joint is fully extended; the baseline flowable substance pressures in a set of tubes or channels when a joint is fully extended; the compressibility of tubes or channels in a set; the cross-sectional size of tubes or channels in a set; the cross-sectional curvature of tubes or channels in a set; the cross-sectional shape of tubes or channels in a set; the cross-sectional shape variation or uniformity of tubes or channels in a set; having separate or inter-connected tubes or channels such as a mesh or lattice in a set; the length of tubes or channels in a set; the locations of pressure sensors in tubes or channels in a set; the longitudinal curvature of tubes or channels in a set; segment of the longitudinal axis of a joint that is spanned by tubes or channels in a set; the type of flowable substance within tubes or channels in a set; the viscosity of a flowable substance in tubes or channels in a set; and the wall thickness of tubes or channels in a set; and (f) a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

FIGS. 1 through 19 also show examples of a method for recognizing human motion comprising: (a) creating an article of clothing or wearable accessory that is configured to span at least a portion of at least one body joint; (b) attaching or integrating a first set of tubes or channels and the article or accessory, wherein this first set of tubes contains a flowable substance, and wherein the pressure of this flowable substance is measured by at least one pressure sensor; and (c) attaching or integrating a second set of tubes or channels and the article or accessory, wherein this second set of tubes contains a flowable substance, wherein the pressure of this flowable substance is measured by at least one pressure sensor, and wherein one or more design parameters of the second set differ from those of the first set, and wherein these design parameters are selected from the group consisting of: the angle at which tubes or channels in a set cross or are parallel to the longitudinal axis of a joint when the joint is fully extended; the baseline flowable substance pressures in a set of tubes or channels when a joint is fully extended; the compressibility of tubes or channels in a set; the cross-sectional size of tubes or channels in a set; the cross-sectional curvature of tubes or channels in a set; the cross-sectional shape of tubes or channels in a set; the cross-sectional shape variation or uniformity of tubes or channels in a set; having separate or inter-connected tubes or channels such as a mesh or lattice in a set; the length of tubes or channels in a set; the locations of pressure sensors in tubes or channels in a set; the longitudinal curvature of tubes or channels in a set; segment of the longitudinal axis of a joint that is spanned by tubes or channels in a set; the type of flowable substance within tubes or channels in a set; the viscosity of a flowable substance in tubes or channels in a set; and the wall thickness of tubes or channels in a set.

What is claimed:

1. A wearable device for recognizing human motion comprising:

an article of clothing or wearable accessory that is configured to span at least a portion of at least one body joint;

at least one pressure sensor;

at least one flowable substance;

a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor;

a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, wherein one or more design characteristics are different for the second set than for the first set, and wherein the first set and the second set differ with respect to the cross-sectional shape of tubes or channels in a set; and a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

2. A wearable device for recognizing human motion comprising:

an article of clothing or wearable accessory that is configured to span at least a portion of at least one body joint;

at least one pressure sensor;

at least one flowable substance;

a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor;

a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, wherein one or more design characteristics are different for the second set than for the first set, and wherein the first set and the second set differ with respect to the cross sectional size of tubes or channels in a set; and a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

3. A wearable device for recognizing human motion comprising:
- an article of clothing or wearable accessory that is configured to span at least a portion of at least one body joint;
- at least one pressure sensor;
- at least one flowable substance;
- a first set of one or more tubes or channels, wherein this first set is attached to or integrated into the article of clothing or wearable accessory, wherein this first set spans at least a portion of at least one body joint, wherein this first set contains a flowable substance, and wherein the pressure levels of the flowable substance in this first set are measured by at least one pressure sensor;
- a second set of one or more tubes or channels, wherein this second set is attached to or integrated into the article of clothing or wearable accessory, wherein this second set spans at least a portion of at least one body joint that is spanned by the first set, wherein this second set contains a flowable substance, wherein the pressure levels of the flowable substance in this second set are measured by at least one pressure sensor, wherein one or more design characteristics are different for the second set than for the first set, and wherein the first set and the second set differ with respect to the compressibility of tubes or channels in a set; and
- a data transmitter that receives pressure information from at least one pressure sensor and transmits this information and/or a data processor that receives pressure information from at least one pressure sensor, wherein this pressure information is used to estimate at least one angle of at least one body joint and/or to model the movement of at least one body joint, and wherein using pressure information from the first set and from the second set enables more accurate estimation of at least one angle of a body joint and/or more accurate modeling of the movement of a body joint than using pressure information from either the first set alone or the second set alone.

* * * * *